US011369405B2

(12) United States Patent
Vardi et al.

(10) Patent No.: US 11,369,405 B2
(45) Date of Patent: *Jun. 28, 2022

(54) METHOD AND SEPTOSTOMY DEVICE FOR CREATING AN INTERATRIAL APERTURE

(71) Applicant: InterShunt Technologies, Inc., St. Louis, MO (US)

(72) Inventors: Gil M. Vardi, Town and country, MO (US); Chris Minar, New Prague, MN (US)

(*) Notice: Subject to any disclaimer, the term of this patent is extended or adjusted under 35 U.S.C. 154(b) by 207 days.

This patent is subject to a terminal disclaimer.

(21) Appl. No.: 16/677,455

(22) Filed: Nov. 7, 2019

(65) Prior Publication Data

US 2020/0170662 A1 Jun. 4, 2020

Related U.S. Application Data

(63) Continuation-in-part of application No. 15/900,127, filed on Feb. 20, 2018, now Pat. No. 10,993,735, which is a continuation-in-part of application No. 15/089,547, filed on Apr. 2, 2016, now abandoned, which is a continuation-in-part of application No.

(Continued)

(51) Int. Cl.
*A61B 17/3205* (2006.01)
*A61B 17/34* (2006.01)
*A61B 17/32* (2006.01)
*A61B 17/30* (2006.01)

(Continued)

(52) U.S. Cl.
CPC .. *A61B 17/3205* (2013.01); *A61B 17/320016* (2013.01); *A61B 17/32053* (2013.01); *A61B 17/3478* (2013.01); *A61B 2017/00247* (2013.01); *A61B 2017/22042* (2013.01); *A61B 2017/22047* (2013.01); *A61B 2017/22069* (2013.01); *A61B 2017/306* (2013.01);
(Continued)

(58) Field of Classification Search
CPC ........ A61B 17/320016; A61B 17/3205; A61B 17/32053; A61B 17/3478; A61B 2017/00247; A61B 2017/00252; A61B 2017/306; A61B 2017/32004; A61B 2017/320056; A61B 2017/320064
See application file for complete search history.

(56) References Cited

U.S. PATENT DOCUMENTS 4,018,228 A 4/1977 Goosen
5,702,412 A 12/1997 Popov et al.
(Continued)

FOREIGN PATENT DOCUMENTS

WO WO 02/47561 A1 6/2002

OTHER PUBLICATIONS

Barry A. Borlaug, The sHunt for better breathing in heart failure with preserved ejection fraction, European Journal of Heart Failure, 2014, 709-11, vol. 16.
(Continued)

*Primary Examiner* — Ryan J. Severson
(74) *Attorney, Agent, or Firm* — John M. Berns

(57) ABSTRACT

A septostomy device 10 with a cutting structure or means 140 and tissue capture mechanisms 240, 250 is disclosed, along with a medical procedure for using the device. The system 10 is configured in such a way as to create a permanent interatrial aperture in the heart, including creating a permanent interatrial hole and/or removing tissue.

20 Claims, 21 Drawing Sheets

Related U.S. Application Data

14/738,802, filed on Jun. 12, 2015, now Pat. No. 9,814,483, application No. 16/677,455, which is a continuation-in-part of application No. 15/812,815, filed on Nov. 14, 2017, now Pat. No. 10,639,060, which is a continuation of application No. 14/738,802, filed on Jun. 12, 2015, now Pat. No. 9,814,483.

(60) Provisional application No. 62/012,212, filed on Jun. 13, 2014.

(51) Int. Cl.
*A61B 17/22* (2006.01)
*A61B 17/00* (2006.01)

(52) U.S. Cl.
CPC .......... *A61B 2017/320064* (2013.01); *A61B 2017/3458* (2013.01)

(56) References Cited

U.S. PATENT DOCUMENTS

| | | | |
|---|---|---|---|
| 5,893,369 A | 4/1999 | LeMole | |
| 5,910,153 A | 6/1999 | Mayenberger | |
| 6,022,367 A | 2/2000 | Sherts | |
| 6,080,173 A | 6/2000 | Williamson et al. | |
| 6,428,555 B1 | 8/2002 | Koster, Jr. | |
| 6,468,227 B2 | 10/2002 | Zimmon | |
| 6,626,921 B2 | 9/2003 | Blatter et al. | |
| 6,695,859 B1 | 2/2004 | Golden et al. | |
| 6,743,244 B2 | 6/2004 | Blatter et al. | |
| 6,863,677 B2 | 3/2005 | Breznock | |
| 6,893,449 B2 | 5/2005 | Vargas et al. | |
| 7,056,294 B2 | 6/2006 | Khairkhahan et al. | |
| 7,144,405 B2 | 12/2006 | Vargas et al. | |
| 7,771,442 B2 | 8/2010 | Shriver | |
| 7,799,041 B2 | 9/2010 | Beane et al. | |
| 8,043,360 B2 | 10/2011 | McNamara et al. | |
| 8,070,708 B2 | 12/2011 | Rottenberg et al. | |
| 8,091,556 B2 | 1/2012 | Keren et al. | |
| 8,157,860 B2 | 4/2012 | McNamara et al. | |
| 8,172,896 B2 | 5/2012 | McNamara et al. | |
| 8,216,265 B2 | 7/2012 | Haunschild et al. | |
| 8,226,670 B2* | 7/2012 | Beane | A61F 2/064 606/153 |
| 8,235,933 B2 | 8/2012 | Keren et al. | |
| 8,252,042 B2 | 8/2012 | McNamara et al. | |
| 8,328,751 B2 | 12/2012 | Keren et al. | |
| 8,460,372 B2 | 6/2013 | McNamara et al. | |
| 8,597,315 B2 | 12/2013 | Snow et al. | |
| 8,696,611 B2 | 4/2014 | Nitzan et al. | |
| 8,740,962 B2 | 6/2014 | Finch et al. | |
| 8,745,845 B2 | 6/2014 | Finch et al. | |
| 8,752,258 B2 | 6/2014 | Finch et al. | |
| 8,771,302 B2 | 7/2014 | Woolfson et al. | |
| 8,771,305 B2 | 7/2014 | Shriver | |
| 8,882,697 B2 | 11/2014 | Celermajer et al. | |
| 8,951,223 B2 | 2/2015 | McNamara et al. | |
| 8,956,377 B2 | 2/2015 | Khalapyan | |
| 9,005,155 B2 | 4/2015 | Sugimoto | |
| 9,034,034 B2 | 5/2015 | Nitzan et al. | |
| 9,205,236 B2 | 12/2015 | McNamara et al. | |
| 9,232,997 B2 | 1/2016 | Sugimoto et al. | |
| 9,277,995 B2 | 3/2016 | Celermajer et al. | |
| 9,358,371 B2 | 6/2016 | McNamara et al. | |
| 9,629,715 B2 | 4/2017 | Nitzan et al. | |
| 9,642,993 B2 | 5/2017 | McNamara et al. | |
| 9,649,480 B2 | 5/2017 | Sugimoto et al. | |
| 9,707,382 B2 | 7/2017 | Nitzan et al. | |
| 9,713,696 B2 | 7/2017 | Yacoby et al. | |
| 9,724,499 B2 | 8/2017 | Rottenberg et al. | |
| 9,757,107 B2 | 9/2017 | McNamara et al. | |
| 9,775,636 B2 | 10/2017 | Fazio et al. | |
| 9,814,483 B2* | 11/2017 | Vardi | A61B 17/32053 |
| 9,943,670 B2 | 4/2018 | Keren et al. | |
| 9,980,815 B2 | 5/2018 | Nitzan et al. | |
| 10,045,766 B2 | 8/2018 | McNamara et al. | |
| 10,188,375 B2 | 1/2019 | McNamara et al. | |
| 10,639,060 B2* | 5/2020 | Vardi | A61B 17/32053 |
| 2002/0169377 A1* | 11/2002 | Khairkhahan | A61B 17/32075 600/433 |
| 2006/0009715 A1 | 1/2006 | Khairkhahan et al. | |
| 2006/0111733 A1* | 5/2006 | Shriver | A61F 2/064 606/153 |
| 2007/0185513 A1* | 8/2007 | Woolfson | A61B 17/32002 606/108 |
| 2010/0010500 A1 | 1/2010 | Beane | |
| 2010/0057192 A1 | 3/2010 | Celermajer | |
| 2010/0121258 A1* | 5/2010 | Shriver | A61B 17/3209 604/22 |
| 2010/0298850 A1* | 11/2010 | Snow | A61B 17/320783 606/159 |
| 2011/0071623 A1 | 3/2011 | Finch et al. | |
| 2011/0218480 A1 | 9/2011 | Rettenberg et al. | |
| 2011/0218481 A1 | 9/2011 | Rettenberg et al. | |
| 2011/0270239 A1 | 11/2011 | Werneth | |
| 2011/0295183 A1 | 12/2011 | Finch et al. | |
| 2012/0259263 A1* | 10/2012 | Celermajer | A61M 29/02 604/8 |
| 2012/0265296 A1 | 10/2012 | McNamara et al. | |
| 2012/0289882 A1 | 11/2012 | McNamara et al. | |
| 2012/0290062 A1 | 11/2012 | McNamara et al. | |
| 2013/0006281 A1 | 1/2013 | Golden et al. | |
| 2013/0178784 A1 | 7/2013 | McNamara et al. | |
| 2013/0218261 A1 | 8/2013 | Beane | |
| 2013/0267885 A1 | 10/2013 | Celermajer et al. | |
| 2013/0281988 A1 | 10/2013 | Magnin et al. | |
| 2014/0128795 A1 | 5/2014 | Keren et al. | |
| 2014/0128796 A1 | 5/2014 | Keren et al. | |
| 2014/0163449 A1 | 6/2014 | Rottenberg et al. | |
| 2014/0194971 A1 | 7/2014 | McNamara | |
| 2014/0277039 A1 | 9/2014 | Liberatore et al. | |
| 2014/0277043 A1 | 9/2014 | Jenkins et al. | |
| 2014/0277045 A1* | 9/2014 | Fazio | A61B 17/320016 606/170 |
| 2014/0277054 A1 | 9/2014 | McNamara et al. | |
| 2015/0359556 A1* | 12/2015 | Vardi | A61B 17/32053 606/170 |
| 2016/0270810 A1* | 9/2016 | Vardi | A61B 17/320016 |
| 2018/0064460 A1* | 3/2018 | Vardi | A61B 17/320016 |
| 2018/0177516 A1* | 6/2018 | Vardi | A61B 17/3205 |
| 2019/0029705 A1* | 1/2019 | Vardi | A61B 17/320016 |

OTHER PUBLICATIONS

Michael A. Burke et al., Prognostic Importance of Pathophysiologic Markers in Patients With Heart Failure and Preserved Ejection Fraction, Circulation, Heart Failure, Dec. 23, 2013, 288-299, vol. 7.

Rainer Hoffmann, et al., Functional Effect of New Atrial Septal Defect After Percutaneous Mitral Valve Repair Using the MitraClip Device, Am J Cardiol, 2014: 113:1228-1233.

Lourdes R. Prieto, et al., Atrial Septostomy Using a Butterfly Stent in a Patient With Severe Pulmonary Arterial Hypertension, Catheterization and Cardiovascular Interventions, Sep. 12, 2006, 68:642-647.

Paul M. Seib, et al., Blade and Balloon Atrial Septostomy for Left Heart Decompression in Patients with Severe Ventricular Dysfunction on Extracorporeal Membrane Oxygenation, Catheterization and Cardiovascular Interventions, 1999, 46:179-186.

Lars Sondergaard et al., Transcatheter Treatment of Heart Failure with Preserved or Mildly Reduced Ejection Fraction Using a Novel Interatrial Implant to Lower Left Atrial Pressure, European Journal of Heart Failure, Jun. 24, 2014, 16:796-801.

Ignacio J. Amat-Santos et al., Left Atrial Decompression Through Unidirectional Left-to-Right Interatrial Shunt for the Treatment of Left Heart Failure: First-In-Man Experience with the new V-Wave Device, EuroIntervention, May 2014.

(56) References Cited

OTHER PUBLICATIONS

David Kaye, et al., Effects of an Interatrial Shunt on Rest and Exercise Hemodynaics: Results of a Computer Simulation in Heart Failure, Journal of Cardiac Failure, 2014, 20:3:212-21.

* cited by examiner

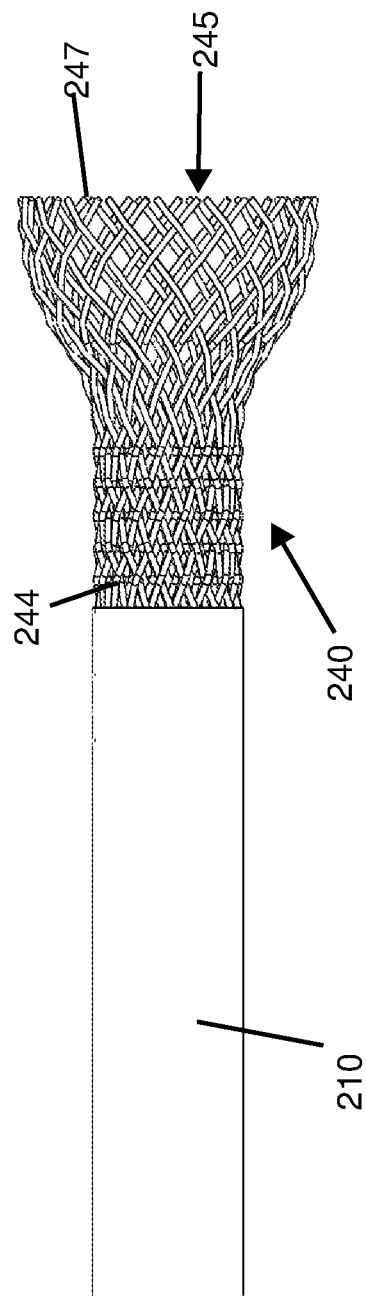
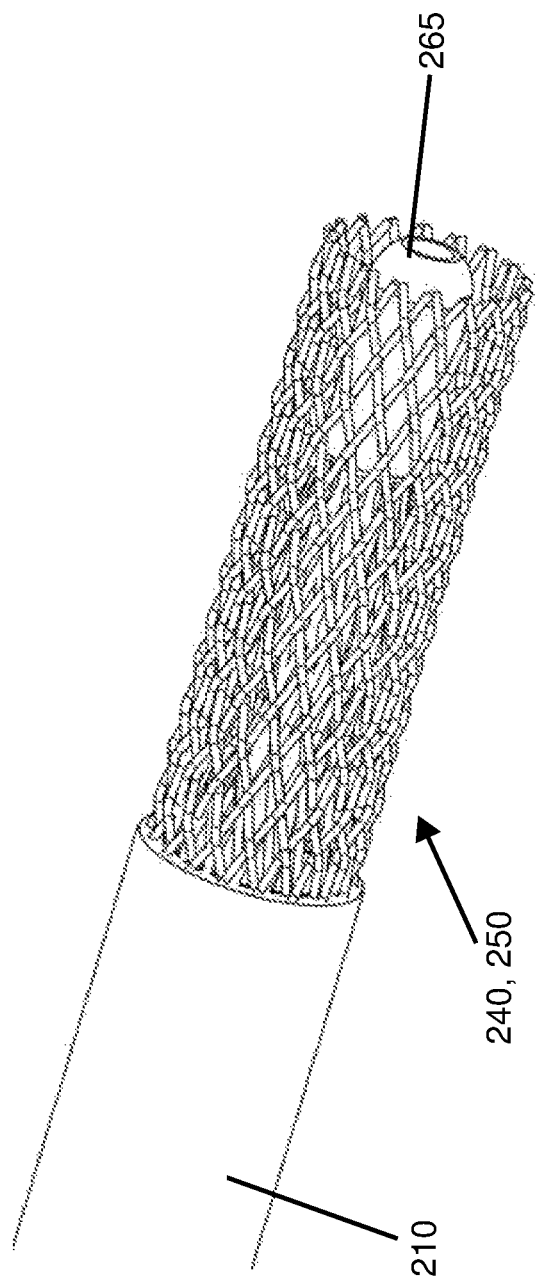
Figure 7
Figure 8a

METHOD AND SEPTOSTOMY DEVICE FOR CREATING AN INTERATRIAL APERTURE

CROSS REFERENCE TO RELATED APPLICATIONS

This application claims the benefit of priority to U.S. patent application Ser. No. 15/900,127, filed Feb. 20, 2018, which claims priority to U.S. patent application Ser. No. 15/089,547, filed Apr. 2, 2016, U.S. patent application Ser. No. 14/738,802, filed Jun. 12, 2015, now U.S. Pat. No. 9,814,483, which claims priority to U.S. Provisional Application No. 62/012,212 filed Jun. 13, 2014, the entire disclosures of which are hereby incorporated by reference. This application also claims the benefit of priority to U.S. patent application Ser. No. 15/812,815, filed Nov. 14, 2017, which also claims priority to U.S. patent application Ser. No. 14/738,802, filed Jun. 12, 2015, now U.S. Pat. No. 9,814,483, which claims priority to U.S. Provisional Application No. 62/012,212 filed Jun. 13, 2014, the entire disclosures of which are hereby incorporated by reference.

BACKGROUND OF THE INVENTION

Field of the Invention

The invention relates to medical devices and methods of medical treatment. The invention relates to a septostomy device and method of treatment used to create an aperture in the interatrial septum of a heart.

Background Art

There are some medical conditions that are treated by creating an opening between body chambers in order to create a connection between the chambers. The heart has an interatrial septum or wall that separates the left atrium and the right atrium. In certain heart failure patients (e.g., heart failure with preserved ejection fraction (diastolic dysfunction)) there is a need to allow blood flow from the left atrium to the right atrium to reduce left atrial pressure. Likewise, certain other heart diseases and conditions, such as congenital heart diseases and pulmonary hypertension may be treated by making an interatrial opening; however, the goal is to create a right-to-left shunt to reduce the high right-sided pressure.

Creating permanent apertures through the interatrial septum, and in particular, the fossa ovalis, have been enabled through various medical device technologies. One procedure uses a balloon to create a hole in the septum. However, it has been found that a hole created in this manner may not stay open and after a period of time may spontaneously close. This renders this particular therapeutic solution temporary.

A few other devices have been proposed in order to overcome the temporary solution of using a balloon. Implanting a stent in the interatrial septum has been used as a treatment for elevated pressure in one atrium by allowing blood to flow through the opening to the other atrium to reduce atrial pressure. A heart surgeon implants the stents in certain predetermined sizes in an effort to control the amount of blood flow between the atria. Thus, one method is to use a stent or stent type structure to keep the hole open. The stent type device may or may not use a valve that assists in controlling the direction of blood flow. Significant drawbacks to these devices are that they are permanent implants that can promote thrombosis and are potentially subject to infection. Furthermore, these implants require blood thinning drug regiments which may cause other medical issue. There implants also cause issues with other needed follow on surgical treatments.

Another major drawback of these devices is that they are not capable of removing a segment of the septum. The benefit of removing a segment of the septum is that aperture will be less likely to close spontaneously. The stents may also become spontaneously dislodged and embolize and cause cardiac damage or blockage of blood flow.

There are various mechanisms for creating interatrial shunts. They include dilating the tissue with a scaffold or stent type structural implant, affixing dilated tissue open thru RF ablation, and removing the tissue.

In all cases, for safety reasons, it is important to not make the interatrial shunt too large. Regardless of the desired direction of flow, it is important to control the amount of flow thru the shunt. In patients with left sided heart failure, oversized shunts can also overload the right side of the heart. However, as Lilly states in *Technologies for treating left atrial decompression in heart failure* congenital literature shows a pulmonary flow to systemic flow (Qp/Qs) ratios<1.3/1 are generally tolerable for decades. Kaye, in *Effects of an interatrial shunt on rest and exercise hemodynamics: Results of a computer simulation in heart failure* shows that shunt sizes between 8-9 mm achieved most of the shunt benefit, while keeping flow left to right in all conditions, based on a small set of heart failure patient data. There are several factors which may impact the need to broaden the shunt size range. Considering the potential range of diseases which may be treated with interatrial shunting, stage within the disease, various comorbidities, range of patient sizes, expected discharge coefficient, and the variation in expected shunt healing, the inventors have determined that an atrial shunt circular diameters of between at least 3-10 mm may be necessary.

Shah, et. al., In the publication *One-year safety and clinical outcomes of a transcatheter interatrial shunt device for the treatment of heart failure with persevered ejection fraction in the reduce elevated left atrial pressure in patients with heart failure (REDUUCE LAP-HF I) Trial*, showed that creating interatrial shunts with stent type structures in HFpEF patients reduced rehospitalizations rates from 0.63 in the control arm compared to 0.22 in the treatment arm.

It is likely that the ideal interatrial shunt sizes through the fossa ovalis that maximize safety and shunt impact is patient dependent, and may require shunt sizes ranging from 0 mm to 10 mm. On the lower end of shunt sizes (0-3 mm) the benefit in symptom relief may not be worth the risk of the shunt procedure, and this small of a shunt may close over time. Also, on the upper end there is a point beyond the 10 mm shunt size LAP plateau where bidirectional flow could be a risk. Also, when a shunt is naturally formed as an Atrial Septal Defect (ASD), it has been found that for larger ASD's over 15 mm it is advised to close the defect to avoid shortened life due to heart failure or high blood pressure. So it is of possible benefit for heart failure patients or PAH patients to benefit from shunts through the atrial septum, and preferably through the fossa ovalis, of diameters ranging from 3 mm to 10 mm.

Therefore, it would be desirable to have a medical device that is capable of creating an incision or an opening in the interatrial septum of the heart to alleviate pressure between chambers in the heart that does not suffer from the limitations of prior devices or procedures. It would be advantageous to have a catheter that can create various slits, openings, or apertures in the interatrial septum in a predetermined orientation. It would also be advantageous to have a catheter that may be easily manipulated to remove a section of the interatrial septum to form a permanent aperture that is less likely to spontaneously close.

BRIEF SUMMARY OF THE INVENTION

The present invention solves these needs by providing a medical device that creates a hole in the interatrial septum and/or removes tissue as needed. In one embodiment a septostomy assembly includes a catheter assembly with a catheter shaft having a catheter lumen and a shaped blade with a cutting edge oriented at a substantially right angle to the longitudinal axis of the catheter. The assembly also includes a tissue retention assembly located at least partially in the catheter lumen, the assembly including a shaft, a proximal tissue retention device and a distal tissue retention device, the tissue retention devices configured to apply a force between them. The system also includes an actuator configured to reduce a gap between the proximal and distal tissue retention devices to grasp a tissue. The proximal tissue retention device and the distal tissue retention device apply the majority of the force at their perimeter.

In another embodiment a proximal tissue retention device and the distal tissue retention device apply at least 60% of the force, and up to 90% of the force between them at their perimeter. In one embodiment the proximal tissue retention device is configured to exit the catheter lumen, and further has a first cross sectional area that fits within the catheter lumen, and a second, larger cross sectional area when it exits the catheter lumen. The proximal tissue retention device grasps the tissue while the proximal tissue retention device is in the second, larger cross sectional area configuration.

In one embodiment the proximal tissue retention device is configured to reduce its cross sectional area while still grasping the tissue, but is configured to retain the same cross sectional area of tissue while reducing its cross sectional area. In a preferred embodiment there is a raised edge part on the perimeter of the proximal capture mechanism. In another, there is a tissue retaining mechanism at the perimeter of the tissue capture mechanism. In one embodiment there is a locking mechanism configured to hold the force on the tissue between the proximal and distal tissue retention devices. In another, there is a spring loaded capture mechanism for maintaining the capture force within a set range regardless of the thickness of the tissue captured.

In one embodiment the tissue retention assembly comprises a proximal tissue capture shaft in the catheter lumen. The proximal tissue capture shaft is operatively attached to the proximal tissue capture device. In a refinement of this embodiment, the tissue retention assembly further includes a distal tissue capture shaft inside the proximal tissue capture shaft, the distal tissue capture shaft operatively attached to the distal tissue capture device.

In an embodiment the outer diameter of the proximal tissue retention device is close fitting to the inner diameter of the shaped blade. In another embodiment the distal tissue retention device further comprises a tissue trap. In some embodiments the system includes a marker to identify the catheter location on a visualization system. In some embodiment the system includes a means for rotating the shaped blade. In others, it may have a tissue debulking mechanism.

In one embodiment the septostomy assembly includes a catheter assembly, the catheter assembly with a catheter shaft having a catheter central lumen, a shaped blade with a cutting edge that is oriented at a substantially right angle to the longitudinal axis of the catheter; and a tissue retention assembly located at least partially in the catheter central lumen comprising a shaft, a proximal tissue retention device and a distal tissue retention device, the tissue retention devices configured to apply a force between them. The assembly further includes an actuator configured to reduce a gap between the proximal and distal tissue retention devices to grasp a tissue. The proximal tissue retention device and the distal tissue retention device are each expandable from a first cross section that fits within the catheter central lumen to a second expanded cross section that exceeds the diameter of the catheter.

Also disclosed is a method of treating a heart comprising the steps of (1) inserting a catheter as disclosed above into the right atrium of the heart, (2) while the catheter is in the right atrium, moving a portion of the device into the left atrium, (3) expanding the proximal tissue retention device to the expanded cross section, (4) expanding the distal tissue retention device to the expanded cross section, (5) actuating the actuator to grasp the tissue retention devices in place with a portion of the interatrial septum held between them, (6) cutting an aperture in the interatrial septum between the right atrium and the left atrium, and (7) removing a cut tissue from the right atrium.

BRIEF DESCRIPTION OF THE DRAWINGS

FIG. 7 is a partial perspective view of an expanded proximal capture mechanism;

FIG. 8a is a partial perspective view of a collapsed proximal capture mechanism;

DETAILED DESCRIPTION OF THE PREFERRED EMBODIMENTS

Figure 1:
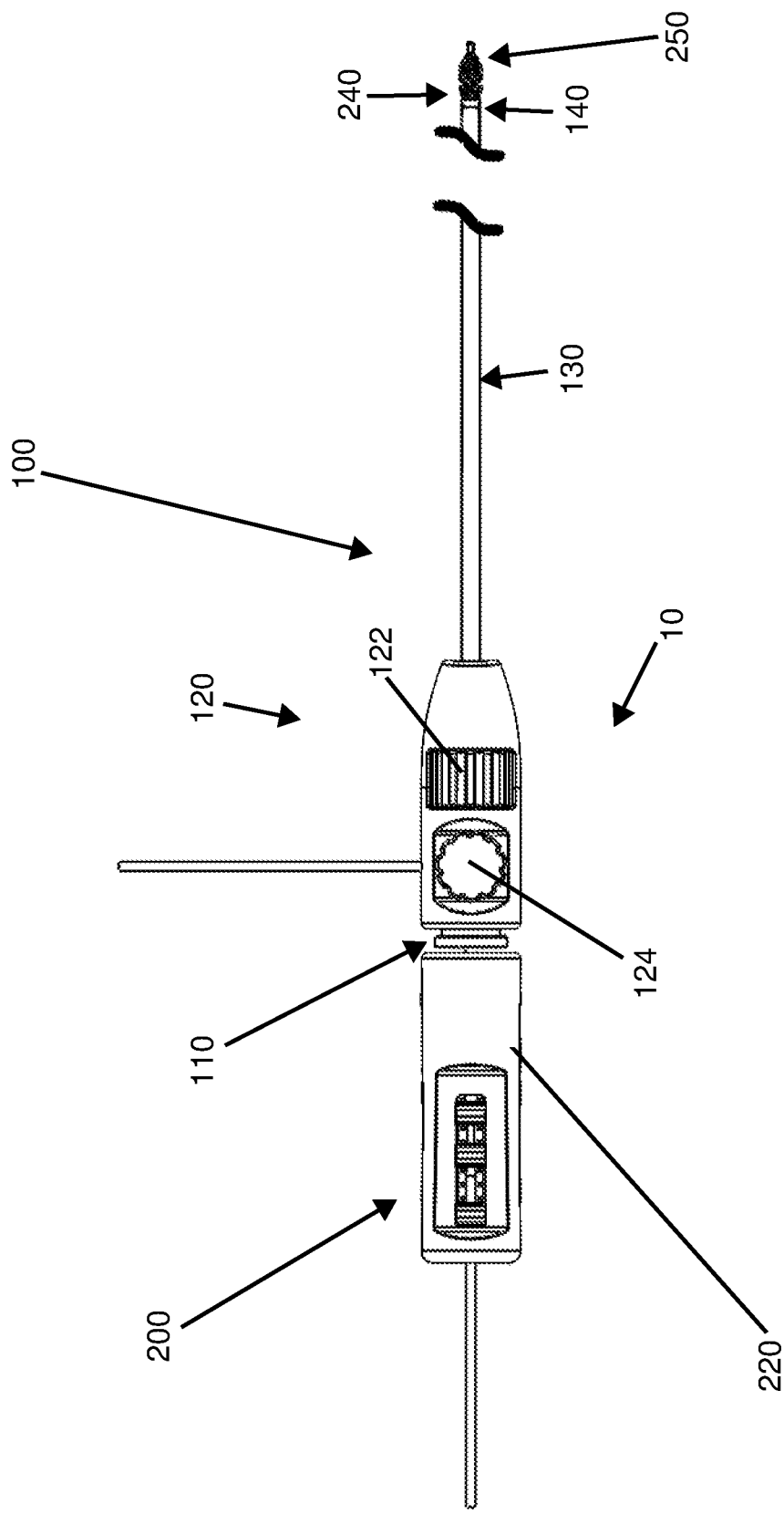
FIG. 1 is a partial perspective view of a septostomy system constructed according to the present disclosure.

In general, the invention comprises a medical procedure and corresponding septostomy devices for therapeutic surgical procedures. In particular, the invention comprises a method of creating an aperture between heart chambers for blood flow and devices for creating that aperture. In this context, an aperture creates a space or gap large enough to allow significant blood flow between the two chambers it connects, to treat or improve heart failure, pulmonary hypertension, or similar diseases, without the use of an implanted device.

In order to treat any heart disease it must first be diagnosed. As an example, for congestive heart failure diagnosis may comprise listening to the lungs for signs of congestion, measurement of vital signs, a chest x-ray of the lungs, electrocardiogram (ECG), an echocardiography and other imaging modalities to assess cardiac output, ventricular contraction and filling, atrial size, and cardiac valve function, etc., insertion of a central venous catheter and measurement of pulmonary capillary wedge pressure (PCWP), blood tests, e.g., to check for chemicals such as brain natriuretic peptide (BNP and N-terminal pro-B-type natriuretic peptide (NT-proBNP), a stress test, cardiac catheterization and/or an MRI or CT scan. In addition, transthoracic echocardiography (TTE) or transeophogeal echocardiography (TEE) may be used to confirm the absence of any current holes between the chambers of the heart.

Once congestive heart failure is diagnosed a course of treatment will be designed. While it is possible to treat congestive heart failure with surgery, implants, or other methods, herein disclosed is a method of advantageously treating congestive heart failure without surgery and without leaving behind an implant.

The disclosed procedure preferably begins with a percutaneous entry into a vein, preferably the femoral vein in the groin region. It is also possible to gain entry via a jugular or subclavian vein or neck vein. Typically this introduction is initiated by placing a needle through the patient's skin and into the vein. Then a guidewire is placed thru the needle and run up into the vein. Over this guidewire a combination introducer sheath and dilator is inserted into the vein.

The introducer sheath must have an inside diameter to accommodate the outer diameter of the septostomy system. With the introducer sheath in place in the vein the guidewire is advanced up the IVC and into the right atrium (RA) of the heart. The septostomy system may be introduced into the RA as a single element, as an assembly, or in partial assemblies.

In one partial assembly embodiment an outer catheter torque shaft with cutting blade may be mounted to a dilator. This combination is placed through the introducer and advanced into the RA. The tapered dilator tip makes the advancement of the combination easy and safe. Depending on the embodiment, the blade may have a blade protecting cover over it. In another embodiment the blade has the sharp edge on its inner diameter and the inside diameter is close fitting with the outer diameter of the dilator or dilator shaft, and thus the patient is protected from the sharp blade. Other elements may protect the tissue or the blade, including the tissue removal elements.

Once the blade reaches the desired location, e.g., the RA, the introducer can be retracted, leaving the blade on the torque shaft in the RA. If not already present, the tissue capture components are inserted into the inside of the torque shaft and blade. The blade with torque shaft and tissue capture system can also be introduced into the RA as a single element or as a combined assembly with or without the use of a dilator. There are multiple ways of facilitating the latter. First, the cutter shaft can have a movable tapered outer sheath protecting the cutter and capture mechanism, which can be withdrawn once the RA is reached. Alternatively, a distal capture mechanism may have a conical shape to it (tapered balloon, tapered slotted tube, tapered braided tube, etc.) taking the place of the tapered introducer. Finally, the need for a hard taper introducer can be minimized by using an expandable introducer seal (preferably not a hard silicone seal). The sheath used in the present invention may be steerable, for example controlled by pull wires which extend from its distal region to a handle at its proximal end, the handle having one or more actuators. Likewise the sheath may be pre-curved or pre-bent such that it will automatically orient towards the interatrial septum once it reaches the right atrium. The sheath may be magnetically or robotically steerable.

Once in the right atrium, the physician will identify the portion of the interatrial septum at which he will create the interatrial aperture. Typically, this will be at the fossa ovalis. However, if the physician needs to create the interatrial aperture at a location other than the fossa ovalis, the issues discussed herein with regard to the need to capture thicker tissue into a smaller catheter will be even more pronounced, and the methods disclosed herein will be more necessary.

Because the fossa ovalis is thinner than the remainder of the interatrial septum, it would be easiest to cut an aperture at its location. To identify the fossa ovalis the physician may employ one or more means of tissue thickness sensing. For example the physician may use an electrode and test for impedance changes, may employ one or more ultrasound methods, or may simply test for tenting. For example, the physician may apply a small amount of pressure to the interatrial septum and search for tenting in the tissue. Once the physician locates the spot where the tissue easily tents, e.g. the fossa ovalis, the physician will deploy the present device to create the aperture.

The system may need to cut through, and capture fossa ovalis tissue which is known to be between 0.5-4 millimeters thick in most patients. In some patients, especially those who have had prior crossings in other procedures, this tissue may also be relatively fibrosed, e.g., due to multiple transseptal crossings from left sided structural heart or electrophysiology surgical procedures. So the fossa ovalis tissue to be removed by the catheter may be slightly larger than 10 mm in diameter, up to approximately 4 mm thick, and relatively fibrosed and incompressible in nature. Folding this tissue in any direction will not yield a tissue cross section small enough to fit within to inside diameter of preferred catheter constructions. As an example, safely and repeatably capturing, cutting and extracting tissue 3 mm thick and 8 mm in diameter from the human body will require a modification to the tissue in order to reduce its cross-sectional area sufficiently to be pull it into a 12 French catheter. Technical means for debulking or reducing the tissue cross sectional area are discussed herein, and include, but are not limited to, stretching it, compressing it, desiccating it, vaporizing it, and cutting or grinding it into pieces prior to extraction. Technical means for capturing and cutting tissue to create a shunt at a diameter larger than the catheter diameter include, but are not limited to, expandable capture components, expandable cutter components, and components to contract captured fossa ovalis tissue in diameter prior to or after cutting it.

When it is desirable to cross into the left atrium the physician will create a small puncture in the septum using a transseptal device. In some embodiments a guidewire is used to first cross the septum. Guidewire crossing of the atrial septum may be facilitated by a crossing needle like a BRK™ transseptal puncture needle, a Baylis Medical RFG™ transseptal kit, a brockenbrough needle, or another transseptal device may be used for crossing the septum into the left atrium. Alternatively the expandable distal capture component may have a needle type distal tip, an RF electrode on the distal tip, or a similar distal tip to facilitate easy atrial septum crossing without the use of a preplaced guidewire. Once crossed, a guidewire may be threaded through the interatrial septum puncture and the distal end of the guidewire may be left in the left atrium. The proximal end of the guidewire will remain outside of the body, with its entry point at the femoral vein. As with the sheath, the guidewires described herein may be pre-curved or pre-bent such that they will automatically orient towards the interatrial septum once reaching the right atrium.

Depending on the therapeutic catheter that will be used in the latter portion of this procedure it is possible that a guidewire may not be required, and in some cases that the device may not cross into the left atrium at all. In such instances a transseptal device may not be necessary either. If the catheter to be used to form the interatrial aperture is designed to create its own transseptal crossing or create an aperture without crossing the septum, the guidewire or transseptal device may be avoided, potentially saving cost and time.

Either way if the catheter is to cross the septum it is helpful for the expandable distal capture component to have certain features, such as one or more of a reduced cross section, expandability, a tapered tip and a lubricious coating. Likewise, to facilitate low force crossing of the septum it is important for the expandable distal capture component to have a low profile. Having a low profile minimizes tissue tearing, which improves accuracy of shunt shape and size. As an example of this, if the distal capture component was not expandable, but instead a tapered shape like a dilator, the tissue will tear or expand when being crossed such that the subsequent capture of tissue can be less than ideal. Portions of the tissue may escape cutting and capture, which can lead to multiple problems. First a tissue portion that has stretched outside or partially outside the range of the cutter may not then be cut and removed. Over time that stretched or torn tissue may heal, prematurely healing the aperture. Second, such a stretched or torn tissue may come loose, either during the procedure or at a later date, causing a stroke or another complication. This distal capture component must also provide high capture forces when it is expanded, for accurate shunt size and shape. Furthermore, for safety reasons the expandable distal capture mechanism failure mode defaults to open. This means the device is ideally naturally self-expanding after it exits a flexible retention tube, or similar method of holding it in a reduced profile. Finally, the capture mechanisms must ideally place most of the capture forces at the outer circumference of the captured area.

During the procedure the physician will monitor the location of the catheter and/or sheath as well as the progress of the cut, the nature of the aperture, or other procedure details via fluoroscopy, MRI, ultrasound, or transesophageal echocardiography, intracardiac echocardiography (ICE) or similar tracking or visualization technology for guidance. Toward this end, it is preferred that the catheter includes visualization markers, such as radiopaque or ultrasound markers as described in further detail below. Likewise, the physician may monitor the location of the catheter and/or sheath as well as the progress of the cut, the nature of the aperture, or other procedure details via a camera, such as a CCD camera. In the latter case it may be advantageous to apply a hood over the operation region, empty the hood of blood and replace it with saline, such that the procedure may be visually monitored. This hood may also be used, as discussed in detail in the incorporated priority documents, to provide an orthogonal orientation to the cutting blade and the target tissue. Other location systems are possible, including MRI, electroanatomical navigation systems such as EnSite®, Carto®, or MediGuide® systems, along with the corresponding sensors on the introducer and catheter.

The interatrial aperture will be created by one of two mechanisms or a combination thereof. First the surgical catheter will create an aperture. The catheter could use a cutting blade or other means disclosed herein to create an aperture or cut pattern in the interatrial septum such that a sufficient flow of blood may occur between the two atria. The catheter may create a circular or semi-circular hole in the septum. Such openings may have benefit in determining the direction of blood flow in order to maximize left-to-right and minimize right to left flow especially in patients with combined left and right heart failure as occurs in patients with HFrEF. Similarly, an elongated hole such as a 1 mm wide slit with radiused ends may have low cross sectional area and shunting with low pressure differential and increased csa and shunting with higher pressure differential. The utility of such a design may have particular value with HFrEF patients.

Second the catheter may remove tissue. For example in creating a shaped aperture the catheter may utilize a cutting blade to cut the tissue from the septum and remove it from the body. Loose tissue removal is critical so that any loose tissue does not remain in the atria, creating a substantial risk of stroke due to embolization.

In either mechanism, the physician preferably engages the target tissue with a distal portion of the device, such as a tissue capture mechanism. The tissue capture mechanism may penetrate into or through the tissue, and then be actuated (e.g., via an actuator on the catheter or sheath handle) to hold the tissue and bring it to the cutting blade. Alternatively, the tissue capture mechanism may hold the tissue and the blade may approach it for cutting the tissue.

Thus, the tissue capture mechanism works with the blade for one or more purposes, it may hold the tissue in place, guide the blade to the desired portion of the tissue, hold the catheter in place and on target, retain any loose tissue, or create an initial opening in the tissue for the device to pass into.

In a preferred embodiment the tissue capture mechanism or a portion of the tissue capture mechanism passes through the tissue as the system is advanced. Alternatively, an actuator, (e.g., an actuator on a handle, or simply a movable lumen/guide within the medical device) may be in or moved to a first position that advances or locates the tissue capture mechanism forward away from the cutting blade. This advancement (or a separate advancement) may push the relevant distal component through the tissue. Once in place, either by actuation or mere advancement, the actuator is activated to a second position that causes the distal tissue capture mechanism to engage the tissue. The second position (or a third position) may also pull the tissue into a lumen or a tissue capture portion in the catheter or sheath, tenting it so that a larger aperture may be cut. The tissue may be pulled into the lumen or portion by an actuator, manually by withdrawing a portion of the system, or by movement of a portion of the capture mechanism.

In one embodiment the distal tissue capture mechanism is expandable. Once the expandable distal capture component has crossed the atrial septum it can be expanded. This may be accomplished a variety of ways, such as a bias toward the expanded position by actuating an actuator component on the handle of the catheter, or both. The actuator may be a knob, lever, trigger, etc., which releases a preshaped expandable distal tissue capture mechanism to expand, or forces the expansion of an expandable component into the desired shape. Ideally the expandable distal tissue capture mechanism is rigid, so when it is brought together with a proximal tissue capture mechanism, a high capture force can be placed on the tissue so the tissue does not easily pull out due to movements by the catheter, causing imperfect shunt size and shapes. The high capture force from the distal capture mechanism is preferably placed at the outer circumference, toward the proximal tissue capture mechanism, tightly pinching the tissue between the tissue capture mechanisms. One or both distal and proximal capture mechanisms have raised circumferential edges, or barbs, which are the components that first touch the tissue and place most of the capture force on the tissue. The distal tissue capture mechanism also holds high loading forces perpendicular to the capture, so when there is an in plane side load on the catheter the captured tissue does not pull out of the tissue capture mechanism. The expandable distal capture mechanism traps all small tissue particulate to keep it from floating into the blood stream during the procedure, e.g., through a very fine layer of mesh, braid, or solid material.

The tissue capture mechanism can capture the tissue by applying a preset force to hold the tissue. This preset force may be set by the physician. In one embodiment the physician sets the force before the procedure by adjusting the device. In another embodiment the device has settings or markings that allow the physician to control or adjust the degree of force, either pre procedure or during the procedure. In another embodiment the preset force is set during device manufacture. Alternatively the device may set a prescribed distance between or gap for the distal and proximal tissue capture mechanisms.

Ideally, the proximal and distal tissue capture mechanisms cooperate to capture the tissue without stretching it prior to capture and this is ideally done by capturing the tissue between them without moving the tissue substantially out of its original plane or location. Thus, in one embodiment the distal tissue capture mechanism is first adjusted to the position of the distal side of the tissue, that is its grabbing surfaces in minimal contact with the tissue, and then the proximal side is brought to the proximal side of the tissue. These adjustments may be made by moving a shaft connected to the respective tissue capture mechanism. The adjustments may also be made via an actuator. They may be manually controlled by the physician, or automatically controlled via a robotic or magnetic control system, for example. The two devices may be structured such that as they exit a retaining tube or catheter, they automatically expand. Thus, as the catheter passes through the septum in to the LA, it has a low profile. A first portion of the catheter e.g., an outer sheath, catheter, or tube, is then withdrawn or a portion is advanced out of it, allowing the proximal or the distal tissue capture mechanism or both to expand. This mechanism is pulled or relocated to the surface of the tissue. The first catheter portion is then withdrawn further, while the proximal tissue capture mechanism remains in place. As the first catheter portion withdraws, the other tissue capture mechanism may exit and likewise expand, manually or automatically putting a clamp on the tissue, e.g., by their spacing from the each other or by actuation.

In addition, it is preferred that the capture mechanisms work to capture the tissue in its natural orientation, that is, not twisting or bending the tissue out of plane. Before the expanded distal tissue capture mechanism is pulled proximal to capture tissue it is preferred that the catheter is aligned to trap the tissue in its natural orientation. First, the proximal tissue capture mechanism, as seen on fluoro or echo is advanced such that the most distal face of the proximal tissue capture mechanism is touching the fossa ovalis in its natural plane. To improve visibility of the proximal tissue capture mechanism radiopaque and/or echolucent filler is added. This will allow an in plane capture and support the accurate shunt shape and size.

The proximal and distal tissue capture mechanism can be fabricated from a single, or joining of two elastic, material(s) such as nitinol and retained for delivery. In such a form once the retained distal capture mechanism crosses the tissue, such as the septum, it may be released prior to, or in conjunction with, the proximal tissue capture mechanism. The preformed shape and elastic nature of the material acts as an actuator and locking mechanism bringing the proximal and distal capture components in contact with the tissue to be capture with a prescribed capture force. In addition to the natural shape of the material, an actuator may be used to hold the material in shape, such as by drawing the proximal and distal ends closer together to lock them in a rigid, open position. Likewise the ends may be drawn together by multiple catheter shafts.

To optimize the shunt shape and size it is important to minimize the movement of the tissue capture point after device alignment, during capture and during cutting. This can be done by fixating the catheter at any point from proximal to distal. This is especially important after the catheter alignment just prior to capture. However, movement of the catheter after capture can still cause improper shunt shape and size if the loading force on the fossa ovalis tissue is sufficient to pull tissue from the capture point. Fixation of the catheter should control torque, advancement and withdrawal of the catheter relative to the catheter distal tip. The most efficient and safe way of performing this catheter fixation is to as solidly as possible attach the catheter outside the puncture site to the patient. One way to do this is to adhesively attach a catheter hub to the patient as close to the puncture site as possible. This catheter hub can securely grasp the catheter shaft or the catheter handle. If the patient moves the catheter hub and catheter will move with the patient, but the relative movement of the catheter distal tip with respect to the fossa ovalis will remain fixed. Alternatively, since the patient is sedated and generally does not move during the procedure, the proximal catheter shaft or handle can be fixed to the bedrail or similar, to fixate it and keep it from moving. To facilitate the latter the patient's leg can furthermore be fixated to the bedrail to keep movements minimized. The catheter can also be fixated by first fixating the introducer sheath with means already described, and then using a means to fixate the catheter shaft or handle to the introducer sheath.

After the catheter is fixated any remaining in-plane or longitudinal bias must be removed. The in-plane bias is a result of the catheter at the fossa ovalis crossing point being biased in-plane such that it slightly elongates the hole in the tissue which it is crossing through, as evidenced by high velocity blood jetting on doppler (TEE,TTE,ICE). The catheter shaft is aligned in the fossa ovalis plane such that jetting as seen on doppler is minimized. This is done by torqueing the catheter shaft, and if not preshaped, also actuating pull wires to deflect the distal tip. By minimizing blood jetting alongside the catheter the shaft is brought into its original crossing point and in plane catheter shaft bias is removed. This will allow for a more accurate shunt shape and size.

Once the capture is completed using the capture actuator on the handle it is preferred, for safety and performance reasons, to not easily allow the capture to be released. For this reason a locking mechanism is preferably placed in the handle or in another part of the catheter so once the tissue capture is performed it is difficult to inadvertently release the tissue, or in some embodiments to release it without taking multiple steps. This will minimize any potential loss of cut tissue. To maximize accuracy of the shunt shape and size, as well as optimize safety, it is important to not allow any tissue to slip out of the capture system. While pressure can be evenly applied across the face of the tissue, it is ideal place all capture forces at the outer circumference of the capture mechanisms. Doing so prevents any captured tissue edge from slipping out of the capture mechanism. This may be accomplished by having an outer raised knife like edge on the outer most perimeter of the distal portion of the proximal capture mechanism and something similar or complimentary on the proximal side of the distal capture mechanism, or vice versa. The diameter of these raised edge parts of the capture mechanisms should be just slightly less than the cutter blade. Also, to further improve capture teeth may be located on the raised edge. To maximize capture forces, without going beyond the strength of the catheter component, it is ideal to make the capture system spring loaded so a set range of capture forces will be obtained no matter the tissue thickness.

In one embodiment the physician will move the capture point slightly into the LA or the RA once the tissue is captured. For example, the catheter can have a component which, while activated, can move the capture point slightly into the LA, in a controlled manner. Alternatively, the physician can move the catheter, or an attachment point outside the body can be activated to move the entire catheter forward. This movement has two intended purposes. First, by moving the capture point slightly into the LA, the tissue is pulled slightly tight and over the blade, which helps facilitate an efficient cut by helping to hold the tissue against the sharp edge of the cutter blade. Secondly, if the tissue is tented slightly into the LA prior to cutting, as seen on fluoroscopy or echocardiography, the clinician will know when the cut is complete by watching for the tissue to collapse from its tented position to its natural plane. This tenting of tissue is only expected to require a few millimeters of movement of the capture point. The amount of advancement is preferably indicated on the catheter or its handle. This advancement or tenting into the LA is expected to be less than 1 cm. The advancement mechanism can also be used for final fine adjustment of the linear capture point just before cutting the tissue.

Another design embodiment to facilitate tissue cutting is to have a waist on the proximal end of the distal capture mechanism that is slightly larger than the diameter of the blade during cutting. This waist, in combination with the capture mechanism holds the tissue against the blade during cutting. In some embodiments the waist provides rigidity to the structure, in others it can provide a pocket or channel, possibly in combination with the capture mechanism, for the blade to work into as it cuts the tissue.

Once the mechanism is in place, the physician will move the tissue capture mechanism(s) or the cutting edge to create a durable interatrial shunt. In one embodiment the cutting blade is a shaped, e.g., circular blade. The shaped blade, even when very sharp, is relatively safe. In an embodiment with no points on the blade, cutting the tissue requires significant force and/or slicing motion. In the preferred embodiment both force into the tissue and a slicing motion is applied. It is important to not have the blade move forward into the tissue without the appropriate amount of slicing or blade rotation. If there is too much forward motion relative to blade rotation and slicing, the forward motion may pull tissue out of the capture mechanism, either keeping the blade from effectively cutting or cutting the shunt with the wrong size or shape. To facilitate the precise forward travel of the blade into the tissue relative to the blades rotation a threaded component is used, so only one actuator controls advancement and rotation of the blade in precise coordination. The threaded component may be located anywhere in the catheter from the distal end to the handle. However, the preferred embodiment has the threaded component near or in the distal end of the catheter. There is also a blade stop incorporated into the catheter to keep the blade from advancing to far beyond the capture system and causing a safety issue. An indicator may show how far the blade has been advanced beyond the capture point and into the tissue.

This same basic catheter design may be implemented by energizing the metal cutting blade with RF cutting energy (or laser), such as that from a Valley Labs (™) generator. In this application blade rotation or tissue slicing is not necessary. However, blade advancement must be coordinated with the application of RF energy. In addition, it is preferred that the RF energy be focused on the tissue. As such, if a shaped blade is used, e.g., circular shaped blade 140, the majority of the blade may be coated to reduce the portion that emits RF energy. For example, the shaped blade may be coated with an insulator from the proximal portion to just short of the distal portion, leaving only the distal circular edge uncoated and available to emit RF energy into the tissue. The blade may be blunt in this scenario. While a sharper blade may work with the RF to penetrate, it is not necessary in other embodiments. In addition, the blade may be in electrically isolated portions, such that one portion may be energized at a time, with each portion being on a different electrical pole. When using an RF blade, it may be advantageous to have the return electrode be a patch on the outside of the body. It may be preferred that the return electrode be on the catheter. For example, the distal tissue capture mechanism may include one or more return electrodes. The outer edge of the distal tissue capture mechanism may serve as return electrodes, providing a very controlled path for the RF energy. If the return electrodes are divided into electrically isolated portions, the device may have the ability to sequentially direct the RF energy from one portion of the blade to different portions of the return, or to target a specific portion of the tissue 30.

The guidewire, a navigation electrode, or an electrode on the shaft for the distal tissue capture mechanism are all locations for potential return electrodes.

In one embodiment the blade locks into the advanced position and acts as a capture component, keeping tissue from releasing as the catheter is retracted by holding the tissue, and all or part of the distal and proximal tissue capture components inside a cavity in the blade. With the blade locked in the advanced position the blade could cut into tissue if the system is advanced during the catheter retraction processes. To protect against the accidental cutting the expandable distal capture mechanism or a related catheter is sufficiently long so it protects tissue from unintended cutting from the blade. In either case, the distal most portion is atraumatic, and will not perforate the heart wall. In addition, the outside diameter (OD) of the distal capture mechanism preferably has a nominally open OD which is close to the inside diameter (ID) or cutting edge of the blade, making unintended cutting unlikely. It can have this closely dimensioned OD when it is fully open, or during the withdrawal into the capture housing.

For proper utility in patients who need transseptal shunting of blood it is critical that the aperture be "durable" such that it will stay open for a long period of time and even permanently, as defined below. The shunt size can be titrated by measuring the left atrial pressure either at rest or with exercise. Likewise, the doctor can measure oxygen saturation in the right atrium, or cardiac output. The medical device of the present invention preferably includes means to measure pressure and/or oxygen saturation, such as a sensor or via fluid removal for testing.

In one version of the procedure, the device or a complementary device/device portion crosses the septum into the left atrium and records the resting blood pressure in the left atrium (or with exercise). At this point the durable aperture is cut as detailed elsewhere. Then, the pressure measurement is again performed and it is determined if the aperture is sufficient. One advantage of the present procedure and device is the ability to measure success during the procedure, and adjust the shunt size as needed, by cutting more tissue from the septum, rather than waiting until post procedure and having to reenter the patient.

In certain patients it is preferred that the hole be at least 3 to 12 mm, preferably 4 to 10 mm, or 6 to 8 mm, in diameter for the desired clinical benefit. In one preferred embodiment the shunt ranges from 8-9 mm. In other patients a higher pressure may indicate that a smaller or larger aperture be formed, e.g., 0.5 to 5 mm, or 2-3 mm. However, such small hole sizes have increased risks of closing, tissue healing, and plugging, and are accordingly unlikely to be a durable aperture absent exceptional circumstances. The interatrial shunt lowers LA pressure especially during exercise in heart failure patients. The left-to-right shunting can cause a slight decrease in left ventricular (LV) CO and an increase in right ventricular CO. The reduction in LA pressure, however, might allow patients to achieve a higher level of exertion leading to higher heart rate and thus an increase in LV CO. Furthermore, increases in RA pressure and pulmonary arterial pressure can occur, but in HF patients, despite the increase in RV CO, a reduction in pulmonary venous pressure can actually occur. The size of the shunt can determine the extent of all these hemodynamic effects, and enable a Qp/Qs ratio sufficient to reduce LA pressure without RV overload. The clinically necessary size will vary from patient to patient. Subsequent to the procedure the physician will monitor the patient at one month, three-month, and six-month exams to determine if the size of the hole has shrunk. While it is anticipated that healing tissue may slightly shrink the aperture on the order of 0 to 2 mm, if the aperture remains open at six months it is considered "permanent" or durable for purposes herein. It is also desirable that the aperture be visible on an echocardiogram so that it can be readily measured. Ultimately, for these patients, safety and a proper balance of blood hemodynamics, oxygenation will be used determine the aperture size, shape and quantity.

The tissue may be removed by a device using, for example, suction or grasping mechanisms. As disclosed in detail below, the device may require technical means for reducing the tissue cross sectional area. These would include, but are not limited to, stretching the tissue, compressing it, desiccating it, vaporizing it, and cutting or grinding it into pieces prior to extraction. Technical means for capturing and cutting tissue shunt at a diameter larger than the catheter diameter include, but are not limited to, expandable capture components, expandable cutter components, and components to contract captured fossa ovalis tissue in diameter prior to cutting it.

In a preferred embodiment the catheter, e.g., the tissue capture mechanism, will pull the tissue into the blade to positively retain it and keep it from releasing into the heart. In addition to their potential utility for tissue removal, suction and grasping mechanisms may also be extremely useful for positioning the device, and retaining the device in the desired position during operation. Additionally, suction may aid in determining that the blade is orthogonal to the tissue, e.g., that it has the proper orientation for cutting. For example, if under light suction in the blade's lumen a seal is formed between the blade and the tissue, the blade may be determined to be at a proper orientation to the tissue for cutting a durable aperture. Likewise, sensors on the tissue capture mechanism or on a grasping mechanism may be able to determine how far into the tissue the grasping mechanism is. If four hooks, for example, all 90 degrees apart, have penetrated the tissue to the same depth, it may be determined that the device is orthogonal to the tissue. If the tissue capture mechanism is in tissue contact at four points 90 degrees apart, it likewise may be determined to be in orthogonal contact.

Creating a hole in the heart without leaving behind an implant avoids the need for anticoagulant therapy, lowers the risk of infection, and avoids the use of an implant that may come loose over time. In addition the procedure is substantially simpler than installing and leaving behind an implant. Due to the lack of an implant, there are no risks of MRI compatibility, no risk of device failure or fracture. It is easier to close the aperture if needed absent a device, and the overall total cost of care is lower. No implant means faster and safer crossing of the septum during future catheter based surgical procedures, such as treating atrial fibrillation or ventricular tachycardia. Finally, the procedure is faster and will allow for a more efficient use of hospital facilities and physician time.

There are multiple ways to determine if the aperture is large enough to be efficacious. Subsequent to the procedure the physician may do so by, e.g., examining the aperture on an echocardiogram visually and using doppler, calculating the degree of shunting, performing an exercise tolerance procedure, by measuring the ejection fraction, by measuring the wedge pressure, oxygen saturation, or other means. It is preferred that a clinical evaluation be conducted such as a walking test, to determine the practical effect on the patient. The invention allows for easier adjustment of aperture size compared to similar solutions. In particular, if the aperture size is too small, an additional aperture may be created, or the existing aperture can be expanded. Because certain clinical evaluations can be performed immediately after the patient is first treated, it may be possible in many cases to leave the catheter in place during the evaluation, use the same catheter to create the second aperture or increase the size of the existing aperture, and thereby avoid a second procedure. This determination can be performed by having the patient exercise using upper body exercise devices and measuring the LA pressure prior to and during exercise. If the reduction is not sufficient to reduce PCWP then a second hole can be created and the exercise evaluation repeated. This is not possible with the prior art devices.

The invention can be used to create shunts from other high pressure to low pressure regions with the potential of creating similar therapeutic benefits. An example of this is the creation of a shunt from the right atrium of the heart to the pulmonary artery. In this instance, there is an advantage over a shunt between the right and left atrium because a shunt between the right atrium and pulmonary artery does not waist oxygenated blood and has a lower risk of right sided blood entering the left side of the heart. Yet another way to create a decompression of the left side of the heart may be to create a shunt in a tricuspid leaflet. These are only possible examples of how a shunt creating catheter may be used in a minimally invasive way to prescriptively adjust pressures in the heart as a medical therapy.

Also disclosed is a medical device for creating the aperture between the left atrial chamber and the right atrial chamber. A preferred surgical device for creating an interatrial shunt has a means for firmly capturing interatrial tissue prior to cutting, cutting the shunt, and removing the cut interatrial tissue. The tissue cut using the devices disclosed herein have a diameter that is larger than the diameter of the device or the catheter shaft used to capture, cut and remove the tissue. Preferably, the septostomy device can includes the elements needed to capture interatrial tissue, cut shunts through that tissue, and remove the cut interatrial septum tissue—all with a catheter that has a smaller in diameter than the shunt it creates.

The medical devices have dimensional requirements depending on several factors. First, the length of the device will depend on its point of entry. For example, a catheter that will be used in a percutaneous entry at the femoral vein and which must reach to the right atrium will typically be at least 120 cm long and more preferably 140 cm. A catheter that will enter the body at a different location in many cases will be substantially shorter. The more lengthy and torturous the path the catheter must take, the stiffer the catheter body may need to be, and the more likely the catheter will be to require stiffening elements such as a stainless steel or nitinol braid. The need for a stiffer catheter is particularly acute for the present device. It must first take a long path through the body to the right atrium, then turn at a sharp angle to address the interatrial septum, and then project enough force along that turn to push the cutter through the interatrial septum. It is difficult to project that force along the length of the catheter body, which runs from the groin region to the heart, and then successfully get the force to take the turn toward the septum without first pushing the catheter higher inside the heart rather than to the side toward the septum. Accordingly, unlike many prior art surgical catheters, the present device may require a substantially stiffer body, provided by braiding, nitinol stiffening devices, or multiple catheter layers. A stiff catheter would also, in combination with ridged proximal handle/end fixation (bed rail), stiffness would allow the clinician to make fine (submillimeter) movements to the distal tip with respect to the tissue.

However, while a portion of the catheter or an introducer may need to be stiff, other portions may have other requirements. For example, the distal portion may require a high degree of torque response, or a high degree of column strength, but may be preferably relatively floppy. Likewise, in an embodiment with multiple catheters nested, one inside another (and likewise when an introducer is used) one device may have one set of criteria, such as a stiffer body—with, or in some cases without a high torque response—along the length of an introducer, or a stiffer body at a bend region that is designed to be within the heart to direct the catheter distal end toward the septum. A second catheter may then be relatively floppy, such that the septostomy system has one set of criteria in one region to deliver the functional elements to the atrial septum, while the system inside the atria—or even just at the septum—has a different structure. Thus, for example, the system may have a stiff body along its length through the venous system, but have a floppy distal end that allows the blade and the tissue capture mechanisms to orient themselves properly perpendicularly to the septum.

Typically a thinner catheter is preferred, so long as the cutting elements are sufficiently sized to create a large enough interatrial aperture. For example, it would be preferred to have a catheter shaft of 9 French or less, preferably a 7 French OD catheter with a 6 mm cutter diameter and a 9 mm tissue capture mechanism, such that a 9 mm shunt is created with a 7 French catheter diameter. However there is a trade-off between a small diameter device and the need to create a sufficiently sized interatrial aperture. Thus it may be advantageous to have a small diameter shaft for the bulk of the catheter length combined with a somewhat larger distal working end on the catheter, or an expandable distal working end that has a small diameter upon insertion to the vein and can be expanded once in the right atrium and then collapse back to a smaller diameter for removal through the vein. On the proximal end of the catheter it is advantageous to have an easily manipulable handle so that the physician can direct the catheter into its desired location and control the cutting device. It is also advantageous to have a hub outside the body to secure the system in place during portions of the procedure.

Disclosed in FIG. 1 is a Septostomy System 10 that creates a safe and repeatable shunt in the interatrial septum through the removal of tissue. The system 10 has a catheter shaft outer diameter smaller than shunt diameter that it creates. As depicted the septostomy system 10 is comprised of a cutter assembly 100 and a capture assembly 200. In some embodiments the septostomy system 10 comprises one shaft, one handle, and multiple distal components. While the system 10 is primarily described below as two assemblies, each embodiment could be constructed as a single assembly, or in other multiple assembly formats. In other embodiments the septostomy system 10 comprises multiple handle components and multiple catheter shafts. One or more handles may include fluid ports, vacuum ports, and electrical connections. Likewise, one portion of the septostomy system 10 may have multiple catheter shafts.

Figure 2:
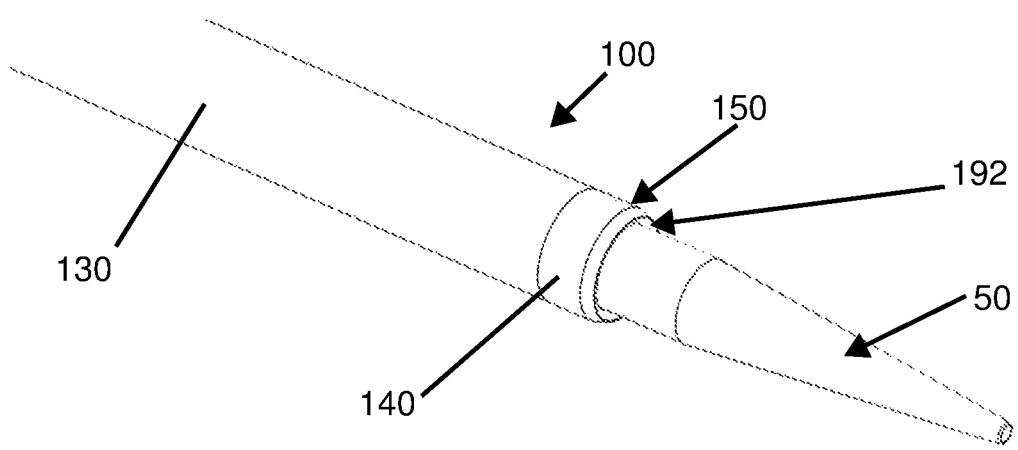
FIG. 2 is a partial perspective view of a distal end of the septostomy system.

As depicted in FIG. 2 the cutter assembly 100 may be initially delivered separately to the right atrium ("RA") over a dilator 50. With reference to FIGS. 1 and 2, the dilator is placed through the hemostasis valve 110 at the proximal end of cutter assembly 100, though cutter shaft handle 120, inside a lumen of outer cutter shaft 130 and exits at the distal end of cutter assembly 100 in the vicinity of cutter 140. Of course, in some embodiments dilator 50 is either not needed, or a dilator is incorporated into the cutter assembly 100 or the capture assembly 200. The cutter assembly 100 may be separated from the capture assembly 200 during this portion of the procedure, or they may be assembled and the dilator 50 is placed inside one or both portions of the septostomy system 10. Once the cutter assembly 100 is in place, either in the RA or the left atrium ("LA"), the dilator may be removed. Likewise, the cutter assembly 100 may be delivered to an atrium via an introducer (not shown) or any combination of an introducer, dilator, and guidewire.

Figure 3:
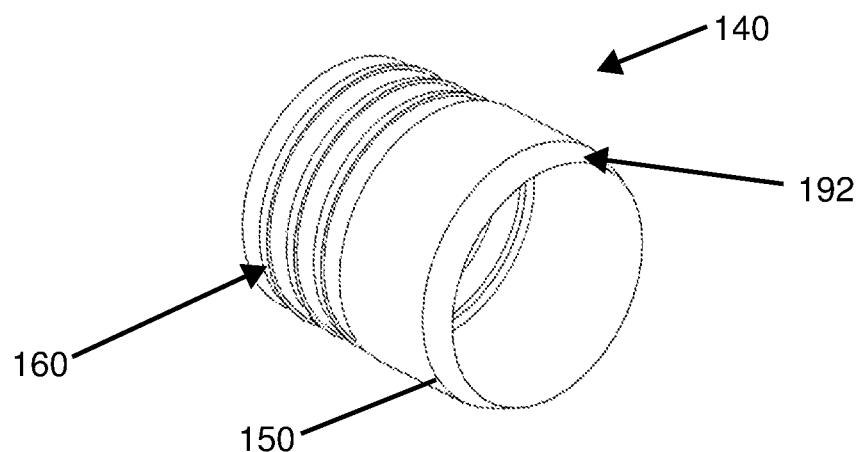
FIG. 3 is a partial perspective view of a blade for the septostomy system.

The distal end the cutter assembly 100 comprises a cutter 140. FIGS. 2 and 3 show how the sharp edge 150 of the cutter 140 on the outer cutter shaft 130 is protected during delivery from tissue (and vice versa) by the cutter edge's 150 close proximity to the tissue capture housing 192, which has a rounded, or not sharp, distal end. The tissue capture housing 192 is attached to one of the catheter shafts described below. In the alternative, the cutter 140 may be protected by close proximity to the dilator 50, in which case the dilator 50's OD would be only slightly smaller than the ID of the cutter 140.

Figure 4:
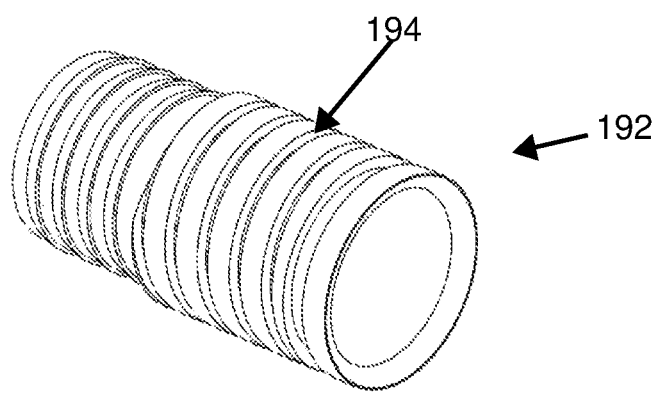
FIG. 4 is a partial perspective view of a tissue capture housing.
Figure 5:
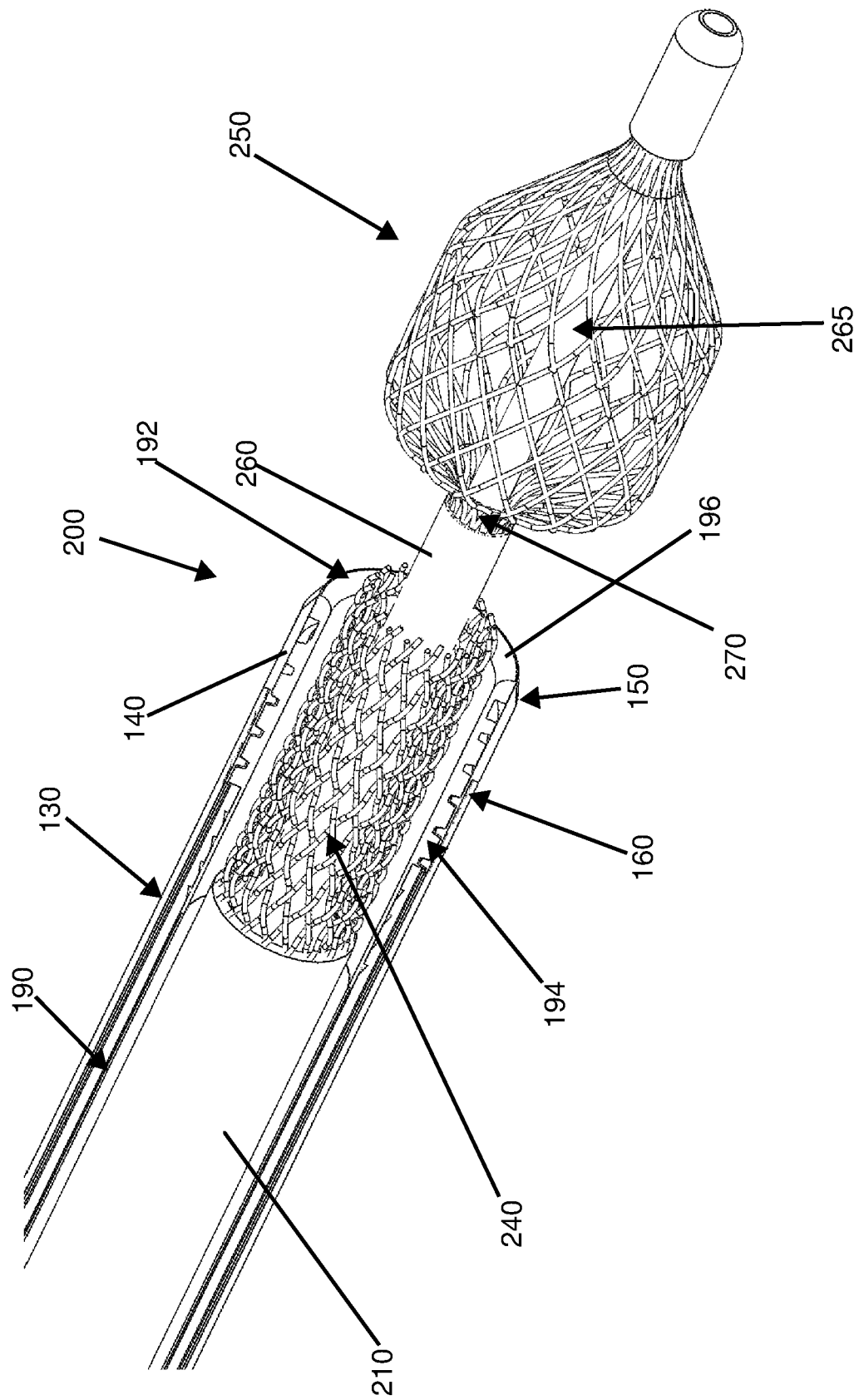
FIG. 5 is a partial perspective view of a septostomy system constructed according to the present disclosure.

In one embodiment, the tissue capture housing 192 is attached to an inner cutter shaft 190, as seen in FIG. 5. In this embodiment, both shafts are attached to the cutter shaft handle 120, as depicted in FIG. 2. The outer cutter shaft 130 may be 10 French to 30 French in outside diameter, is preferably approximately 80-150 cm in working length. In a preferred embodiment, the shaft is thin walled and may be between 0.005" and 0.020" thick to minimize the diameter of the catheter, may have a PTFE layer on the inside or outside or inside and outside to minimize the required torque force, has a degree of torque response which is close to 1:1 such the blade is precisely controlled, may have high column strength such that it can hold 2-4 lbs of force without buckling such that the blade is precisely controlled, and is relatively floppy such that it does not cause tissue injury. At the distal end of the outer cutter shaft is a cutter blade 140, as seen in FIG. 4, for creating the shunt. The cutter blade 140 is preferably made of tempered stainless steel or another suitable metal or material adapted to cut thin tissue. Blade 140 has a sharpened cutter edge 150 on its inside diameter. Blade 140 may have, for example, an inside diameter of 2-10 mm, preferably 4-8 mm. In one embodiment its ID is 6 mm and it has a thin walled circular shape. The proximal end of the cutter blade 140 is attached to the distal end of the outer cutter shaft 130. The cutter blade 140 is ideally 0.5-2 cm long and has a cutting edge 150 on the inside diameter, capable of cutting a 3-10 mm shunt. The cutter blade 140 may ideally have a threaded assembly 160 on its ID to control the slicing or advancement speed of the cutter blade 140 as it rotates, with the shaft, at a precise slicing angle to optimize cutting. Part of a threaded assembly 160 (FIG. 3) for advancing the blade when it is rotated may also be incorporated anywhere on the inner and outer shaft assemblies 190, 130, such as between the cutter blade 140 and tissue capture mechanism housing 192 or the dilator 50. The blade 140 may be serrated, adapted to vibrate, or otherwise designed to ease tissue penetration.

In a preferred embodiment the cutter 140 has integrated cutter threads 160 (shown in FIG. 3) that mate with the housing thread 194 on the tissue capture housing 192 shown in FIG. 4. FIG. 5 shows how the outer cutter shaft 130 is assembled over the outside of the inner cutter shaft 190 and the threads 160 inside the cutter fit with the threads 194 on the outside of the tissue capture housing. In some embodiments the outer cutter shaft 130 does not rotate. In some embodiments the outer cutter shaft 130 does not advance toward the tissue during cutting, but instead the tissue is brought toward the cutter 140.

Figure 18:
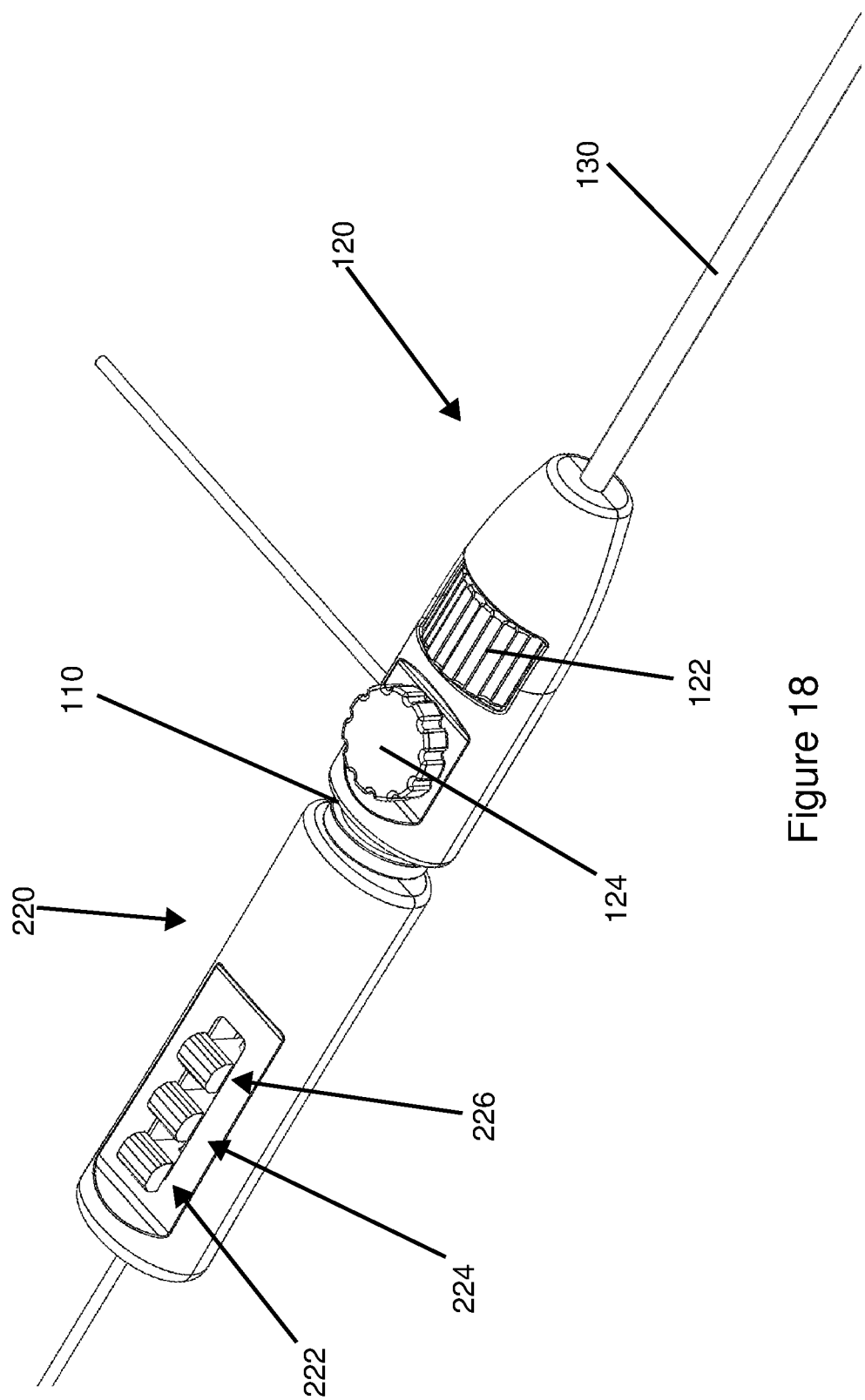
FIG. 18 is a partial perspective view of a handle for a septostomy system.

The inner cutter shaft 190 shown in FIG. 5 is preferably a torque shaft capable of providing torque and column stiffness to drive the blade forward as an outer shaft, e.g., the outer cutter shaft 130 rotates over the outside of it. In one embodiment, the inner cutter shaft 190 also provides one or more means for bending or steering the distal end of the device assembly 10 or the cutter assembly 100. In an alternative embodiment the outer cutter shaft 130 or another shaft provides a steering means. The inner cutter shaft is comprised of a thin walled highly torqueable catheter shaft 190, it may have a pull wire for distal tip steering (not shown), and a tissue capture housing 192. The steering may be done by multiple internal or external means, but may be accomplished with a single plane pull wire (not shown) meant to deflect the distal tip of the assembly 40 to 90 degrees such that it aligns somewhat perpendicular with the fossa. The pull wire may be attached distally to a metal ring assembly or the tissue capture housing 192, or similar. The location of the attachment will determine where the catheter bends at, and thus how long of a straight region is located just proximal of the cutter 140. In place of, or in addition to, the pull wire one or more catheters may have one or more preformed bends. Typically, the steering means will be in a catheter portion that does not rotate. Thus, if the steering means is located in the outer catheter shaft 130, the inner cutter shaft 190 or another element will provide rotation to drive the cutter 140 forward. If the steering means is located in the inner cutter shaft 190, the outer catheter shaft 130 will rotate. Multiple means may be provided for either steering or orientation of the septostomy system 10. A slight shaft prebend may help facilitate quicker alignment as well. Steering may be accomplished robotically, magnetically, or by other means known in the art. The proximal end of the tissue capture housing 192 is affixed to the distal end of the inner cutter shaft 190, through welding it to the shaft's braiding, reflowing, or a similar attachment method. In a preferred embodiment, the tissue capture housing 192 is made of a thin walled stainless steel hypo tube about 1-2 cm in length with a rounded distal edge 196, or another suitable metal or material adapted to allow components and tissue to move smoothly over its rounded distal edge 196. The distal end of the tissue capture housing 192 typically terminates near the cutting edge 150 of cutter 140. In a preferred embodiment the rounded distal edge 196 terminates nominally positioned slightly (0.1 mm-1 mm) distal to the nominal pre-cutting position of the distal end of the cutter blade. This position has two advantages, first it protects tissue from the blade during the system's 10 advancement, and second, it allows tissue to be pulled into the housing 192 prior to cutting. The latter is done to create a shunt larger than the diameter of the blade. The tissue capture housing 192 may or may not have blade advancement and control threads 194 on the outside. As seen in FIGS. 1 and 18 the cutter shaft assembly handle 120 is preferably affixed to the proximal ends of both the outer cutter shaft 130 and the inner cutter shaft 190. The handle 120 contains a tip deflection actuator 124 for controlling the orientation of the distal tip of the septostomy system. In one embodiment, the tip deflection actuator 124 controls a pull wire in the inner cutter shaft 190 to deflect the distal tip of the assembly. The cutter shaft handle 120 also contains a cutter knob 122 meant to rotate the cutter blade 140, e.g., though rotating one of the catheter shafts such as shaft 130. 190, 210, 260, etc.

The cutter shaft assembly handle 120 may also contain threaded components (complimentary to or in place of the threaded components 160, 194 in the distal end) to advance the blade into the tissue at a specific slicing angle when the knob 122 and blade are rotated. Markers (not shown) on the handle may show blade advancement in millimeters or similar dimensions so that the operator knows the distance the blade has advanced. A blade stop may be incorporated into the cutter shaft handle 120 so the blade edge does not advance to a position where it can create unwanted damage. For example, in a typical procedure the blade stop prevents the blade from advancing more than 6 mm beyond tissue capture point. Alternatively, a stop may be incorporated in the distal end of the assembly. The cutter shaft handle 120 has a blade lock that locks the blade 150 in position once it is advanced so the tissue is tightly controlled during extraction.

Figure 6:
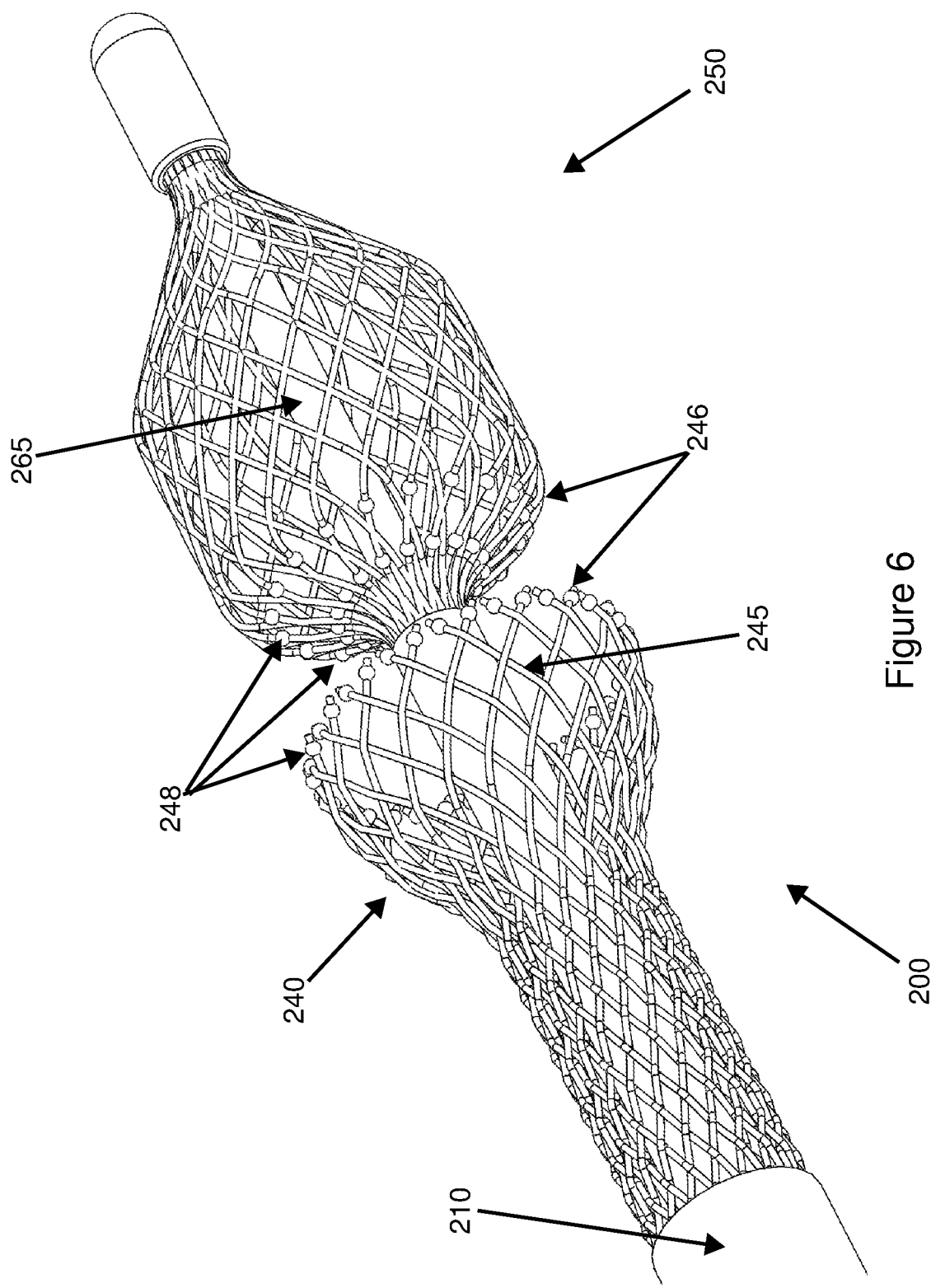
FIG. 6 is a partial perspective view of a capture mechanism constructed according to the present disclosure.
Figure 6A:
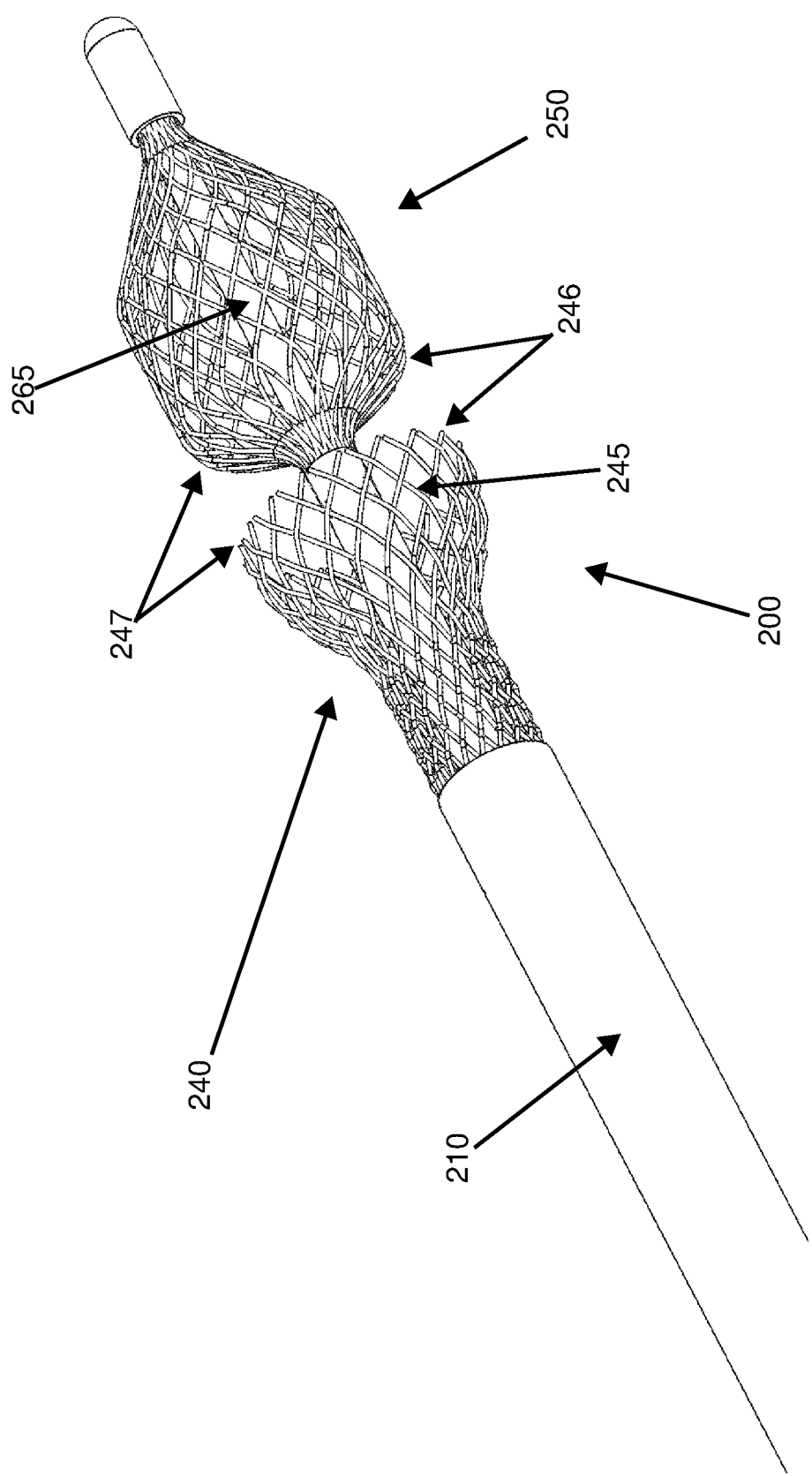
FIG. 6a is a partial perspective view of a capture mechanism constructed according to the present disclosure.

The cutter shaft handle 120 has a hemostasis valve 110 at its proximal end. This hemostasis valve 110 can serve multiple purposes. For example, it can serve as an entry point for dilator 50 for advancing the septostomy system 100 to the RA. After RA delivery the dilator can be withdrawn and the capture mechanism shaft assembly 200 can be introduced into the hemostasis valve 110 and into the RA. The capture shaft assembly 200 in FIGS. 6 and 6a is designed to be assembled together with the cutter shaft assembly 100. To fit them together during the procedure the distal end of the capture shaft assembly 200 is aligned to the hemostasis valve 110 on the proximal end of the cutter assembly handle 120. The capture shaft(s) are advanced through the hemostasis valve 110 until the two handle mechanisms 120, 220 can fit together. In a preferred embodiment the two handle mechanisms 120, 220 are locked together such that capture mechanisms are aligned with the tissue capture housing 192. For example, in one embodiment the initial location of the distal end of the proximal capture mechanism 240 is in alignment with the distal end of the tissue capture housing 192 on the distal end of the inner cutter shaft 190. In operation, the septostomy system 10 is brought close the RA side of the septum while so aligned. The system 10 is aligned laterally with the septum, and then the proximal capture mechanism 240 is deployed, either proximally of the septum or against it. At this point the distal capture mechanism is advanced across the septum and deployed or expanded. If not already in contact, the catheter is advanced forward longitudinally until the proximal capture mechanism touches the septum, then the distal capture is pulled back to capture the tissue. Though a preferred methodology is disclosed, there are several variants to the procedure, including contacting the septum with the distal capture mechanism first, etc.

The shafts, e.g., 130, 190, 210, etc. may include irrigation ports, vacuum ports, and the like, radiopaque markers, including in a designed pattern that allows the physician to determine the location and orientation of the system in the patient and the location and orientation of the different components of the device relatively to each other. The system 10 may further include ultrasound markers again in a designed pattern such that the physician may locate the system 10 or its components in the patient on ultrasound imaging. Of course any catheter or system portion described herein may use any one or combination of markers, such as radiopaque, ultrasound, electrodes, magnetic sensors, or visualization systems to determine the location of the catheter or system portion in the body or with respect to another portion of the system. Other location systems are possible, including MRI, electroanatomical navigation systems such as EnSite®, Carto®, or MediGuide® systems, along with the corresponding sensors. Likewise, electrodes, pressure sensors, fiber optics, a camera, or the like may sense the tissue contact or proximity, and may thus identify when the system 10 is in contact with the tissue, and also when it is orthogonal to the tissue.

With reference to FIG. 5, the capture shaft assembly 200 can be comprised of a proximal capture shaft 210 and distal capture shaft or sheath 260, both operationally attached to one or more capture shaft handle(s) 220 (FIG. 1).

The proximal capture shaft 210 is preferably a high column force catheter shaft with an expandable proximal capture mechanism 240 near its distal end, and attached to a capture shaft handle 220 at its proximal end. The proximal capture mechanism 240 depicted in FIGS. 5-6a is preferably made of a braided nitinol wire 245 construction, though other materials are contemplated, such as stainless steel, polymeric materials, wire filars, and the like. The nitinol wire braid 245 may be in tubular form and attached to the distal end of the proximal capture shaft by welding, braising, gluing, soldering, reflowing or similar. Its most distal outer diameter may be heat set to a nominally open diameter which is larger than the inside diameter of the distal end of the tissue capture housing 192 that contains it, as seen in FIGS. 5-6a, such that when the distal end of the proximal capture mechanism 240, is pushed distal relative to the distal end of the tissue capture housing 192 and the cutter 140, it expands to a preset expanded diameter. It may also be expanded by use of an actuator, for example an actuator that shortens the linear length of the proximal capture mechanism 240, causing its diameter to increase, expanded by use of a release mechanism, e.g., on the handle 220, or be expanded by the use of multiple catheter shafts to draw its ends closer together.

Figure 9:
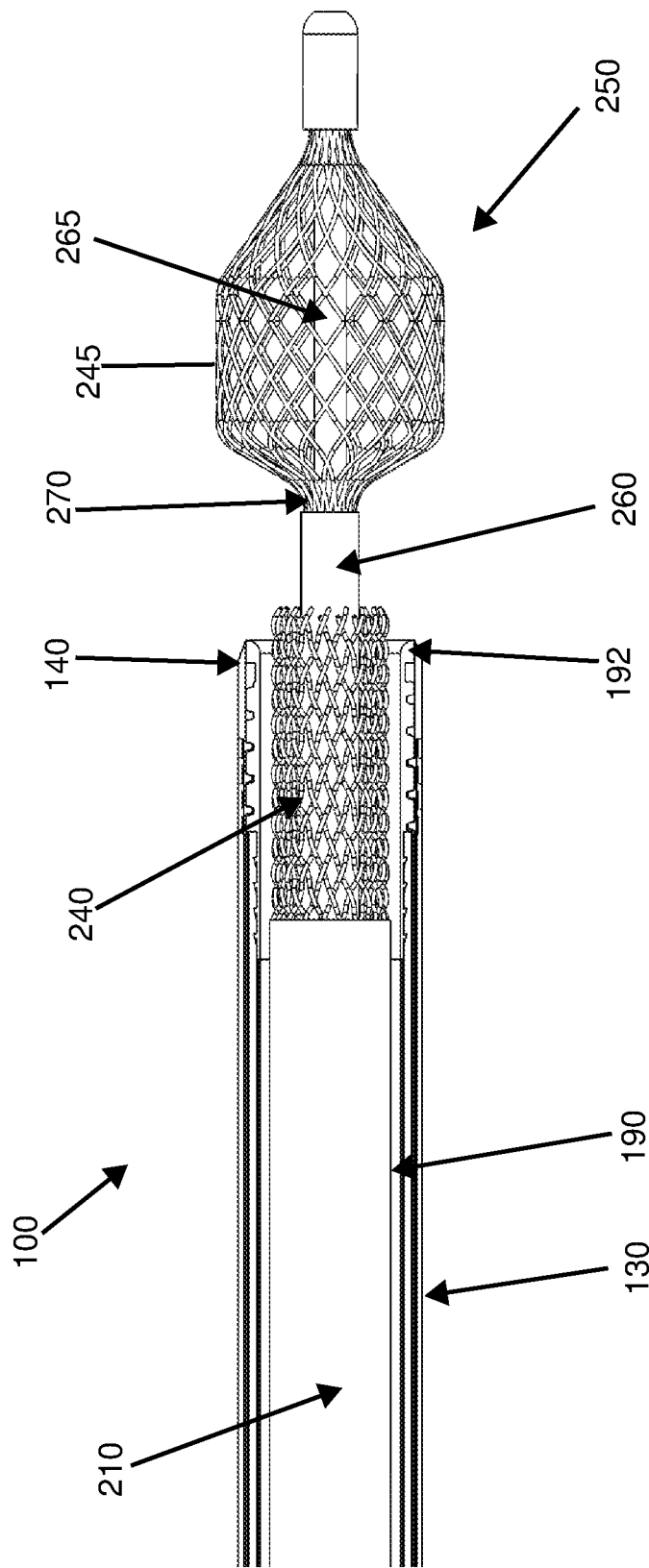
FIG. 9 is a partial perspective view of a septostomy system constructed according to the present disclosure.
Figure 10:
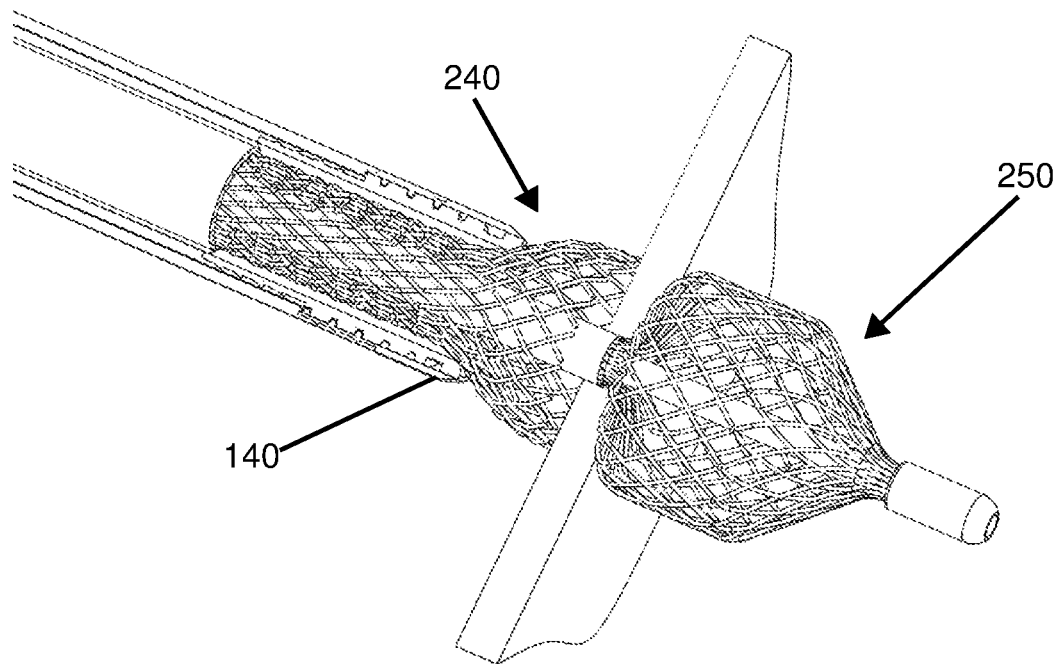
FIG. 10 is a partial perspective view of a septostomy system constructed according to the present disclosure in place on the septum.
Figure 11:
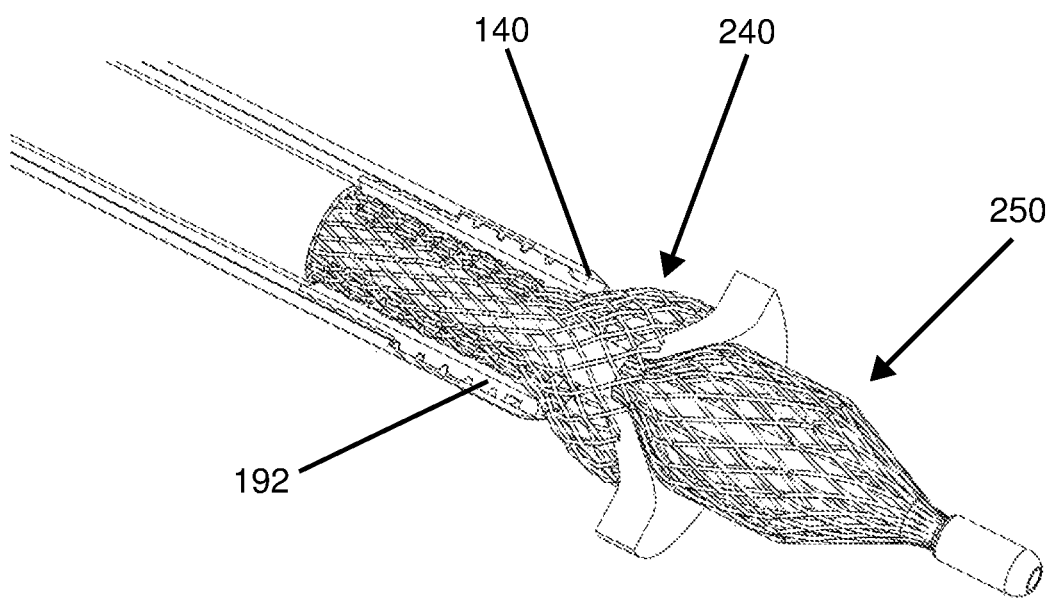
FIG. 11 is a partial perspective view of a septostomy system constructed according to the present disclosure capturing a portion of the septum.
Figure 12:
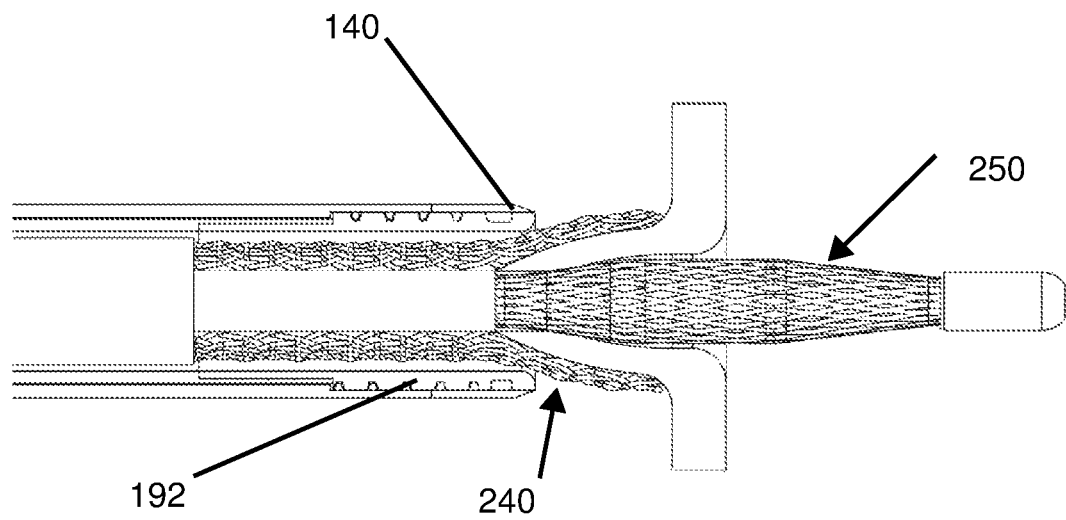
FIG. 12 is a partial perspective view of a septostomy system constructed according to the present disclosure drawing a portion of the septum into the device.
Figure 13:
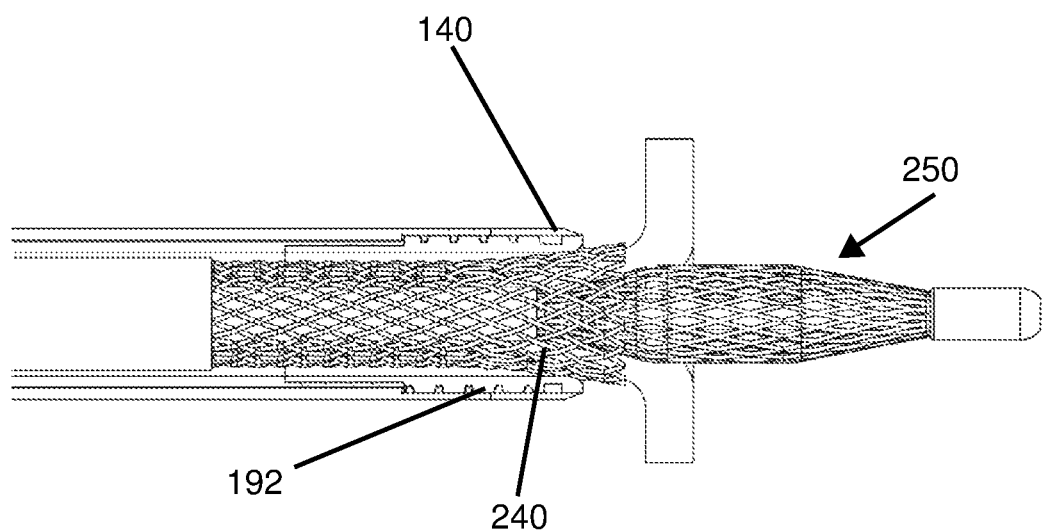
FIG. 13 is a partial perspective view of a septostomy system constructed according to the present disclosure drawing a portion of the septum into the device.

When the proximal capture mechanism expands the wire braid 245 orientation may be as shown in FIG. 6, or the braided wire 245 configuration may be more closely spaced (FIG. 7) or doubled (FIG. 9) such that when linear and axial capture force or side loading is applied the capture mechanism holds its preferred shape more robustly. In this configuration the nitinol wire braid 245 at the distal end of the proximal capture mechanism 240 may preferably be closer to parallel to the axial orientation of the capture shaft 210. Nitinol wire braid 245 may also preferably be perpendicular to the axial orientation of the capture shaft 210, and thus more effectively apply linear force to any tissue. While FIG. 7 shows the filars 245 at a diagonal orientation, the filars 245 may also be perpendicular to the axial orientation of the capture shaft 210, or be parallel to it. A similar effect may be accomplished by adding more filars 245 as seen in FIG. 7 or FIG. 9. This perpendicular orientation can create a stacking of wires allowing the braided tube 210 of the proximal capture mechanism 240 to hold significant tissue capture force aligned with the axial orientation of the catheter shaft 210. Likewise bands 244 may be placed around portions of the proximal capture mechanism 240 to provide additional support, interstices may be reinforced, e.g., by glue or welding, and other means may be used to allow additional capture force to be applied.

Radial orientation of the proximal capture mechanism 240 is controlled by either the fit with the inside of the tissue capture housing 192 or the fit with the distal capture shafts. The preset expanded diameter maybe set via heat treatment, cold forming or similar method. The preset nominal expanded outside diameter of the proximal capture mechanism may be 3 mm to 11 mm, or slightly larger than to slightly smaller than the diameter of the tissue to be cut. The distal end of the collapsed or compressed proximal capture mechanism 240 has an outside diameter just smaller than the inside diameter of the tissue capture housing 192, and an expanded outside diameter similar to the outside diameter of the distal capture mechanism 250, such that most of its contact force with the tissue is at its outer perimeter 246, as seen FIGS. 6 and 6a. By way of example, in a septostomy system 10 having a 7 mm OD outer catheter shaft 130 with a 6 mm cutter 140, the proximal capture mechanism 240 may have a compressed OD of 5.5 mm or less, but expands to an 8 mm capture mechanism capable of grasping an 8 mm section of the fossa ovalis, typically in conjunction with the distal capture mechanism 250. Preferably the proximal capture mechanism of the 7 mm OD catheter can expand at least 25% more than the OD of the outer catheter, and more preferably at least 50% more.

In addition, while the fully expanded proximal capture mechanism may have a first fully extended diameter, the effective diameter of the proximal capture mechanism 240 may be reduced, for example via an actuator or by partially withdrawing the mechanism 240 into the tissue capture housing 192 before engaging the tissue. In such a case it is helpful to have a marker or graduated actuator so that the operator can readily determine, and select the size the proximal capture mechanism 240 is expanded to. In a preferred embodiment, the distal capture mechanism can also have its expanded size varied, e.g., by adjusting the distance between its proximal and distal ends with two shafts (see below).

The Proximal Capture Mechanism 240 in FIGS. 5 and 6 may have a variety of cross-sectional shapes like simple tubular structures, conical structures, funnel shapes, or irregular shapes. In its partially or fully open condition the proximal capture mechanism 240 can transmit up to 4 lbs of tissue capture force onto the outer capture perimeter 246 of the captured tissue without collapsing, while having some spring loading either in itself, in the shaft, or on its handle. The spring loading can serve multiple purposes, including maintaining a constant force regardless of variable tissue thickness, and allowing for high perimeter capture force while the proximal capture mechanism is withdrawn into the tissue capture housing 192, as seen in FIGS. 8c, 10-13. The tissue capture housing 192 has a rounded or radiused distal end 196 such that the tissue and the capture mechanisms 240, 250 can be pulled across it with minimal friction. The proximal capture mechanism 240 is designed to at least initially place substantially all (90%) or most (60%) of the capture force at the perimeter of the captured area, such that after capture the tissue does not slip from the capture mechanisms. Thus, a prescribed tissue area is maintained prior to, during, and after cutting and removal.

To facilitate minimal slipping of the captured tissue at lower capture forces the proximal capture mechanism 240 may contain small capture points 247 or barbs to keep tissue from slipping. The capture points 247 are ideally at or close to the perimeter of the captured tissue, as seen in FIG. 6a. The barbs could be sharpened braid wire ends. Likewise, hooks, suction, heat or cooling, magnetism, or other means can be utilized to hold the tissue. The capture points may be distributed around the perimeter as depicted in FIG. 6a. There may also be interior capture points that work with the perimeter capture points, or work separately to assist in the compression, cutting, or the like of the tissue. For example, a first set of barbs could secure the tissue perimeter, while a second set of hooks or barbs pulls a portion of the tissue proximally, and a third set of capture points pulls another portion of the tissue distally.

To better hold the most distal end of the nitinol wire braid ends connected into the preferred tubular shape a thin layer of elastic polymer (not shown), such as polyurethane, may be placed in a circumferential fashion about the most distal end of the proximal capture mechanism 240.

Alternatively, the proximal capture mechanism 240 may be made of a nitinol cut tube (as with the distal capture mechanism 250 depicted in FIG. 8c) or similar material, formed and heat set in such a configuration that it expands from a relatively small diameter of 2-6 mm to nominally open in a tissue capture configuration 50% larger than its initial size, e.g., between 3-11 mm at the capture perimeter when advanced fully or partially out of the tissue capture housing 192. With reference to FIG. 5, the capture shaft assembly 200 can also be comprised of a distal capture shaft or sheath 260 operationally attached to a capture shaft handle 220 of FIG. 1.

There may be multiple distal capture shafts which control the shape and longitudinal positioning of the capture mechanisms 240, 250. For example, a first distal capture shaft 260 and a second distal capture shaft 265 may change a distance between the proximal and distal ends of the distal capture mechanism 250 relative to each other, or relative to the tissue, or relative to the rest of the septostomy system. While different orders and combinations of shafts are contemplated, one preferred embodiment will be described. In this embodiment a first capture shaft 265 may or may not have an inner lumen for a guidewire or other device. In one embodiment the first capture shaft 265 is the innermost of multiple coaxial capture shafts, and may be called an inner capture shaft. In another embodiment, the first capture shaft may lie next to another capture shaft, both shafts located inside the lumen of a larger shaft.

This first capture shaft 265 may be made of, for example, nitinol, polymer, stainless steel, or a combination of, such that it has a thin wall but still high column and pull strength, to open and close the distal capture mechanism 250, and to hold it tight against the tissue during tissue capture. The distal end of the first capture shaft 265 is operatively connected to any portion of the distal capture mechanism 250, but is preferably attached to the distal end of the distal capture mechanism by a weld, an adhesive joint, or similar mechanism.

In addition, the septostomy system 10 may include a second capture shaft 270. This shaft may lie alongside the first capture shaft 265, or coaxially with shaft 265, e.g., outside of it. In a preferred embodiment the second capture shaft 270 is attached to the proximal end of the distal capture mechanism 250, while the first capture shaft is attached to the distal end of the distal capture mechanism 250. This second capture shaft 270 may also be made of nitinol, polymer, stainless steel or combined construction such that it has a thin wall but still high column and pull strength, to open and close the distal capture mechanism 250, and to hold the distal capture mechanism 250 tight against the tissue during tissue capture. In operation, the first and second capture shafts 265 270 operate to open and close the a capture mechanism by changing the distance between the proximal end and distal end of the capture mechanism. As the two ends are drawn together, the capture mechanism is pushed into an open position (though in an embodiment, the capture mechanism is also nominally open, and thus will pop open on its own as well). By locking the two shafts into position with the distal and proximal ends of the capture mechanism in a closer position, the two shafts supply rigidity and better capture force for the capture mechanism.

While in some embodiments the distal capture mechanism is held in a constrained posture during the crossing of the fossa ovalis or the atrial septum by cutter assembly 100, tissue capture housing 192, or another component, the device may advantageously comprise a distal capture sheath 260 as well. If utilized, the distal capture sheath 260 is a thin walled polymer containment device or tube used to hold the distal capture mechanism 250 at a minimal diameter during the crossing of the fossa ovalis or atrial septum. The distal capture mechanism 250 is delivered across the fossa ovalis by retaining it with a distal capture sheath 260 which advances with the collapsed distal capture mechanism into the LA, then stops (e.g., through a stop in handle) 1 cm into the LA to deploy the distal capture mechanism 250.

Figure 8B:
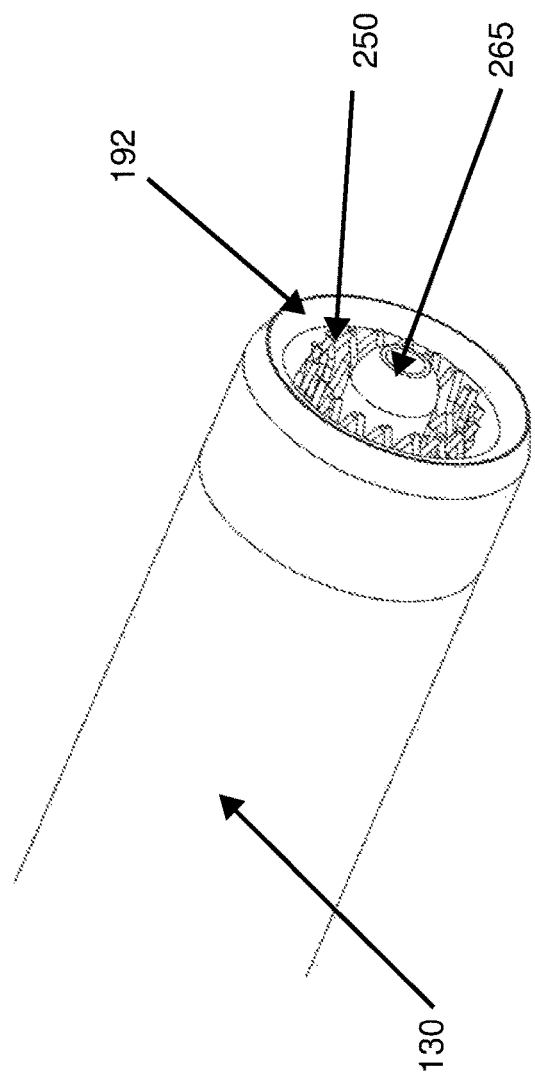
FIG. 8b is a partial perspective view of a collapsed proximal capture mechanism inside a tissue capture housing.
Figure 8C:
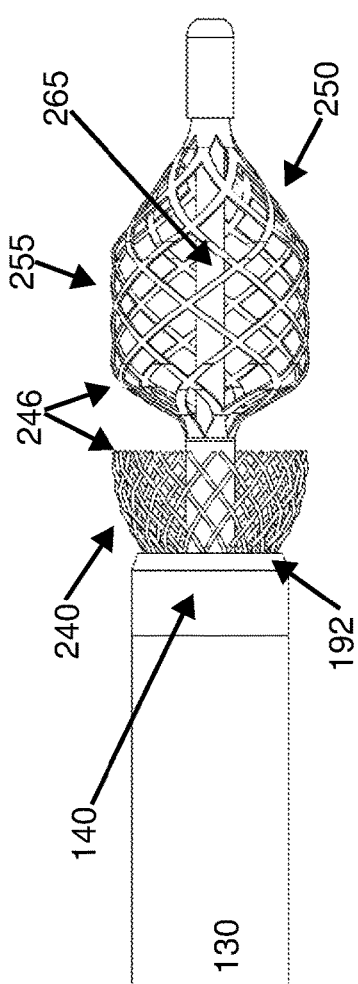
FIG. 8c is a partial perspective view of a proximal capture mechanism and a distal capture mechanism partially exiting a tissue capture housing.

FIGS. 8a and 8b show the distal capture mechanism and the proximal capture mechanisms in the pre-deployment configurations, as they would be within the tissue capture housing 192, as seen in FIG. 8b. FIGS. 8c and 9 show the capture mechanisms, as they would be configured if the proximal capture mechanism was not yet deployed (9) or was partially deployed (8c), but the distal capture mechanism was partly or fully deployed.

The distal capture mechanism 250 may be made of a nitinol wire braided structure so that it can cross the fossa at a low profile, be easily visible on fluoro or echo, so that it can be advanced until it is contacting the fossa is in its natural plane, be easily expandable to a nominally open shape formed to capture tissue with a high capture force at the outer perimeter 246 of the captured tissue area. The distal tip of the distal capture mechanism 250 may have a tapered crossing tip w/hydro coating to minimize stretching and tearing of the fossa ovalis tissue when it is pushed across. When the tissue contacts the cutter edge 150 it is preferred that the shape of the distal capture mechanism 250 may have an outer diameter slightly smaller than the inner diameter of the cutter and extend distally such that the two remain in close proximity over the full travel of the cutter, such that no tissue is inadvertently cut. This can be when the distal capture mechanism 250 is fully expanded, or when it is partially expanded as its withdrawn into capture housing 192. Preferably the distal capture mechanism 250 includes a large middle section 255 that has a consistent diameter as its withdrawn into the cutter or the cutter rides over it.

Distal to this large diameter middle section, the distal capture mechanism may taper to the distal capture shaft in a fashion which holds higher capture force. To hold a high capture force the distal tapered and middle braided sections of the open distal capture mechanism are constructed with a tight braid pattern when nominally open, such that linear compression under loading is minimal. There may be other means to give this distal capture mechanism radial and linear rigidity for a high strength capture. For instance the inner and or outer surfaces of the braid or other distal capture mechanism structure may be integrated with an elastomeric coating (not shown), such as polyurethane, forming an integrated balloon which can be attached to an inflation shaft and inflated by the clinician. This same elastomeric coating gives the device additional embolic protection capabilities. In this open configuration not only is the braid filar arrangement tight but also the wire is largely perpendicular to the axial orientation of the catheter shafts. This tight braid pattern also acts as an embolic protection device. Other embolic protection methods may also be employed, like a thin layer of polyurethane or silicone over part or all of the distal capture mechanism. This may not be necessary of the distal capture mechanism is a solid material or with gaps between material segments less than 0.1 mm.

The capture force loading is carried from the tissue onto the stacked filar assembly to the distal tip of the distal capture mechanism and onto one or more distal capture shafts 260, 265, 270. Distal capture mechanism 250 will ideally have high radial stability before and after capture such that it holds capture perimeter alignment with the proximal capture mechanism 240 on the opposite side of the atrial septum, such that the outer perimeter capture forces are close to opposing. This radial stability may be accomplished by connecting the capture perimeter 246 at the proximal end of distal capture mechanism to one of the distal capture shafts.

Alignment of the two capture mechanisms can also or alternatively be accomplished by having one of the capture mechanisms slightly smaller than the other, fitting into one another, or by having a tapering component to guide one of the capture mechanisms into the other such as the proximal end of distal capture mechanism 250 in FIG. 6. This is not trivial as fossa ovalis tissue thickness and general morphology can vary significantly, potentially causing capture misalignment, and for safety reasons it is important to apply high and controlled capture force to the tissue prior to cutting. For this reason the structure of the proximal end of the distal capture mechanism may be of a conical shape, made of a nitinol braid such that it is nominally open, with wire filars stacked tight so that it holds a high column loading strength. The maximum diameter of the distal capture mechanism 250 structure is to match or be slightly smaller or slightly larger than the diameter of tissue meant to be cut.

The proximal end of the distal capture mechanism 250 may be approximately 45 degrees pointed proximally, such that it holds radial stability of the capture perimeter 246 and also starts to tent tissue into the proximal capture mechanism and housing. The proximal end of the distal capture mechanism 250 may at capture also be sloped distally at some angle to give room for tissue, allow for a higher capture perimeter 246 force, and to allow for the device to collapse further distally. The proximal end of the distal capture mechanism may also be at a different angle, including zero, and pointed in another direction, as long as it is able to hold a high capture force at its perimeter.

The distal capture mechanism is designed to at least initially place all or most of the capture force at the perimeter of the captured tissue area, such that after capture the tissue does not slip from the capture mechanisms, such that a prescribed tissue area is maintained prior to, during, and after cutting and removal. To facilitate minimal slipping of the captured tissue at lower capture forces the distal capture mechanism may contain small capture points or barbs 247 to keep tissue from slipping. The points 247 are ideally at or close to the perimeter of the captured tissue, as seen in FIG. 6a. The barbs 247 could be sharpened braid wire ends.

After tissue capture, both the distal capture mechanism 250 and the proximal capture mechanism 240 are pulled into the tissue capture housing. See FIGS. 10-13. This withdrawal elongates the nitinol wire braiding on both capture mechanisms, e.g. at the proximal ends. This pulls tissue into the tissue capture housing 192, and it shrinks the diameter of the captured tissue perimeter, such that the tissue within what was for instance an 8 mm captured tissue perimeter is forced into a 6 mm diameter space, elongating it within the capture mechanisms, and preparing it to be cut with a 6 mm cutter. The capture mechanisms are designed in such a way that as the capture mechanisms are being pulled into the tissue capture housing with the captured tissue the capture force at the captured tissue perimeter is maintained above a set minimal level. This is accomplished by having one or more of a high capture force, a perimeter capture force, capture points, and spring elements in the handle or in the capture mechanisms themselves which maintain the capture force during tissue retraction.

Figure 14:
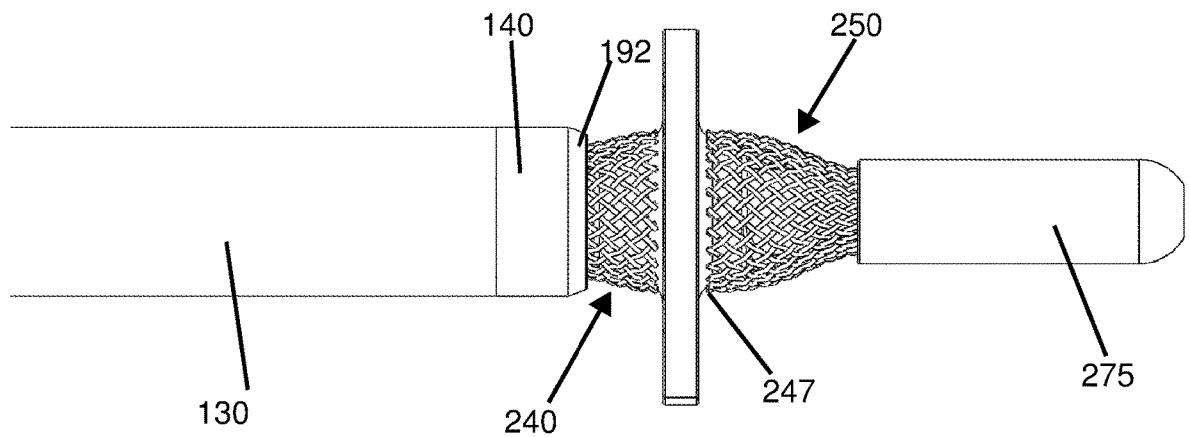
FIG. 14 is a partial perspective view of a septostomy system constructed according to the present disclosure capturing a portion of the septum.
Figure 15:
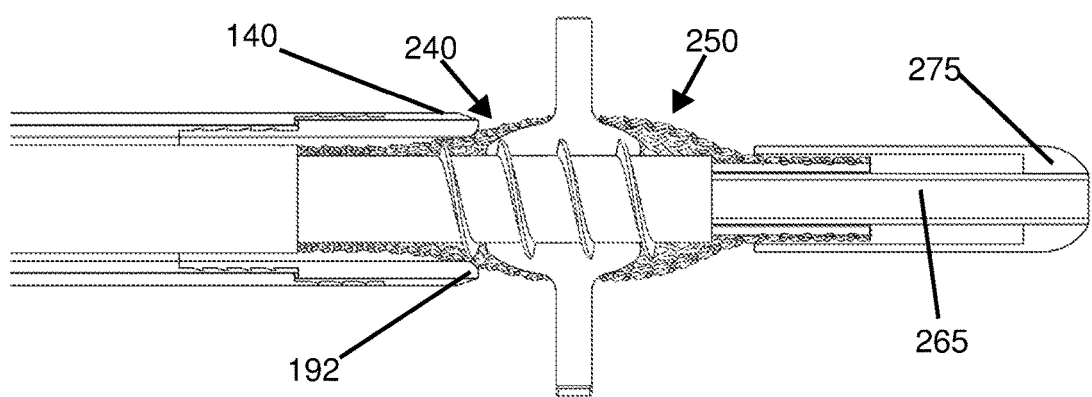
FIG. 15 is a partial perspective view of a septostomy system constructed according to the present disclosure drawing a portion of the septum into the device.

In FIGS. 10-13 the distal capture mechanism 250 may be designed in such a way that it deflects the captured tissue proximally during diameter reduction or withdrawal. In FIGS. 14-15*a* the distal capture mechanism 250 is designed in such a way which forces or allows the captured tissue volume to extend both distally and proximally as it is compressed through diameter reduction. This distal capture mechanism design is similar to the preferred proximal capture mechanism design. This alternative design for the distal capture mechanism 250 may be constructed as discussed herein with respect to the proximal capture mechanism 240, or as a nitinol cut tube as in FIG. 8*c*, or a nitinol rolled tube construction in which the distal capture mechanism expansion occurs as it exits a catheter shaft 265, distal capture tube 275, or a distal sheath or tube in the left atrium of the heart. After the tissue is captured the distal capture mechanism can be pulled or pushed back into the tube 275 to reduce the tissue in diameter so that the tissue can be cut. The length of tube 275 in the left atrium that it needs to be pulled into may be relatively short.

As shown in FIG. 18 the capture assembly 200 may further include a small auger 290 or similar cutting mechanism. The cutting mechanism 290 may rotate over a capture shaft, or be actuatable to move over a shaft. In use, the auger or cutting mechanism 290 works to cut tissue and move it into the tissue capture housing, a shaft, or another cavity. In particular, the auger may work with the proximal and distal capture mechanisms so that the tissue is broken up to allow the tissue to be more readily deflected in both the proximal and distal directions, or so that it may more readily be deflected proximally, or deflected distally. The auger or the cutter may move, or the tissue may be drawn over one or more stationary blades/augers by the capture mechanisms.

The auger could have a sharp metal blade, and be accompanied by a saline irrigant and/or suction to help move cut tissue proximally into, through, or out of the capture zone. Such a design can cut the captured tissue and move it proximally into the shaft as the capture mechanisms reduce the tissue diameter and force the tissue onto the blade for cutting. With such a design the distal and proximal capture mechanisms only needs to capture the tissue at the outer capture perimeter and forcibly reduces the perimeter diameter, forcing tissue onto the auger debulking mechanism, which cuts and removes the tissue from the inside diameter. The auger cutter can use a sharp edged blade, an RF blade, a laser cutter to separate tissue, or a combination. Instead of an auger to move tissue proximally the separated tissue can be moved proximally into the shaft of the catheter with a linear cutting device, or a suction type device. A linear cutting device may simply be a cut metal tube distal capture mechanism which has sharpened inner edges which are able to cut and separate tissue as it is pulled into the end of the catheter shaft or tissue capture housing. Ideally when the debulking is being performed with or without a mechanical means of moving tissue proximally a suction may be applied to a shaft thru a valve on the proximal end of the system. This suction helps move tissue proximally into the shaft making room for more tissue, as well as helps prevent vapor from desiccation or vaporization from entering the blood stream. Likewise, an irrigation/vacuum loop can be employed with a debulking mechanism to wash loose tissue toward the proximal end of the system.

Alternatively both distal and proximal capture mechanisms may be designed similar to the distal capture mechanism structure in FIG. 8*c*, a slotted or rolled tube. In this design both LA and RA tissue surface areas captured within and between the two capture mechanisms have much of their surface area contacted by the capture mechanism. The tube is slotted on its proximal face such that when it is opened to capture tissue the slots become diamond shaped. The inside edges of the diamond shape can be sharpened to cut tissue. If the tissue diameter needs to be decreased, both distal and proximal capture mechanism surfaces may deflect, like the proximal side of the distal capture mechanism in FIG. 11, or form a conical shape in the same direction. They may alternatively form conical shapes in opposite directions to provide volume for the retracted tissue as in FIG. 14. In the latter case the proximal end of the distal capture mechanism would have its most center capture surface deflect distally and the most center capture surface of the distal end of the proximal capture mechanism would deflect proximally such that both devices provide a continuous capture force at the outer diameter perimeter of the captured tissue, while providing room for the tissue to be retracted in diameter. In this embodiment there would be room for the tissue to deflect, stretch, or be compacted in both the proximal and distal directions, as shown in FIG. 15.

Alternatively both or either of the proximal and distal capture mechanisms may be made of a nitinol cut tube formed like the distal capture mechanism in FIG. 8*c*, and heat set in such a configuration that it expands nominally open to between 3 mm to 11 mm when advanced fully or partially out of the tissue capture housing 192. The capture mechanisms may be made of both braided wire and cut tubes, configured into a variety of shapes, or a combination of a cut hypo tube and a balloon, or a combination of a balloon and the previous structures. The distal capture mechanism 250 may be made of, or coated with, a porous material such that no large emboli can pass. Alternatively there may not be any porosity.

Figure 16A:
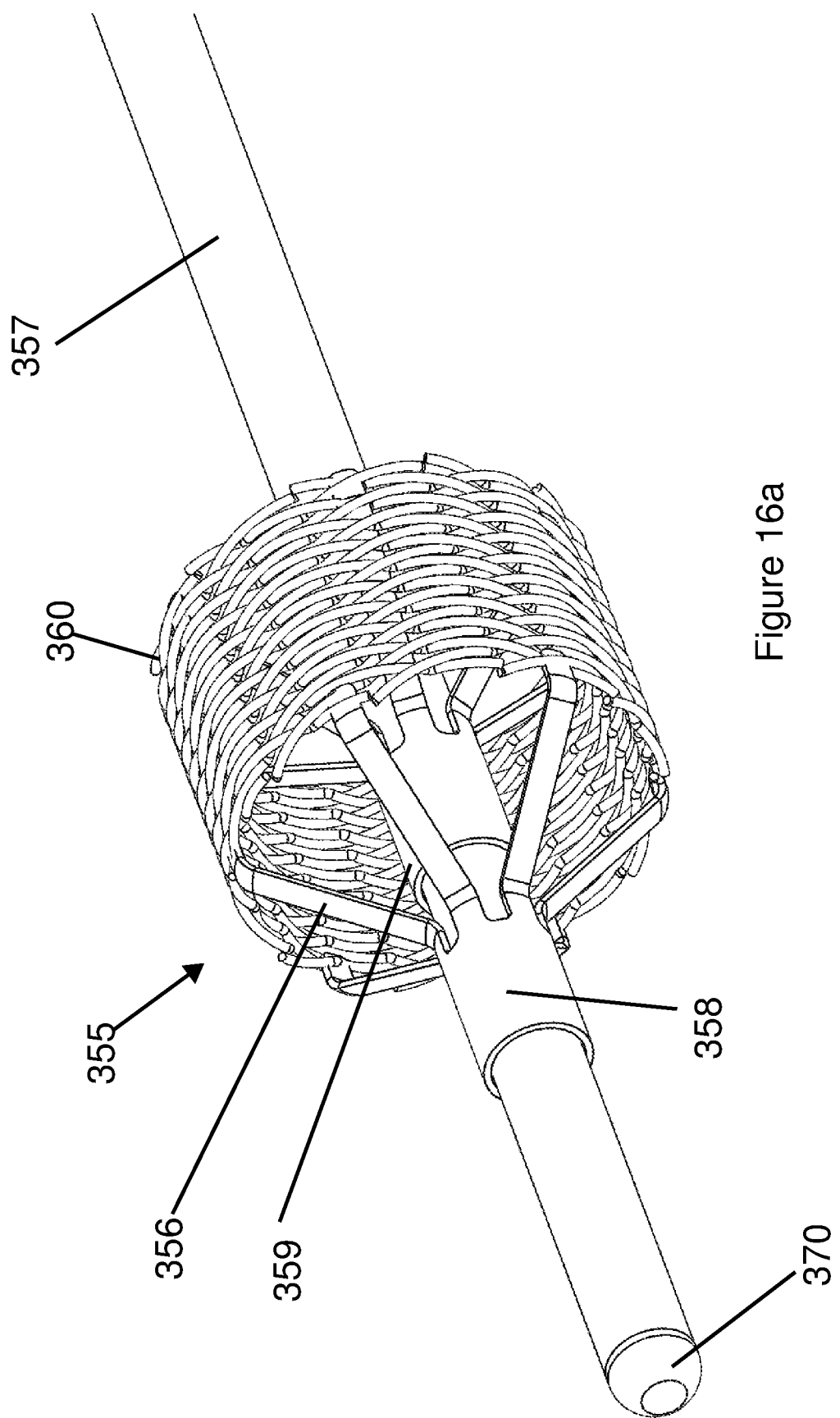
FIG. 16a is a partial perspective view of a septostomy system constructed according to the present disclosure.
Figure 16B:
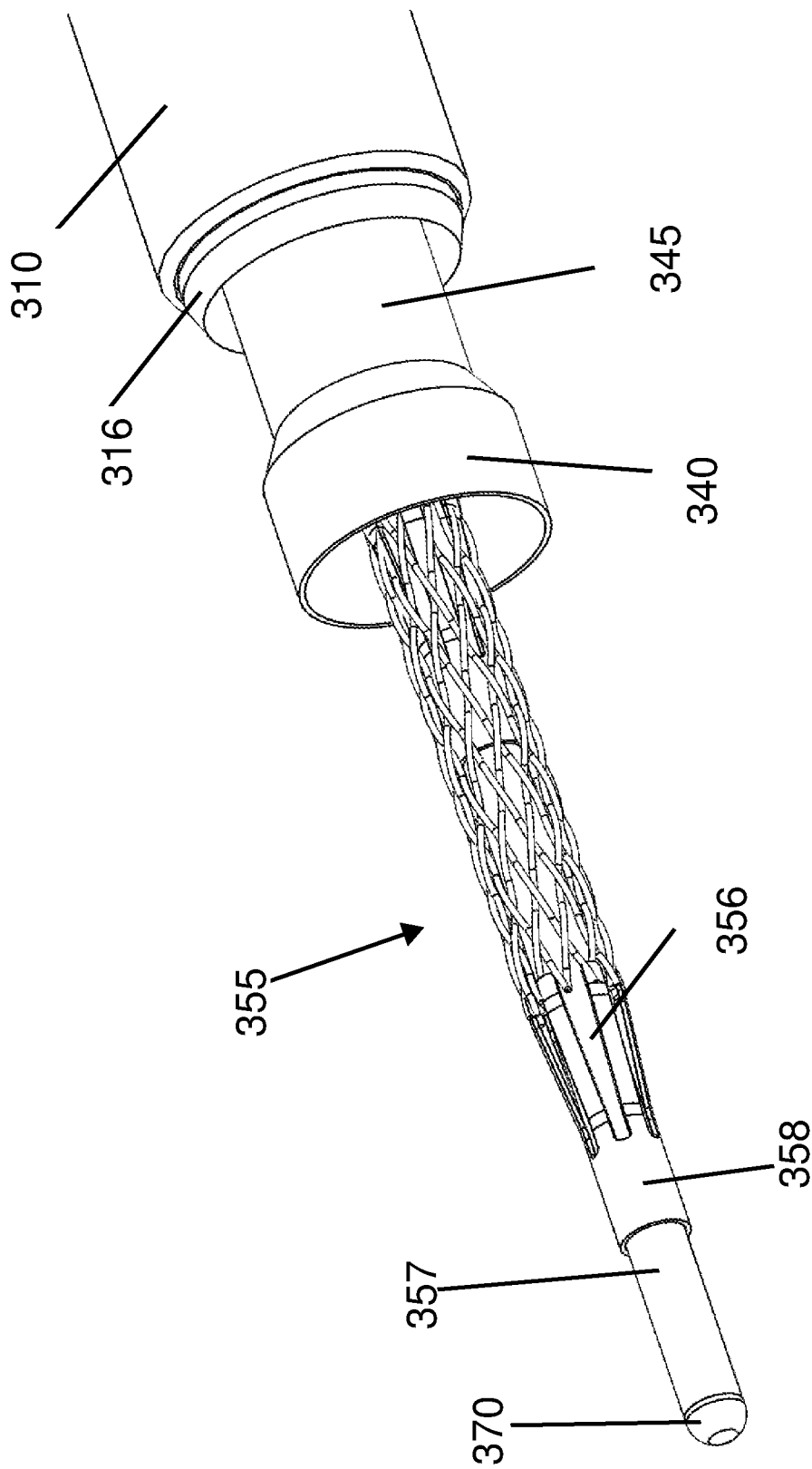
FIG. 16b is a partial perspective view of a septostomy system constructed according to the present disclosure.

As shown in FIGS. 16*a* and 16*b*, in one embodiment a capture mechanism (either proximal or distal) 355 consists of a shaft 357 with a distal tip 370. Distal tip 370 may be atraumatic, and may have a lumen exit for a guidewire. A nitinol structure, such as wire braided cylinder 355 or basket 355 may be connected to shaft 357 by struts 356. Some or all of struts 356 are connected to the shaft 357 by a laterally movable collar 358. While the capture mechanism is within the catheter 310 or sheath, or a retention sleeve (not pictured) in one embodiment the collar 358 is moved to its most distal location, pulling struts 356 down to lie closely on top of shaft 357, as shown in FIG. 16*b*. Doing so pulls weave 360 inward to likewise lie closely on top of struts 356, substantially reducing the diameter of the capture mechanism for delivery to the RA or the LA. In one embodiment, a sleeve (not shown) remains over the basket 355 to keep it in the withdrawn position, until the device crosses the septum to the LA, at which point the sleeve is withdrawn, or the shaft 357 and basket 355 are further advanced to exit the sleeve. When collar 358 is moved to its proximal position, e.g., via actuation or via biasing, the struts push away from the shaft 357, and weave 360 expands, creating a large surface area. The capture mechanism may have one collar, or it may have proximal 359 and distal 358 collars, one of which or both being slidable with respect to the shaft 357, and each other. When the collars 358 and 359 are pushed apart (via actuation or biasing) the weave is contracted. When they are pulled together, the weave is expanded.

The expandable distal devices disclosed herein may rely on a button or certain mechanism to force them open (nominally closed), or rely on some type of containment tube/system, that when released, they open by themselves (nominally open). The latter is preferred though, so it fails open and does not lose tissue.

The capture mechanism may be set to be nominally open, that is, when it is not constrained it returns to or stays in an open state. This can be a preferred fail safe, as once the aperture is cut the device can still be pulled through the fossa ovalis in its open state, but will retain any tissue. For example, the struts 356 and basket 355 may be formed of nitinol in its open state. In this embodiment, the device may be stored in an open state, and an early step in the procedure is to contract the basket 355 and place it inside a sleeve, tube, or catheter (not pictured) that will hold it in its contracted position.

In another embodiment the basket 355 is formed of a readily deformable material, such as stainless steel. In this embodiment it is delivered in its constricted or reduced form, as shown in FIG. 16b, and is nominally closed. That is, it is biased to be closed, or reduced to a smaller diameter, during delivery, as shown in FIG. 16b. At the desired location (e.g., in the LA if a distal tissue capture mechanism, or in the RA if a proximal tissue capture mechanism), it is actuated and deformed to an open, or larger form as shown in FIG. 16a. Because the stainless can be deformed from one shape to another, once actuated the basket 355 is now nominally open. If any constraint is removed, it remains in the open position as a failsafe.

It is then positioned, as described above, on the distal side of the tissue. As shown in FIG. 16a, the capture mechanism 355 has several advantages. A reduced diameter while collapsed allows easy and safe transseptal crossings, with minimal tissue damage. The increased opened diameter allows a large tissue area to be captured. In addition, the design of the capture mechanism 355 allows all of the devices retention force to be placed along the outer edge of the tissue portion to be cut, providing a more certain retention of the tissue while avoiding sliding or movement of the tissue during or prior to cutting. The diameter of the distal tissue retention device 355 preferably matches or is complimentary of the diameter of the capture mechanism 340, on shaft 345. Because they are on separate shafts, the proximal and distal tissue retention devices may be advanced, withdrawn, or actuated independently of each other and the cutter 316 and the catheter 310.

As drawn for the sake of illustration, capture mechanism 355 appears open at its distal end. However, to ensure tissue retention, the device 355 may have a tissue trap or a sealing material, e.g., a fine mesh on the distal end to retain any tissue portions that come loose. The expanded size of the capture mechanism ideally matches any capture mechanism on the other side of the tissue, such that one either fits neatly inside the other to hold the tissue, or that their diameters match, and are just slightly smaller than that of the cutter 316.

As shown in FIGS. 16a and 16b, basket 355 may be conical in shape. It may also take on a tapered shape, e.g., a cone or elongated cone with a narrower distal portion. In such an embodiment it may serve as a dilator for navigation through the body. The weave may be tight enough that the tapered cone may serve as a tissue trap, or another material may serve as a tissue trap.

Figure 17A:
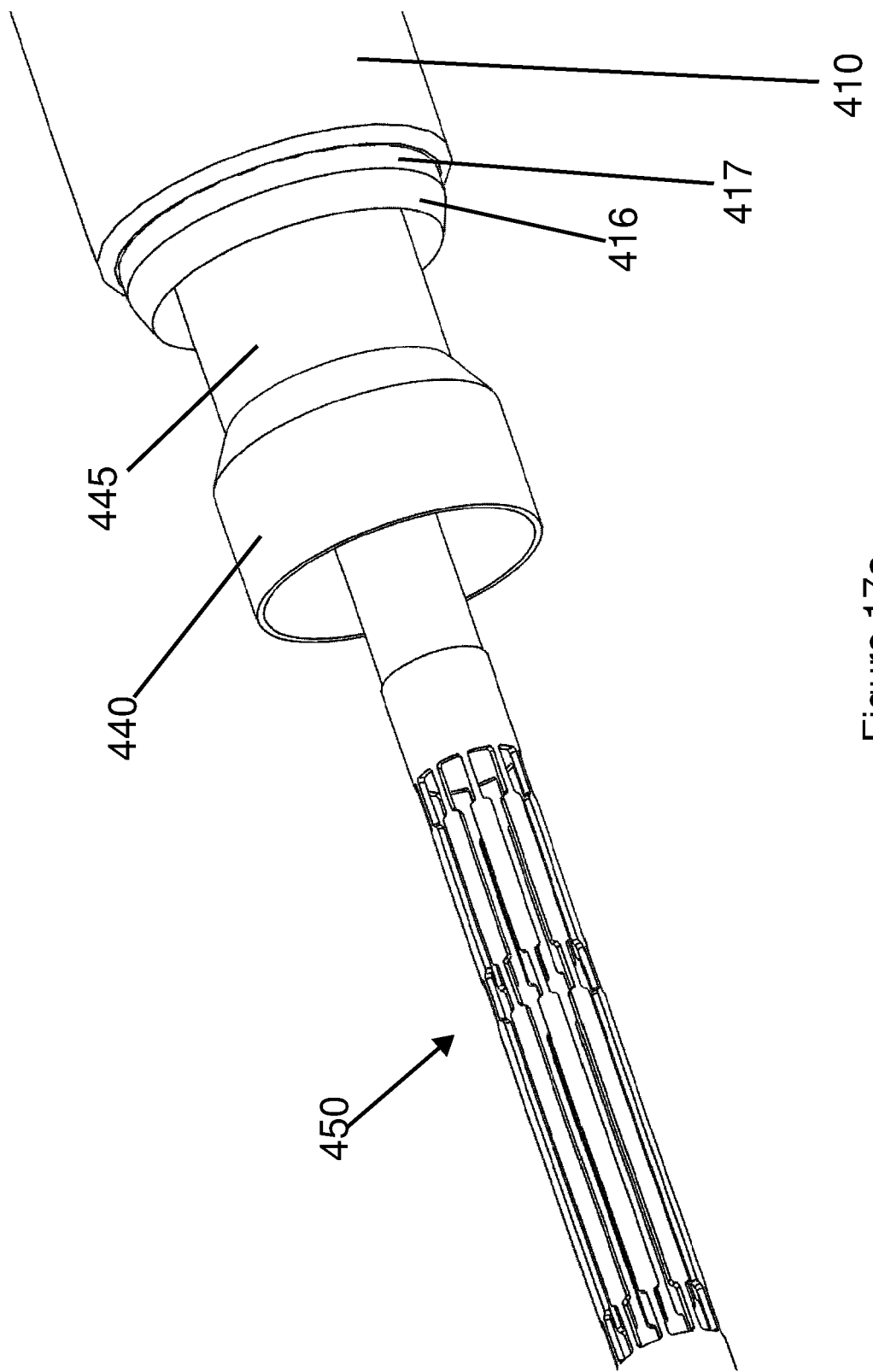
FIG. 17a is a partial perspective view of a septostomy system constructed according to the present disclosure.
Figure 17B:
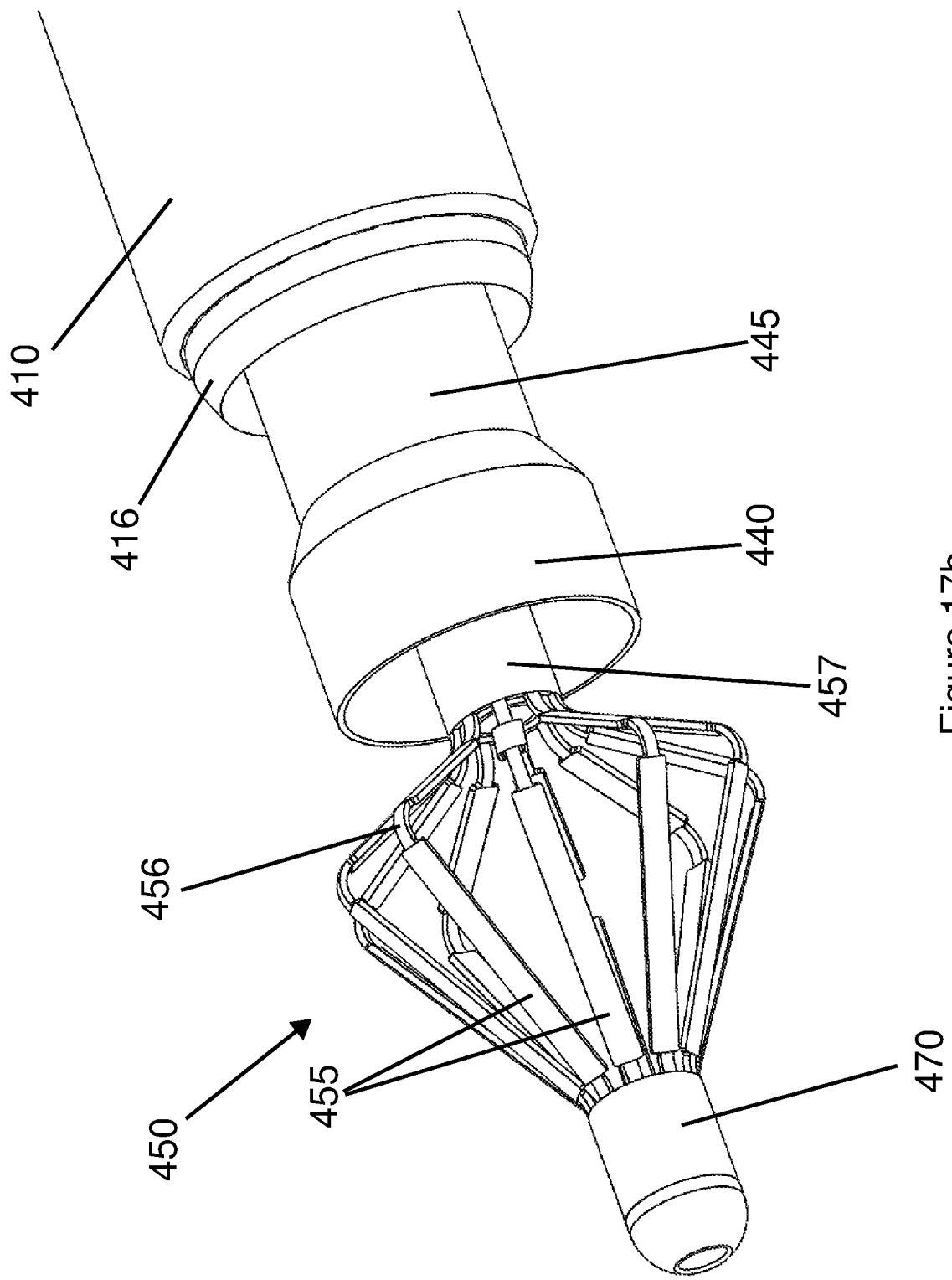
FIG. 17b is a partial perspective view of a septostomy system constructed according to the present disclosure.

As shown in FIGS. 17a and 17b in one embodiment a capture mechanism (either proximal or distal) 450 may consist of struts 455, with bend 456. In one embodiment, during delivery into the body, capture mechanism 450 lies flat on its shaft 457, as shown in FIG. 17a. In another embodiment, expandable capture mechanism 450 may be partially or wholly opened to present a cone, elongated cone, or tapered dilator with a conical distal face, as shown in FIG. 17b. The dilator then assists in the device's passage through the body to the target site, e.g., by assisting in the passage through the hemostatic valve. In the event that a portion of the device is to act as a dilator, it is useful to have its distal portion covered, e.g., by a solid surface or by a mesh to ease passage. It would be preferably reduced to its lowest diameter at or before it reaches the RA for passage to the LA.

Bend 456 may be a thinner portion of strut 455, may be formed of different material, or may be otherwise biased outward, e.g., by a shape memory material such that it is nominally open, or pushed out by a lever (not shown) and is nominally closed absent the actuation. When capture mechanism 450 exits its sheath or catheter by being advanced on its shaft 457, it may automatically expand to a larger diameter (as shown in FIG. 17b) or it may expand upon actuation, e.g. with a pull wire. The capture mechanism 450 may have a shaft in its middle that pulls tip 470 toward shaft 457, forcing or reinforcing the expansion of the struts 455. The expansion may result in a variety of shapes. As shown, the shape may present a conical face to the tissue, tenting the tissue into the lumen of the opposite capture mechanism 440. In the alternative, capture mechanism 450 may be further opened and present a concave face to the tissue, providing all of the tissue retention force on the outside surface (and preferably at a similar diameter to that of cutter 416 which is on and the catheter 410 and fits within housing 417.

Capture mechanism 450 then works with a capture mechanism 440 to trap the tissue. As described in detail above, capture mechanism 450 is advanced or retracted by its shaft 457 to be positioned alongside the tissue. Capture mechanism 440 is likewise advanced or retracted by its shaft 445 to be positioned alongside the opposite side of the tissue. In some embodiments the degree to which capture mechanism 450 is opened is strictly controlled by preset activation. In others the physician can control the degree of opening, and thus the cut to be made. The capture force placed at the perimeter of the tissue to be cut by the proximal and distal capture mechanisms of the tissue is ideally over the entire circumference of the tissue, and at a minimum of 4 points over the circumference.

The septostomy system 10 may further include one or more handles, such as cutter shaft handle 120 and capture shaft handle 220. One combined handle is contemplated as well, and it would perform each of the functions herein attributed to the two handles.

As shown in FIG. 18 the cutter shaft assembly handle 120 is preferably affixed to the proximal ends of both the outer cutter shaft 130 and the inner cutter shaft 190 (not shown). The handle 120 contains a tip deflection actuator 124 for controlling the orientation of the distal tip of the septostomy system. In one embodiment, the tip deflection actuator 124 controls a pull wire in the inner cutter shaft 190 to deflect the distal tip of the assembly. The cutter shaft handle 120 also contains a cutter knob 122 meant to rotate the cutter blade 140, e.g., though rotating one of the catheter shafts such as shaft 130.

Both the proximal capture shaft and the distal capture shaft are attached to one or more capture shaft assembly handles 220, where the proximal capture mechanism and the distal capture mechanisms are controlled. This control consists of opening them, advancing them, retracting them, capturing tissue, as required. The capture shaft assembly handle has at least one actuator for adjusting the distal end such that one or more of the capture assemblies is opened, either by moving a slider to open the capture mechanism, or causing the capture mechanism to exit a retaining means.

In a preferred embodiment, the handle 220 has three actuators. A proximal capture knob 222 operates to advance and retract the distal end of the proximal capture mechanism relative to the housing and the distal capture mechanism. The capture shaft assembly handle has a distal capture slider 226 for advancement and retraction of the distal capture mechanism relative to the proximal capture mechanism. This distal capture slider 226 is used to push the distal capture mechanism 250 across the fossa ovalis in a closed configuration and then later retract it to capture tissue while in an open condition. This distal capture slider 226 can advance distally all three distal capture assembly shafts. In one version of this embodiment, at approximately 1 cm of advancement one shaft stops advancing and only the two inner shafts continue to advance. For example, the outer distal capture mechanism shaft 260 stops advancing, allowing the distal capture mechanism to slowly come out of this retainment tube and expand into its free form state, as previously described. After this point continuing to move the distal capture slider knob forward only advances the middle distal capture shaft which is attached to the proximal end of the distal capture mechanism 250. This continued movement places a spring loading tension prior to locking the capture mechanism in this tensioned condition. This spring loading comes from a tensioning spring between distal capture slider 226 and the middle distal capture shaft 270.

Continuing to advance the distal capture slider 226 to its full extent brings the slider to a locked open position placing a spring loading on the distal capture mechanism 250 such that the distal end of the distal capture mechanism is pulled tight to its proximal end, making it very ridged and able to hold a substantial force. Alternatively, this spring loaded rigidity in the distal capture mechanism can be achieved with retracted spring loaded tension of the inner distal capture shaft, as it begins to be retracted for capture. Either way, once the distal capture mechanism is in its locked open position the slider will remain locked while retracting the distal capture mechanism toward the proximal capture mechanism to obtain tissue capture. After the distal capture slider is retracted enough to make contact with the tissue further retraction places a spring loading on the capture system, and yet further retraction brings the capture to a locked position at some spring loaded capture force, automatically locking the captured tissue in a nominally locked condition such that a special tool is required to unlock the device so tissue cannot be inadvertently lost after cutting.

In one embodiment slider 226 is attached to the most inner shaft (having a guidewire lumen) and is operably attached to the distal end of the distal capture mechanism. During deployment it is pushed forward to help keep the distal capture mechanism in a collapsed state. Prior to tissue capture slider 226 is pulled proximally toward slider 224 to maximize the distal capture mechanisms outside diameter and make it relatively tight or incompressible longitudinally and radially, such that when sliders 226, 224 are pulled back together (both attached to the distal capture mechanism) they pull the distal capture mechanism toward the proximal capture mechanism placing a capture force on the tissue. The slider 224 is attached to the shaft riding coaxially over slider 226, and is attached to the proximal end of the distal capture mechanism. It is pulled back during the distal capture delivery, and advanced forward to open up the distal capture mechanism, tighten it, and capture tissue.

In a preferred embodiment there is a spring loaded locking mechanism between slider 224 and slider 226, such that when the distal capture mechanism is open, it is locked open. The lock is spring loaded though, so when the captured tissue is being pulled into the tissue capture mechanism the distal capture mechanism can reduce in diameter, keeping the tissue captured, and therefore, reducing the diameter of the tissue. Slider 222 is attached to the proximal capture mechanism and also has a spring loaded lock to the other two mechanisms, to keep the tissue captured, but only to the spring loaded force, such that as the device reduces in diameter it holds the tissue.

The present invention further provides the operator with the ability to debulk the tissue before removing it from the body. In particular, a shunt large enough to treat many conditions would create a large tissue sample that must be safely removed from the body. Preferably, that tissue is removed using the downsized or smaller catheter of the present invention. For instance a 8 mm shunt in a 2 mm thick fossa ovalis may be prescribed. The fossa ovalis can be thick or fibrous. If this tissue is folded with the center of the tissue being pulled into the catheter first and the outer perimeter pulled into the tissue capture housing 192 last—the tissue area pulled into the housing last will be 50 mm squared, and potentially necessitate a tissue capture housing inner diameter of 8 mm or 24 French. The corresponding catheter shaft OD would of course be larger than 24 French. To reduce the diameter of the catheter components and the catheter, the inventors have discovered that the tissue can be folded differently, the tissue can be stretched or elongated, the tissue can be compressed, the tissue can be desiccated, the tissue can be vaporized, the tissue can be dissolved, and or the tissue can be cut or ground into smaller pieces.

The basic capture mechanism designs disclosed may be used to deploy means of tissue vaporization or partial tissue vaporization, either as an alternative to the cutter, or to be used along with the cutter. In this version of the device the capture mechanism 240, 250 is used to stabilize the catheter on the boundaries of the tissue to be removed and or vaporized. The capture mechanism may be used to hold and deploy the vaporization means in part or in full. The vaporization means can be fiber optics connected to a laser source, such as those sold by Spectranetics for vessel thrombectomy, or the vaporization means could be a plurality of electrodes 248, as in FIG. 6, attached via conductors to a radio frequency source, such as those sold by Baylis Medical for delivering guidewires across the cardiac septum. An example of such a structure may be similar to FIG. 6, where the proximal tissue contact surface of the distal capture mechanism contains a plurality of platinum radio frequency electrodes, all attached via electrical conductors to a RF energy source. The electrodes may be arranged in bipolar fashion across their surface or be paired to electrodes placed on the opposite side of the captured tissue. The electrodes may also be operated in a unipolar fashion, where the ground return electrode is any metallic structure attached to or in the patient, such as the other capture mechanism.

It is anticipated that such a design may be commercialized with a suction or irrigation system to remove or facilitate removal of vaporization gases, thrombus, vaporized cellular tissue, and other undesirable materials from the body. Low pressure or suction may also be used to pull and stretch tissue.

Such a design may be used to vaporize a sufficient amount of tissue such that a mechanical cutter is not needed. That is, all the capture tissue is vaporized, or it is only completely vaporized at the most outer perimeter such that the captured tissue is free from the surrounding tissue, in which case the tissue in the middle of the capture mechanism may be still vaporized further such that its bulk is reduced sufficiently that whatever remains may be controlled in a way which can be extracted through the patient's puncture site.

Some capture force, and possibly barbs 247, may be applied over various portions of the surface of the tissue capture mechanisms, or at only the capture perimeter, or at the capture perimeter and center surfaces of one or more capture mechanism. The barbs are so placed so that while the tissue capture mechanisms reduce in diameter and elongate to fit into the tissue capture housing the barbs and capture mechanism also help elongate the tissue as it and they are pulled into the catheter and housing such that more tissue volume and cross-sectional area can be fit into a smaller French size catheter, making the medical procedure less invasive. For example, a barb or circle of barbs midway along the radius of the proximal face of the distal capture mechanism would help pull the tissue in and stretch the tissue as the distal capture mechanism contracts and stretches along the shaft's axis. Various barb patterns are contemplated, such as a random pattern or checkerboard pattern. The stretching and elongation of the tissue can be done with the inner diameter of the tissue being elongated toward the proximal end of the catheter or the distal end, for example, or the tissue being elongated in both proximal and distal directions.

In the case where the cross-sectional area, folded or unfolded, of the captured and cut tissue is larger than the cross-sectional area of the inside diameter of the catheter, the inside diameter of the blade, or the cross-sectional area of the tissue capture housing, the captured tissue may need to be pulled into a smaller cross-section by stretching and compressing it. One means to accomplish this is by pulling the tissue capture mechanisms with the captured tissue into the tissue capture housing while holding the tissue tight between the capture mechanisms at the tissue perimeter. Forcing the captured tissue perimeter into a smaller diameter also forces the tissue to elongate within the tissue capture mechanisms to reduce the captured tissue cross-sectional area to be cut.

In one embodiment both proximal and distal capture mechanisms may elongate to in turn elongate or stretch the tissue to make it thin enough to fit into the housing. It is important that the distal and proximal capture mechanisms are designed to work in collaboration, such that they hold a spring loaded capture force between them while they are reduced in diameter, not losing capture force on the tissue. Instead of using a tensile force on the tissue to elongate and compress the tissue to reduce its cross-sectional area, the septostomy system can instead be designed to place only a radially compressive force on the tissue, or only a tensile force on the tissue. Such a radially compressive force device can be made from tissue capture mechanisms which forcibly shrink in diameter themselves after capturing tissue, without being pulled into a tissue capture housing. This can be accomplished, for example, with a braided wire structure by forcibly elongating it.

An additional method of reducing the tissue cross-sectional area is to debulk it by desiccating the tissue prior to extracting it from the body. The desiccation involves removing water from cellular tissue by heating it through the direct or indirect application of various heating sources such as thermal convection, radio frequency energy, ultrasound energy, or light energy. The speed of tissue desiccation will depend on the energy level, heat transfer coefficients, and time of application. At high enough energy levels these sources can vaporize the tissue, turning most of the water into a gas, in which case suction may be used to remove the gas from the body. As an example, electrodes 248 may be placed on the proximal and distal capture mechanisms at or near the circumference of the most outer capture perimeter and may be configured to contain electrodes in a bipolar or uni-polar configuration, which may deliver a high voltage charge to the captured tissue in order to vaporize and or desiccate the tissue to both cut it free from surrounding tissue and to reduce its cross-sectional area.

The electrodes could operate in various orders, and are preferably individually addressable, though a single electrode or electrodes addressable as a group are also contemplated. For example, an emitting electrode may first operate in a bipolar fashion with a receiving electrode directly across the fossa ovalis from it. This would desiccate or vaporize the tissue between these two electrodes. If needed, the emitting electrode could then alternatively form a bipole with a receiving electrode directly to the right of the first receiving electrode, and then with the receiving electrode directly to the left of the first receiving electrode. Doing so broadens out the tissue area that is either vaporized or desiccated, completing the cut or the desiccation, as applicable. If this process is continued, where the first emitting electrode pairs with successive receiving electrodes, and if needed a second emitting electrode does likewise, etc., the majority of the tissue may be either desiccated or vaporized, as applicable. An example of an RF ablation generator which can vaporize or desiccate fossa ovalis tissue is the RFP-100A RF Puncture Generator sold by Baylis Medical.

This location of electrodes is also the location where the highest force is placed on the tissue from the capture mechanism. The electrode(s) may be small and multiple or a single electrode over the circumference. The electrode(s) may be used to only desiccate tissue to reduce its cross-section before or during being pulled into the tissue capture mechanism. The electrodes could alternatively be mounted to the distal end of the tissue capture housing, such that it acts as the tissue cutter by vaporizing the tissue, and it is also the means for debulking the tissue to bring it into the smaller French size catheter. This dual purpose vaporization source for cutting and debulking on the distal end of the tissue capture housing may be laser energy supplied via fiber optics, LED's or similar devices. Alternatively the laser source may be used to only debulk the tissue or only cut the tissue.

The described energy, such as RF electrodes at the cutting perimeter may be used to necrose or kill the cellular tissue of the fossa ovalis tissue to be cut, or near the tissue to be cut, prior to, during, or after cutting the tissue. This may provide for a reduced amount of healing and shrinkage of the shunt, and thus allow for a smaller cut from a smaller catheter. One preferred embodiment may be to necrose the tissue at the perimeter tissue capture location with RF energy after the tissue is captured, but before it is cut from the atrial septum. In this embodiment the tissue highly controlled and the RF energy is applied directly to tissue which will be removed from the body, along with any thrombus which may occur during ablation. The RF energy is applied directly near the tissue to be cut however, such that the heat effected zone sufficient to cause necrosis and reduced healing effect may be tuned to be within the tissue cutting zone. Laser light energy, cryogenic fluid, heated fluid or other means of applying necrosing thermal effects may also be applied in a similar fashion. Other means for causing localized cellular death to the region to be cut may also include irreversible electroporation, drug injection or elution to the capture perimeter with drugs like paclitaxel and everolimus, or alcohol ablation, high mechanical force, ultrasound, microwave energy, or other electromagnetic energy, all placed at least at the capture perimeter, to cause cellular death at the location of the tissue to be cut.

Desiccating or vaporizing electrodes can be located elsewhere as well. For example, with respect to FIG. 15, electrode 295 can be located on a central shaft, or on an auger 290. In such a position the central electrode 295 will desiccate or vaporize central tissue as its drawn to or over the electrode, either by cutting from auger 290 or by stretching from the capture mechanisms. As above, the electrode 295 may act unipolarly or bipolarly, e.g., with electrodes 248. In addition, there may be an additional ring of electrodes 248 that are more centrally located, e.g., on the proximal face of the distal capture mechanism 250 (see FIG. 6).

The fossa ovalis tissue can also be mechanically debulked or reduced in cross-sectional area. An example mechanism is a distal capture mechanism 250 made of a laser cut tube. See FIG. 8c. The proximal capture mechanism may also be a laser cut tube as described here. The tube is slotted on its proximal face such that when it is opened to capture tissue the slots become diamond shaped. The inside edges of the diamond shape can be sharpened to cut tissue. When the tissue and capture mechanisms are pulled against and then into the tissue capture housing the sharp edges of the diamond shape slots move into the housing faster than the main capture location at the perimeter of the captured tissue such that the tissue is cut into small pieces and pulled into the catheter shaft, extending the tissue over a longer portion of the inside diameter of the catheter, allowing a smaller catheter French size to be used to cut a larger diameter of tissue. In such a design the distal capture mechanism 250 may be elongated to allow for more sharpened cutting surfaces to be pulled into the catheter shaft, as needed, and therefore debulking more tissue.

The mechanical debulking component may also be a device separate from the distal capture mechanism, or act as a multi component distal capture mechanism as shown in FIG. 15. The mechanism may incorporate a small auger 290 or similar cutting mechanism which rotates over the distal capture shaft, cutting tissue and moving it into the proximal shaft. FIG. 15. The auger may also have an electrode 295 to desiccate the tissue as its cut. The auger could have a sharp metal blade, and be accompanied by a saline irrigant or a vacuum to help move cut tissue proximally and out of the capture zone. Such a design can cut the captured tissue and move it proximally into the shaft as the capture mechanisms reduce the tissue diameter and force the tissue onto the blades for cutting. With such a design the distal and proximal capture mechanisms only needs to capture the tissue at the outer capture perimeter and forcibly reduce the perimeter diameter, forcing tissue onto the auger debulking mechanism, which cuts and removes the tissue from the inside diameter. The auger cutter can use a sharp edged blade, an RF blade, a laser cutter to separate tissue, or. combination.

Instead of an auger 290 to move tissue proximally the separated tissue can be moved proximally into the shaft of the catheter with a linear cutting device, or a suction type device. A linear cutting device may simply be a cut metal tube on distal capture mechanism 250, shaft 260, or a similar location which has sharpened inner edges which are able to cut and separate tissue as it is pulled into the end of the catheter shaft or tissue capture housing. Ideally when the debulking is being performed with or without a mechanical means of moving tissue proximally a suction may be applied to the catheter shafts thru a valve on the proximal end of the catheter shafts. This suction helps move tissue proximally into the shaft making room for more tissue, as well as helps prevent vapor from desiccation or vaporization from entering the blood stream. An example of such a pumps is the Indigo by Prenumbra Inc. Suction may also be used as the primary means of elongating tissue, without separating it into pieces. That is, a high suction force may be placed on the captured tissue pulling it and elongating it into the catheter and therefore reducing its cross-sectional area.

Figure 19:
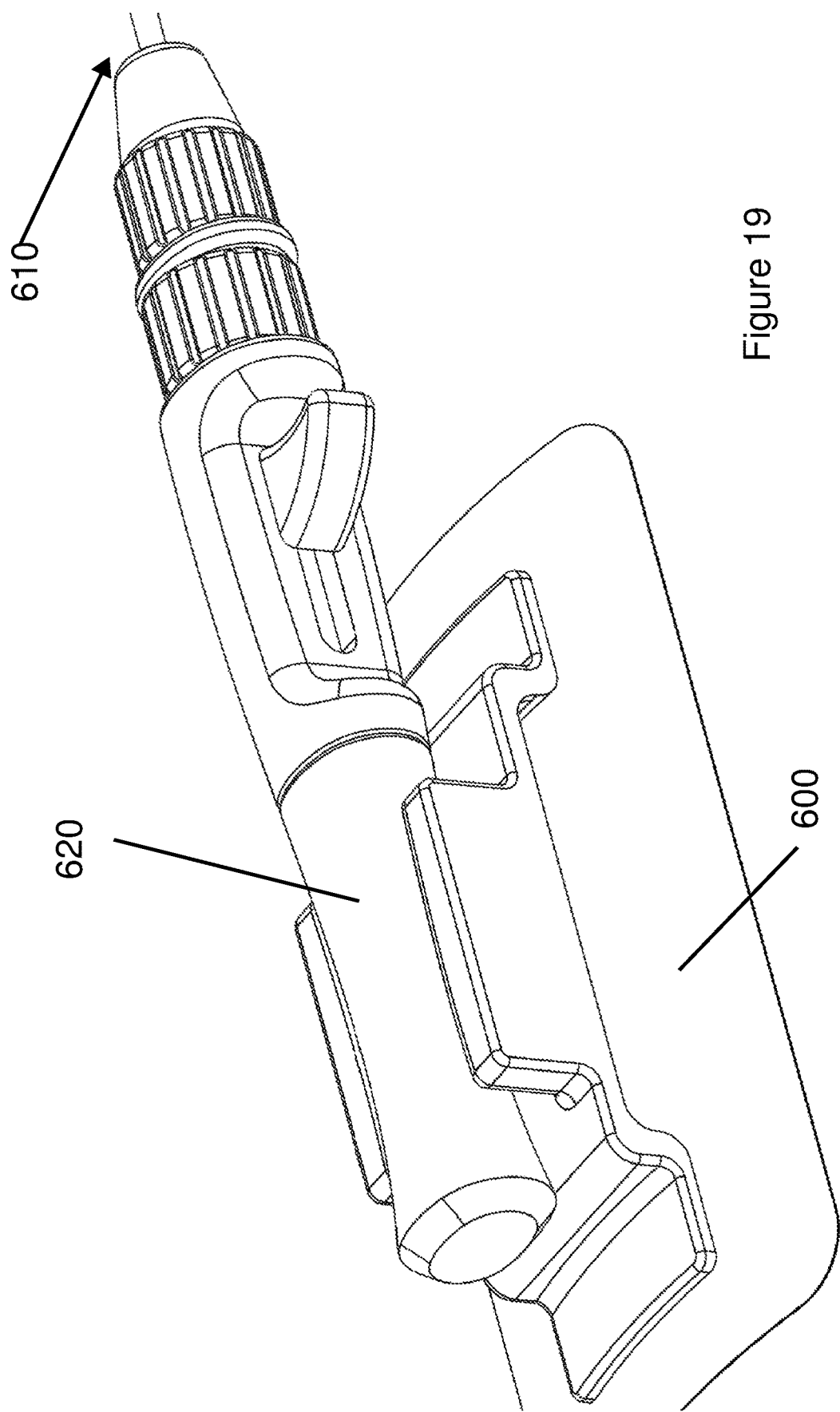
FIG. 19 is a partial perspective view of a handle and stabilizer for a septostomy system.
Figure 20:
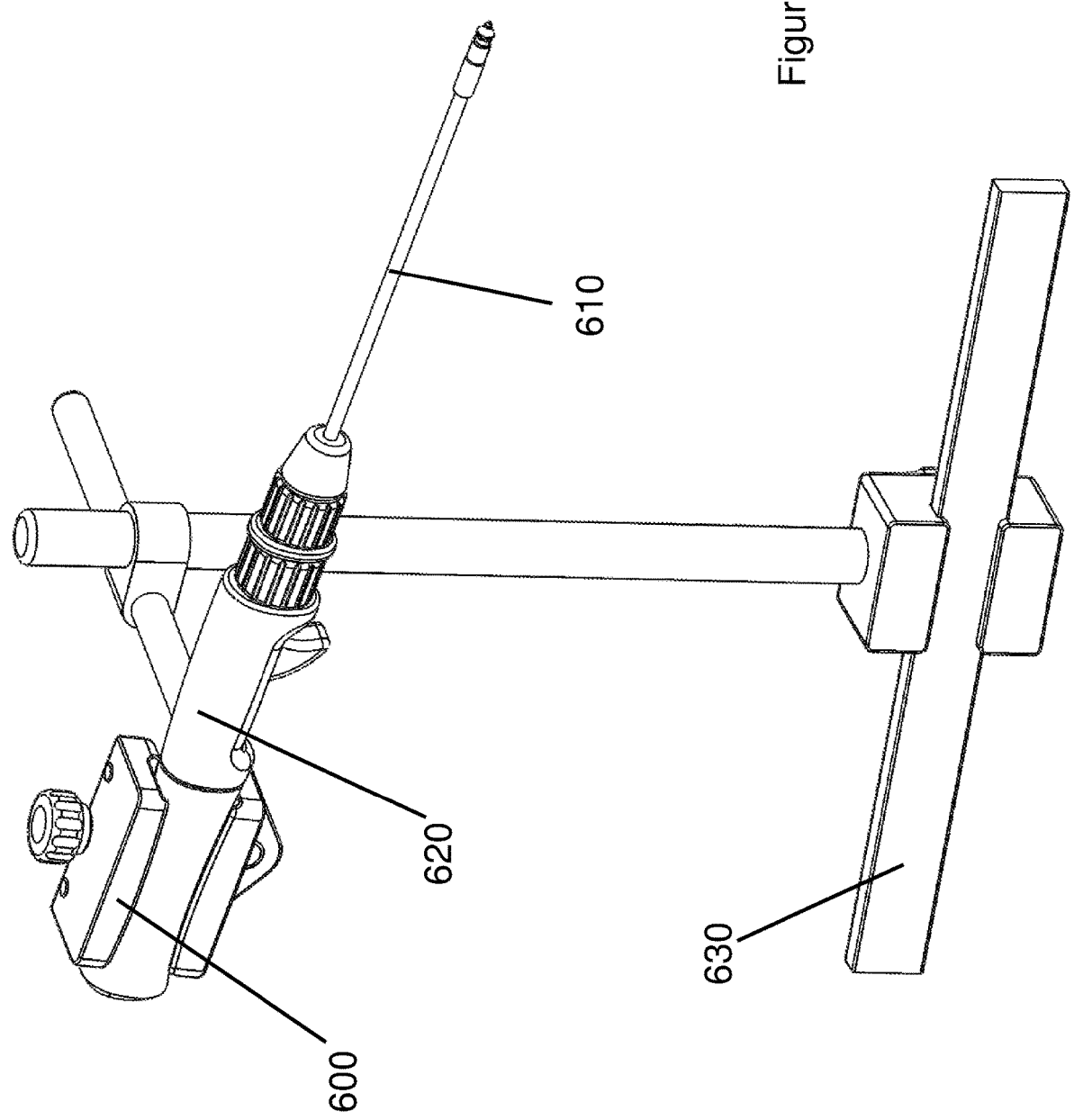
FIG. 20 is a partial perspective view of a handle and stabilizer for a septostomy system.

To optimize the shunt shape and size it is important to minimize the movement of the tissue capture point after device alignment, during capture and during cutting. This can be done by fixating the system at any point from proximal to distal. This is especially important after the blade or capture mechanism alignment just prior to capture. However, movement of the system after capture can still cause improper shunt shape and size if the loading force on the fossa ovalis tissue is sufficient to pull tissue from the capture point. Fixation of the system should control torque, advancement and withdrawal of the system relative to the distal end. The most efficient and safe way of performing this catheter fixation is to as solidly as possible attach the system outside the puncture site to the patient, as shown in FIG. 19. Because good fixation at the fossa ovalis is ideal for achieving an ideal aperture, good fixation outside the body is also ideal. One way to do this is to adhesively attach a septostomy hub to the patient as close to the puncture site as possible. This hub 600 can securely grasp a handle 620 or shaft 610. If the patient moves the hub 600 and shaft 610 will move with the patient, but the relative movement of the catheter distal tip with respect to the fossa ovalis will remain fixed. Alternatively, since the patient is sedated and generally does not move during the procedure, the shaft 610 or handle 620 can be fixed by a hub 600 to the bedrail 630 or similar, as shown in FIG. 20 to keep it from moving. To facilitate the latter the patient's leg can furthermore be fixated to the bedrail to keep movements minimized.

After the catheter if fixated any remaining in-plane bias is preferably removed. This in-plane bias is a result of the catheter at the fossa ovalis crossing point being biased in-plane such that it slightly elongates the hole in the tissue which it is crossing through, as evidenced by high velocity blood jetting on doppler (TEE, TTE, ICE). The catheter shaft is preferably aligned in the fossa ovalis plane such that jetting as seen on doppler is minimized. This is done by torqueing the catheter shaft, and if not preshaped, also actuating pull wires to deflect the distal tip. By minimizing blood jetting alongside of the catheter the shaft is brought into its original crossing point and in plane catheter shaft bias is removed. This will allow for a more accurate shunt shape and size. The tissue capture housing 192 described above may also act as a proximal capture mechanism 240, as it may, working in conjunction with the distal capture mechanism 250 place perimeter capture force on the tissue prior to cutting. In this configuration the tissue capture housing may be expandable to the same diameter as the distal capture mechanism, capture tissue, then contract with the tissue to the cut diameter, or the cutter can expand with the tissue capture housing and cut the tissue prior to being contracted into a smaller diameter. Either way both configurations allow for a shunt diameter larger than the diameter of the catheter diameter.

Figure 21:
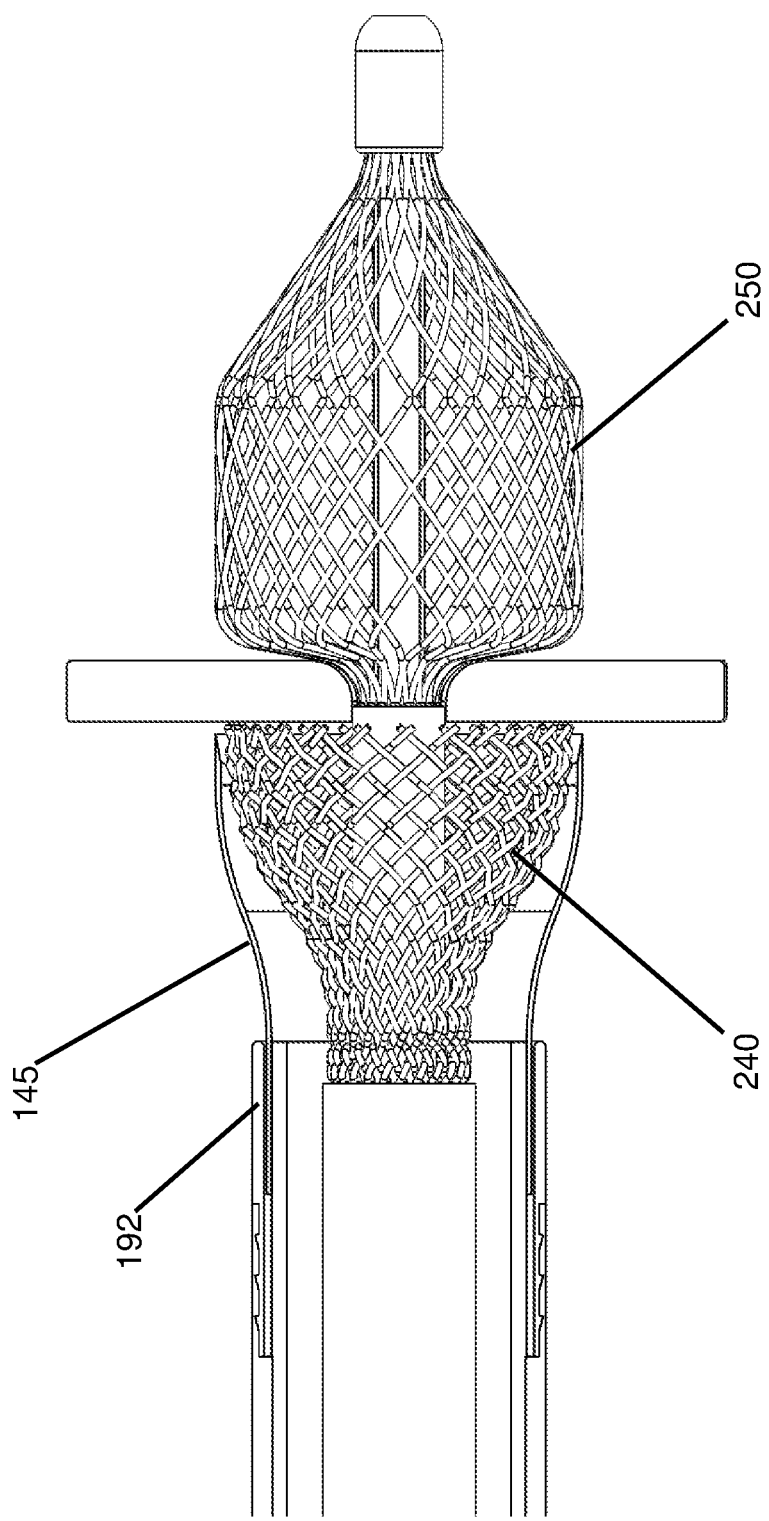
FIG. 21 is a partial perspective view of a septostomy system constructed according to the present disclosure capturing a portion of the septum.

Alternatively, the components of the inner capture shaft and outer capture shaft are reversed so that the cutter is on the ID of the tissue capture housing. This may be a preferred embodiment as the outer catheter shaft would then not rotate. In order to cut a shunt larger than the diameter of the catheter, some embodiments may need to employ an expandable cutter 145. FIG. 21. This expandable cutter 145 may work in conjunction with a tissue capture mechanism. In one embodiment the expandable cutter 145 is initially located on the outside diameter of the tissue capture mechanism 240, 250. In another the expandable cutter 145 is initially located in tissue capture housing 192. In any case, the tissue capture housing may be also expandable or not. The cutter 145 may be a laser cut nitinol tube like the figures above, meant to be nominally open and held closed for delivery, in which case it is advanced out of a containment tube like the tissue capture mechanism and expanded. In another embodiment it is nominally closed and held open for cutting with pull wires or similar.

Figure 22A:
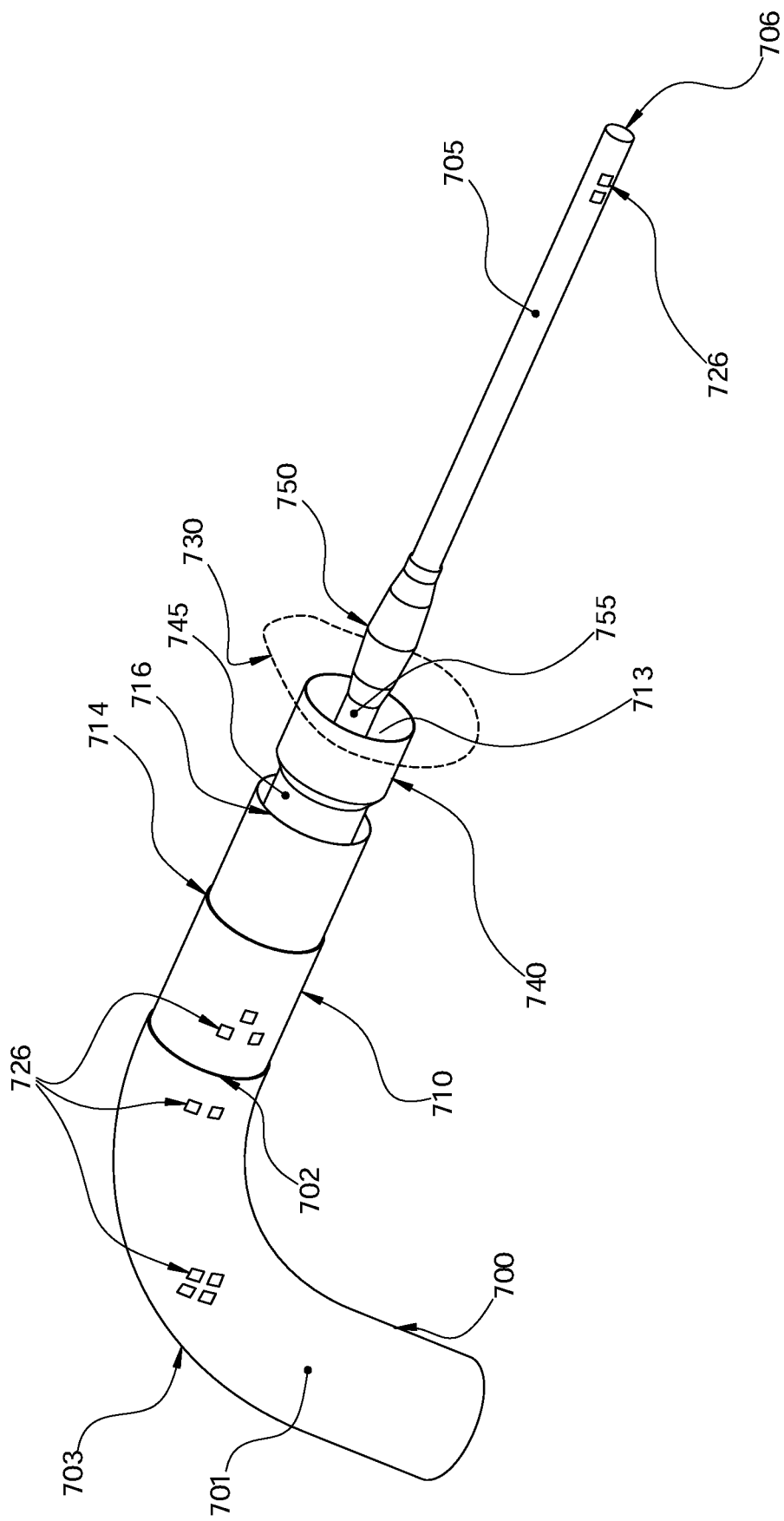
FIGS. 22a-b are partial perspective views of a septostomy system constructed according to the present disclosure.
Figure 22B:
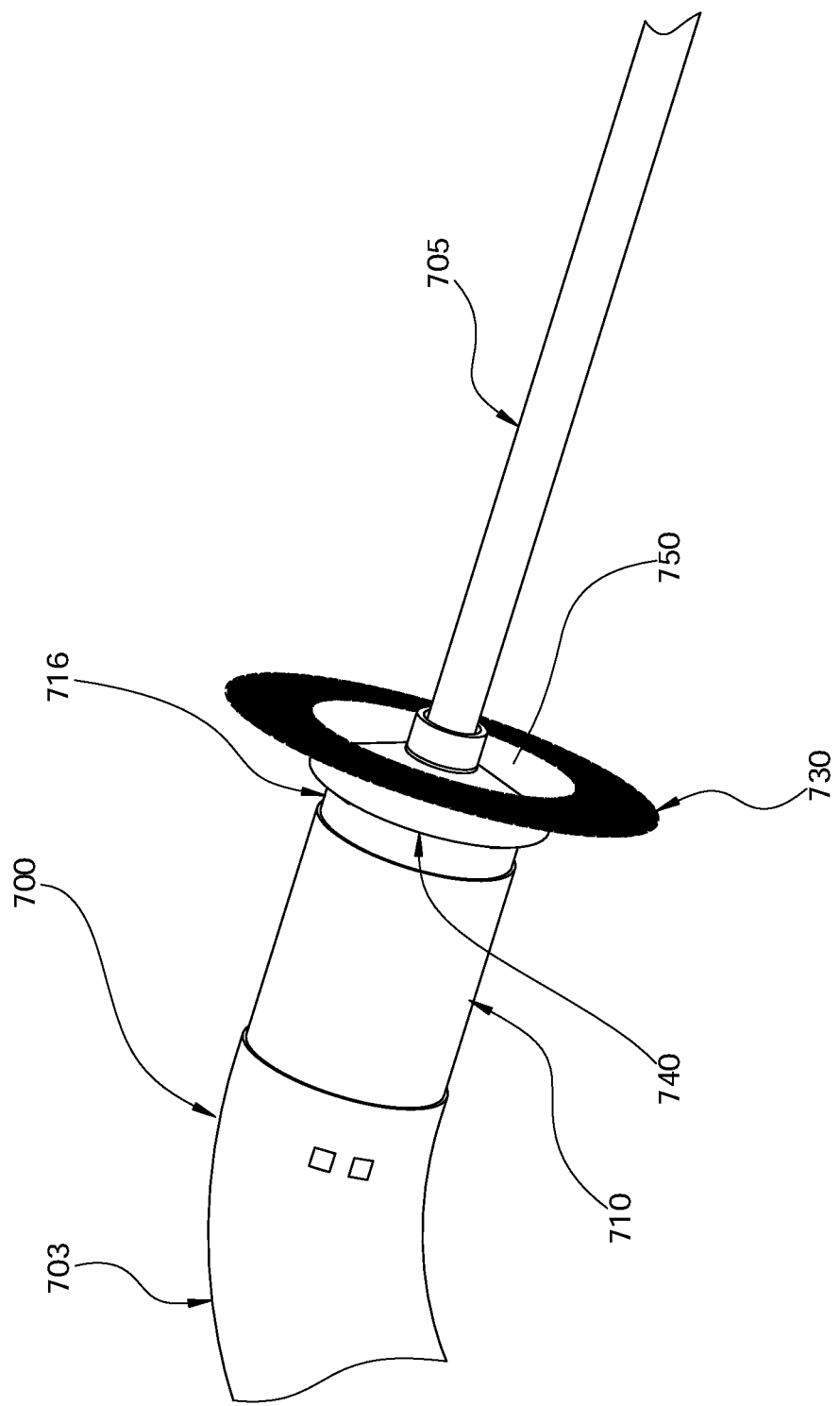

With reference to FIGS. 22*a-b*, a medical device assembly includes a sheath 700, a catheter 710, and a guidewire 705. While the following description describes the sheath 700, catheter 710 and guidewire 705 as separate devices, it is understood that they equally can be a single device, be integrally connected (but preferably laterally moveable relative to each other), and be controlled by the same or different proximal handles and electrical connections. In particular, the attributes of the sheath 700 and catheter 710 may be advantageously combined. Likewise, the sheath, catheter, or guidewire may be omitted. While at least one of the devices will need to traverse the length of the body from the entry point to the atrium, it is contemplated that the other devices may be shorter. For example, the sheath may traverse from the percutaneous entry point to the right atrium. The catheter may only traverse from one side of the right atrium to the other, for example, and as such be substantially shorter.

Sheath 700 comprises an elongated catheter shaft 701 having a distal end 702 and a proximal end (not shown). The proximal end includes a handle as described above (not shown). Sheath 700 and/or catheter 710 may further include pull wires attached to an actuator for actuating distal elements, moving a lumen or shaft, steering, or the like. Sheath 700 and/or catheter 710 may further include irrigation ports and the like.

Sheath 700 and/or catheter 710 further include visualization markers 726 designed to allow the physician to determine the location and orientation of the sheath 700 and catheter 710 in the patient and the orientation of the different components of the device relatively to each other. For instance, sheath 700 may have radiopaque markers 726 at a bend 703 in a pattern that identifies the bend region. Sheath 700 may then have further radiopaque markers 726 at its distal end 702, again in a distinct pattern that is the same or different from the pattern at bend 703. Likewise catheter 710 may have radiopaque markers 726, e.g., at its distal end. Because the catheter 710's radiopaque markers are differently patterned than the sheath 700's radiopaque markers, the physician will be able to quickly and easily identify when the catheter 710 exits the sheath 700. Finally, guidewire 705 may have radiopaque markers 726 so that the guidewire may be quickly identified by fluoroscopy as well. Preferably, the radiopaque markers 726 (or other markers) on the catheter, sheath and guidewire are distinguishable from each other and accordingly the physician is able to determine the spatial relationship of the three components. In one example, spot electrodes may be used and provide a pattern. In another example, an electroanatomical mapping system is programmed or provided with the specifics of the three components. The specific electrodes, magnetic coils, or other electrodes are identified to the mapping system, e.g., through an EEPROM in the catheter or otherwise, and as the system identifies a specific electrode or coil (e.g., by the current passed through the electrode or coil and to the other components of the mapping system). The mapping system may then clearly and visually identify the location of the three components for the physician.

Advantageously, the sensors may enable the operator to create an electro anatomical map of the right atrium and left atrium. This map can include details such as tissue thickness, especially in the fossa ovalis or the septum. The maps can also be created or supplemented by fluoroscopy, or an imported map such as a CT scan, MRI, live external modalities like TTE, TEE, or information from live on-board catheter sensors, like OCT, ultrasound, CCD camera visuals, for example, to understand the surface morphology, tissue thicknesses, tissue compliance, location of PFO/flap, etc. These live modalities maybe also used independently. For example, the live on-board catheter sensor(s) may be an OCR sensor for imaging the tissue to be cut. This design might also incorporate a live on-board catheter sensor, which is an electrode to keep cutting away from nerve, SA node artery, or for impedance tissue thickness measurements, as examples.

Sheath 700, guidewire 705 and catheter 710 may alternatively or further include ultrasound markers (not shown) or hyper-echogenic markers, again preferably in designed patterns as described above such that the physician may locate the components in the patient on ultrasound imaging. In an alternative embodiment, in place or in addition to radiopaque markers 726, the sheath 700, guidewire 705, and catheter 710 may have electrodes (not shown) that are locatable on an electroanatomical mapping system such as the EnSite™ electroanatomical mapping system. Alternatively, the sheath 700, guidewire 705, and catheter 710 may have magnetic coils locatable on the Carto™ or Medi-Guide™ mapping systems.

The elongated shaft 701 is preferably hollow, having a lumen 713 that has the ability to pass the catheter 710 and guidewire 705 through it. The catheter 710 is designed to work in conjunction with sheath 700. Sheath 700 may either extend the entire length from the percutaneous incision to the left atrium of the heart, or may only cover a portion of catheter 710.

In one such embodiment, sheath 700 extends to the steering/bend 703. In another embodiment the sheath 700 may terminate before the bend 703, and as such the medical assembly is preferably steered/bent by pull wires or biasing in catheter 710. However, in another embodiment, the sheath 700 terminates distally of bend 703. Pull wires or biasing in the sheath 700 enable it to make a sufficient turn to orient catheter 710 toward the interatrial septum 730 and thus the sheath exit and orientation provide an orthogonal guide to the catheter. If the sheath is then locked in place, e.g., via a catheter hub (FIGS. 19, 20) its bend 703 can operate to prevent catheter 710 from moving upward in the RA. While in one embodiment the catheter 710 does not have its own biasing or pull wires, in another embodiment the catheter 710 may be separately steerable or biased, and thus provide for the orthogonal approach. Pull wires provide the advantage of minute adjustments to the specific anatomy of the patient, and allow for greater flexibility in the device. One device may be used for nearly all patients and still provide a proper approach angle.

In another embodiment the catheter is controlled by steering the distal tip with a magnetic field. Remote magnetic navigation operates by, for example, using two large magnets placed on either side of the patient, and alterations in the magnetic field produced by the magnets deflects the tips of catheters within the patient to the desired direction. The physician operates the catheter with screen and a joystick. The catheter itself is advanced by the joystick, instead of the physician's hands. Likewise, while a physician may operate the medical devices disclosed herein by hand, the devices may be robotically driven. As with magnetic navigation, the physician operates the catheter with a screen and a joystick. In another embodiment, providing a biasing agent such as a nitinol wire to provide a preformed bend provides the advantage of having a less expensive manufacturing process and a simpler device. However, multiple bend sizes may need to be manufactured.

In another embodiment, the sheath 700 may have a first preformed bend, and the catheter 710 may have a second preformed bend. The first and second preformed bends work together to allow the operator to direct the cutting blade 716 to the septum at a right angle. Likewise, the catheter 710 may have multiple preformed bends. For example, a catheter 710 may have a first and second catheter preformed bend, such that for a smaller atrium only the first bend exits the sheath 700, and with the sheath's orientation, the first bend directs the distal end of the catheter to where the fossa ovalis typically sits for a small heart with smaller chambers. For a larger heart, however, as the catheter 710 must exit farther out of the sheath 700 the second catheter bend also exits, and realigns the distal end of the catheter toward where the fossa ovalis typically sits for a larger heart. Likewise, the assembly may include a removable stiffener that can be deployed to adjust the distal tip's location to provide a right angle approach to tissue 730.

The sheath 700 and the catheter 710 may include braiding to provide stiffening. Unlike prior art devices which create a hole by energy sources or by implanting a device, the present device may find that significant pressure is necessary to create the aperture. Because the pressure must be transmitted from the length of the sheath or catheter that pressure will initially push the cutting edge and the entire catheter along rather than through the septum. For example, in a femoral vein entry procedure, the catheter is initially pushed upwards in the RA rather than towards the left atrium. Accordingly, unlike the prior art the applicants have discovered that providing stability and steerability in either the sheath or the catheter may greatly reduce this upward pressure and redirect the force towards the interatrial septum 730 to provide a proper cut. In particular bend 703 and the adjacent shaft may require a stiffer shaft than the remainder of sheath 700.

Toward this end, sheath 700 is used to create bend 703 and direct the catheter 710 to the septum 730. Sheath 700 terminates just distally of the bend 703. At this point, in one embodiment the sheath 700 is held in place as catheter 710 is advanced out of the sheath 700 to the septum 730. Because the sheath 700 is sufficiently stiff, it resists the upward pressure and directs the catheter force toward the interatrial septum 730. Together or in place of the sheath, the device contemplates providing anchoring means or stabilizing means (not shown) to prevent the catheter and the cutting blade from shifting and thus allowing a clean cut in the desired location. Sheath 700 and catheter 710 may further include irrigation ports (not shown).

Regardless of the tissue removal or retention means, it is advantageous to include a tissue collection device. For example, the catheter may include a lumen or compartment at the distal end to retain the tissue. Likewise, under suction the device may include a tissue trap, such that fluid, blood, or other material may pass, but tissue is retained in the trap. The physician then may monitor the trap to determine that the tissue removed from the septum has been captured, and is not still in the heart. Such a monitoring may be automatically provided, or may be manual by the physician. It is advantageous if such monitoring can be conducted before the catheter is removed from the patient, and as such in one embodiment the trap is exterior to the body and readily accessible by the physician. In another embodiment, the trap is automatically monitored by a sensor, such as an electrode, visual examination, pressure sensor, or the like for the presence and volume of tissue. In another embodiment the trap is removed for examination first, before the introducer and catheter are removed.

Once the cutting means 716 or the catheter 710 are located next to or near the target tissue 730 the catheter 710 and/or the cutting means 716 are advanced past the end of or to the end of the sheath and placed in contact with the tissue 730. Preferably using the unique markers the physician can tell on the visualization system when the catheter has exited the sheath 700 or has contacted the tissue. Likewise, the catheter 710 or the cutting means 716 may include sensors (not shown) that identify when it contacts the tissue, at what angle it contacts the tissue, the thickness of the tissue, whether it is through or not through a PFO or a flap, if the cutting is complete, the quality of the cut edge, and the like. Such sensors can include a force sensor, fiber optics, a camera, and electrode using impedance sensing, mapping systems, ultrasound, or the like. Likewise, the physician may monitor a visualization system to determine when the tissue begins to tent to determine when contact is made. In a first embodiment, the circular cutter 716 is advanced into the tissue 730 to cut a circular aperture in the tissue. In an alternative embodiment the sheath 700 is not utilized and the catheter 710 itself is steered into position near tissue 730, and the cutting means 716 is advanced to cut the aperture.

In another embodiment the medical device assembly includes a tissue capture component. For example, as shown in FIG. 22a, the assembly may include a distal capture component 750 designed to cross the septum to the distal side. The distal capture component may be attached to the guidewire or second catheter 705, the sheath 700, or the catheter 710. It may also be attached to a distal capture catheter 755. As such, distal capture catheter 755 may have a lumen and ride over the guidewire 705, but inside a lumen of catheter 710. Such a lumen may be just large enough to fit over a 0.035" guidewire. Distal capture catheter 755 may be advanced by an actuator, or have its own handle. If the distal capture component was not expandable, but instead a tapered shape like a dilator, the tissue will tear or expand when being crossed such that the subsequent capture of tissue may be less than ideal. An expandable distal capture mechanism 750, as shown in FIGS. 22a-b, will provide reduced tearing.

This distal capture component must also provide high capture forces when it is expanded, so tissue does not slip from the capture area, providing accurate shunt size and shape. Furthermore, for safety reasons the expandable distal capture mechanism failure mode ideally defaults to open. This means the device is ideally naturally self-expanding after it exits a flexible retention tube. Finally, the capture mechanisms preferably place most of the capture forces at the outer circumference of the captured area to minimize tissue slippage from the capture point. The devices shown in the figures above are additional options. The device may ideally be preshaped such that when it comes out of the restraining device it expands, or it may expand to its full shape when the two ends of the device are pulled together or otherwise actuated. An expandable distal capture mechanism may also be made from an expanded nitinol wire or tube form and held about the catheter axis using radial arms, balloons or similar. Alternatively, high pressure shaped polymer balloons may also be used on their own or in combination with metal expandable structures to make an expandable distal capture component.

Once on the distal side of septum 730, the distal capture component may be expanded as shown in FIG. 22*b*, and brought into contact with the tissue 730 (not shown). This may be accomplished a variety of ways detailed above.

Before the expanded distal capture mechanism 750 is pulled proximal to capture tissue the system 10 must be aligned to trap the tissue in its natural orientation. First, the proximal capture component 740, as seen on fluoro or echo is advanced such that the most distal face of the proximal capture mechanism is touching the fossa ovalis in its natural plane. To improve visibility of the proximal capture component radiopaque and/or echolucent filler is added. This will allow an in plane capture and support the accurate shunt shape and size. Next, the distal capture component, in an expanded state, is moved or actuated, is withdrawn such that its most proximal face is touching the fossa ovalis in its natural plane. Then the two devices are locked into place, with sufficient force between them to retain the tissue. The distal tissue capture mechanism may be advanced first. Ideally the catheter has a component which, while fixated, can move the capture point slightly into the LA, in a controlled manner.

In another embodiment the medical device assembly may include a proximal capture component 740 designed to remain at least partially on the proximal side of the septum 730. The proximal capture component may be attached to the guidewire 705, the sheath 700, or the catheter 710. It may also be attached to a proximal capture catheter 745. As such, proximal capture catheter 745 may ride over the guidewire 705, but inside a lumen of catheter 710. Proximal capture catheter 745 may be advanced by an actuator, or have its own handle.

In another embodiment, shown in FIGS. 22*a-b*, the assembly includes both proximal and distal tissue capture components, 740 and 750. In this embodiment the tissue capture components may be attached to the same or a different catheter or guidewire. In operation (FIG. 22*b* the tissue capture components are brought together to hold the tissue between them, both retaining the tissue in place for the cutting blade 716, and also capturing the tissue for removal (FIG. 22*b*).

Alternatively, the cutter blade 716 and cutter blade shaft 717 can be advanced over the guidewire and dilator into the RA prior to advancement of the capture components. In some embodiments it will be advantageous to control tissue capture forces for safety and effectiveness. In these cases a sensor 770, and or a strain or force sensor 780 can be attached to the capture components. In a preferred embodiment the force sensor 780 is able to determine how much force is applied to the respective shafts, e.g., force sensor 780 determines how much force is applied to the proximal capture component shaft 745, while a second force sensor determines how much force is applied to distal capture component shaft 755. By measuring these respective forces the operator is able to determine how firmly the tissue 730 is held between the components. Likewise, in embodiments with only one tissue capture component, the force sensor can identify how firmly that capture component holds the tissue. In the event that the tissue is not firmly held, the operator will be able adjust the positioning, remove the device and reapply it, or the like. Above all, the sensors on the capture component shaft can give the operator an indication of the safety of the operation. If the tissue is not affirmatively held, there is a risk it can break free creating a risk of stroke due to embolization. Accordingly, knowing how well tissue 730 is held by the tissue retention device(s) is critical. In other embodiments an actuator can apply a set amount of force between the capture components and can lock them in place.

In addition to or in the alternative to force sensors the device may comprise a sensor on the proximal capture component shaft 745, and a sensor on the capture component shaft 755. Of course, the sensors may be located on the capture components themselves as well. Sensors may be used for one or more purposes, including determining the location of the shafts or components, visualizing the tissue, visualizing the procedure, sensing the impedance of the tissue, sensing the proximity of another sensor or component, and the like. Examples of such sensors include magnets, electromagnetic coils, electrodes, optical strain sensors, electrical strain sensors, cameras, fiber optics, ultrasound, pressure sensors and similar sensors. Likewise, markers such as radiopaque markers or ultrasound markers may be employed on the shafts or components.

Typically the device types described herein work best if there is no bias, or force on the tissue in any direction other than what is necessary to capture and cut. The exception is a device used to increase an existing hole's size, in which case biasing the shaft and cutter into the side of the previous hole is necessary. In general though, if there is bias in or out of the septal plane during capture for instance, the tissue will likely be stretched over the capture components prior to capture, making the resulting hole smaller than expected. Likewise, if the bias is within the septal plane prior to capture, the device shaft will elongate or tear the hole such that the capture has minimal tissue on one side and bunched tissue on the other. If a cut is made in the latter situation, the cutter may pass through, on one side, the hole created by the bias, leaving an elongated hole. Also, if part of the cut passes through a hole stretched by bias, the tissue around the shaft will not be complete, creating an increased safety risk that would need mitigating.

To remove bias-device stability, control and feedback is needed. Stability can be achieved at least three ways. First, a distal structure attached to the outer sheath can engage the septal tissue, allowing all adjustments to be with respect to it. This frame structure may be at least partly disconnected from the proximal components to minimize unintended forces. The frame structure may consist of one or more struts extending from the catheter or sheath, designed to lean against the tissue and hold the catheter and cutter orthogonally to the tissue. Likewise, in another embodiment the structure may be a hood. A hood structure would also allow a suction to remove all blood and provide direct visualization of the septum. In another example the distal structure may be a balloon on the outer surface of the sheath, such that when inflated the balloon structure matches the contour of the septum and provides for an orthogonal guide to the sheath, catheter, or blade. In each case, the orthogonal guide is preferably collapsible for delivery into the atrium.

Second, the device, such as the sheath or catheter shaft, can be affixed securely to the patient's puncture site via a catheter holder, allowing all adjustments to be with respect to the puncture site and therefore the septum. Finally, the catheter handle can be affixed to the patient, drape, bed rail mount/platform, or similar via a catheter holder. See FIGS. 19-20.

In another embodiment, the cutting means is allowed to "float" with respect to the catheter, such that it is contact with the tissue that governs the orientation of the cutting means, rather than the orientation of the catheter. In particular, if the bottom side of a circular cutter contacts the tissue first, the cutter will pivot as it is pushed forward, for example, so that only the top portion moves forward until the entire cutter is substantially in contact with the tissue. For example, in one embodiment the cutter may be attached to the medical device via a central shaft, and spaced from the catheter via springs around the periphery, such that under light pressure from the fossa, the cutter compresses one or more springs, but does not initially compress the others, causing the cutter face to move into an orthogonal position vis a vis the tissue. As the cutter comes fully into contact with the tissue, the pressure from the catheter continues to rise and it is pushed orthogonally through the tissue.

The invention claimed is:

1. A septostomy assembly comprising:
a catheter assembly, the catheter assembly comprising:
   a catheter shaft, the catheter shaft having a catheter lumen,
   a shaped blade, the shaped blade comprising:
     a blade cutting edge that is oriented at a substantially right angle to the longitudinal axis of the catheter,
   a tissue retention assembly located at least partially in the catheter lumen comprising a shaft, a proximal tissue retention device and a distal tissue retention device, the tissue retention devices configured to apply a force between them;
   an actuator, the actuator configured to reduce a gap between the proximal and distal tissue retention devices to grasp a tissue;
   wherein the proximal tissue retention device and the distal tissue retention device apply the majority of the force at their perimeter.

2. The septostomy system of claim 1, wherein the proximal tissue retention device and the distal tissue retention device apply 60% of the force at their perimeter.

3. The septostomy system of claim 1, wherein the proximal tissue retention device and the distal tissue retention device apply 90% of the force at their perimeter.

4. The septostomy system of claim 1, wherein the proximal tissue retention device is configured to exit the catheter lumen, and further has a first cross sectional area that fits within the catheter lumen, and a second, larger cross sectional area when it exits the catheter lumen.

5. The septostomy system of claim 4, wherein the proximal tissue retention device grasps the tissue while the proximal tissue retention device is in the second, larger cross sectional area configuration.

6. The septostomy system of claim 5 wherein the proximal tissue retention device is configured to reduce its cross sectional area while still grasping the tissue.

7. The septostomy system of claim 6, wherein the proximal tissue retention device is configured to retain the same cross sectional area of tissue while reducing its cross sectional area.

8. The septostomy system of claim 7, further comprising a raised edge part on the perimeter of the proximal capture mechanism.

9. The septostomy system of claim 7, further comprising a tissue retaining mechanism at the perimeter of the tissue capture mechanism.

10. The septostomy system of claim 1, further comprising a locking mechanism configured to hold the force on the tissue between the proximal and distal tissue retention devices.

11. The septostomy system of claim 1, further comprising a spring loaded capture mechanism for maintaining the force within a set range regardless of the thickness of the tissue captured.

12. The septostomy system of claim 1, wherein the tissue retention assembly comprises a proximal tissue capture shaft in the catheter lumen, the proximal tissue capture shaft operatively attached to the proximal tissue capture device.

13. The septostomy system of claim 12, wherein the tissue retention assembly further comprises a distal tissue capture shaft inside the proximal tissue capture shaft, the distal tissue capture shaft operatively attached to the distal tissue capture device.

14. The septostomy system of claim 1, wherein the outer diameter of the proximal tissue retention device is close fitting to the inner diameter of the shaped blade.

15. The septostomy system of claim 1, where in the distal tissue retention device further comprises a tissue trap.

16. The septostomy system of claim 1 further comprising a marker to identify the catheter location on a visualization system.

17. The septostomy system of claim 1 further comprising a means for rotating the shaped blade.

18. The septostomy system of claim 1, further comprising a tissue debulking mechanism.

19. A septostomy assembly comprising:
a catheter assembly, the catheter assembly comprising:
   a catheter shaft, the catheter shaft having a catheter central lumen,
   a shaped blade, the shaped blade comprising:
     a blade cutting edge that is oriented at a substantially right angle to the longitudinal axis of the catheter,
   a tissue retention assembly located at least partially in the catheter central lumen comprising a shaft, a proximal tissue retention device and a distal tissue retention device, the tissue retention devices configured to apply a force between them;
   an actuator, the actuator configured to reduce a gap between the proximal and distal tissue retention devices to grasp a tissue;
   wherein the proximal tissue retention device and the distal tissue retention device are each expandable from a first cross section that fits within the catheter central lumen to a second expanded cross section that exceeds the diameter of the catheter.

20. A method of treating a heart comprising the steps of:
inserting a catheter into the right atrium of the heart, the catheter comprising:
   a catheter shaft having a catheter central lumen
   a shaped cutting blade arranged around the catheter central lumen, a proximal tissue retention device, the proximal tissue retention device having a first cross section and an expanded cross section, a distal tissue retention device, the distal tissue retention device having a first cross section and an expanded cross section, an actuator connected to at least one of the tissue retention devices, while the catheter is in the right atrium, moving a portion of the device into the left atrium, expanding the proximal tissue retention device to the expanded cross section, expanding the distal tissue retention device to the expanded cross section, actuating the actuator to grasp the tissue retention devices in place with a portion of the interatrial septum held between them, cutting an aperture in the interatrial septum between the right atrium and the left atrium, removing a cut tissue from the right atrium.

\* \* \* \* \*